US008153617B2

(12) United States Patent
Whiteford

(10) Patent No.: US 8,153,617 B2
(45) Date of Patent: *Apr. 10, 2012

(54) BRIDGED POLYCYCLIC COMPOUND BASED COMPOSITIONS FOR COATING ORAL SURFACES IN HUMANS

(75) Inventor: Jeffery A. Whiteford, Belmont, CA (US)

(73) Assignee: AllAccem, Inc., San Carlos, CA (US)

( * ) Notice: Subject to any disclaimer, the term of this patent is extended or adjusted under 35 U.S.C. 154(b) by 566 days.

This patent is subject to a terminal disclaimer.

(21) Appl. No.: 12/228,263

(22) Filed: Aug. 11, 2008

(65) Prior Publication Data

US 2009/0105262 A1 Apr. 23, 2009

Related U.S. Application Data

(60) Provisional application No. 60/964,312, filed on Aug. 10, 2007, provisional application No. 60/965,154, filed on Aug. 17, 2007, provisional application No. 61/029,332, filed on Feb. 16, 2008, provisional application No. 61/074,488, filed on Jun. 20, 2008.

(51) Int. Cl.
*A61K 31/33* (2006.01)

(52) U.S. Cl. .................................................... 514/183

(58) Field of Classification Search ........................ None
See application file for complete search history.

(56) References Cited

U.S. PATENT DOCUMENTS

| 2,455,807 | A | 12/1948 | Redmon et al. |
|---|---|---|---|
| 3,066,112 | A | 11/1962 | Bowen |
| 3,179,623 | A | 4/1965 | Bowen |
| 3,194,784 | A | 7/1965 | Bowen |
| 3,751,399 | A | 8/1973 | Lee et al. |
| 3,926,906 | A | 12/1975 | Lee et al. |
| 4,321,268 | A | 3/1982 | Scherm et al. |
| 4,544,359 | A | 10/1985 | Waknine |
| 4,547,531 | A | 10/1985 | Waknine |
| 4,666,896 | A | 5/1987 | Warner, Jr. et al. |
| RE32,581 | E | 1/1988 | Scherm et al. |
| 4,853,987 | A | 8/1989 | Jaworski |
| 4,946,942 | A | 8/1990 | Fuller et al. |
| 5,064,613 | A | 11/1991 | Higgs et al. |
| 5,084,096 | A | 1/1992 | Stovicek |
| 5,118,729 | A | 6/1992 | Piechocki |
| 5,145,853 | A | 9/1992 | Metzger et al. |
| 5,158,766 | A | 10/1992 | Greenwald et al. |
| 5,212,318 | A | 5/1993 | Buckland |
| 5,230,842 | A | 7/1993 | Munde |
| 5,276,068 | A | 1/1994 | Waknine |
| 5,344,856 | A | 9/1994 | Klein |
| 5,348,988 | A | 9/1994 | Suh et al. |
| 5,350,814 | A | 9/1994 | McGarry et al. |
| 5,386,018 | A | 1/1995 | Au et al. |
| 5,389,703 | A | 2/1995 | Lee |
| 5,393,516 | A | 2/1995 | Rheinberger et al. |
| 5,414,878 | A | 5/1995 | Booth |
| 5,494,987 | A | 2/1996 | Imazato et al. |
| 5,496,545 | A | 3/1996 | Holmes-Farley et al. |
| 5,521,246 | A | 5/1996 | Tien et al. |
| 5,534,565 | A | 7/1996 | Zupancic et al. |
| 5,587,023 | A | 12/1996 | Booth |
| 5,597,560 | A | 1/1997 | Bergamini et al. |
| 5,602,193 | A | 2/1997 | Stark |
| 5,658,994 | A | 8/1997 | Burgoyne, Jr. et al. |
| 5,667,775 | A | 9/1997 | Holmes-Farley et al. |
| 5,698,657 | A | 12/1997 | Conner et al. |
| 5,703,231 | A | 12/1997 | Randall et al. |
| 5,753,268 | A | 5/1998 | Stolle et al. |
| 5,753,269 | A | 5/1998 | Groh et al. |
| 5,824,734 | A | 10/1998 | Yang |
| 5,874,516 | A | 2/1999 | Burgoyne, Jr. et al. |
| 5,948,390 | A | 9/1999 | Nelson et al. |
| 5,990,110 | A | 11/1999 | Firestone |
| 6,008,313 | A | 12/1999 | Walker et al. |
| 6,020,370 | A | 2/2000 | Horwell et al. |
| 6,080,170 | A | 6/2000 | Nash et al. |
| 6,187,248 | B1 | 2/2001 | O'Neill et al. |
| 6,190,650 | B1 | 2/2001 | Matthews et al. |
| 6,218,455 | B1 | 4/2001 | Smith et al. |

(Continued)

FOREIGN PATENT DOCUMENTS

GB 599722 1/1947

(Continued)

OTHER PUBLICATIONS

Chand, D. K. et al. "Synthesis of a Heteroditopic Cryptand Capable of Imposing a Distorted Coordination Geometry onto Cu(II): Crystal Structures of the Cryptand (L), [Cu(L)(CN)](picrate), and [Cu(L)(NCS)]{picrate} and Spectroscopic Studies of the Cu(II) Complexes" Inorg. Chem., 1996, vol. 35, 3380-3387.

Chen, C. Z. et.al. "Quaternary Ammonium Functionalized Poly(propylene imine) Dendrimers as Effective Antimicrobials: Structure-Activity Studies" Biomacromolecules, 2000, vol. 1, No. 3, 473-480.

Cunliffe, D. et al., "Bacterial Adhesion at Synthetic Surfaces" Applied and Environmental Microbiology, Nov. 1999, vol. 65, No. 11, 4995-5002.

Dibrov, P. et al. "Chemiosmotic Mechanism of Antimicrobial Activity of Ag+ in *Vibrio cholerae*" Antimicrobial Agents and Chemotherapy, Aug. 2002, vol. 46, No. 8, 2668-2670.

(Continued)

*Primary Examiner* — Noble Jarrell
(74) *Attorney, Agent, or Firm* — Meyertons, Hood, Kivlin, Kowert & Goetzel, P.C.; Eric B. Meyertons

(57) ABSTRACT

A pharmaceutically active agent, a pharmaceutically active agent carrier and method of use thereof are described. In some embodiments, a system may include a composition. The composition may include one or more bridged polycyclic compounds. At least one of the bridged polycyclic compounds may include at least two cyclic groups, and at least two pharmaceutically active agents may be associated with the bridged polycyclic compound. In some embodiments, one or more bridged polycyclic compounds may be applied to an oral surface of a human such that an oral malady may be inhibited and/or ameliorated.

20 Claims, 2 Drawing Sheets

U.S. PATENT DOCUMENTS

| | | | |
|---|---|---|---|
| 6,235,811 | B1 | 5/2001 | Robeson et al. |
| 6,242,526 | B1 | 6/2001 | Siddiqui et al. |
| 6,267,590 | B1 | 7/2001 | Barry et al. |
| 6,268,126 | B1 | 7/2001 | Neenan et al. |
| 6,309,221 | B1 | 10/2001 | Jensen |
| 6,316,044 | B2 | 11/2001 | Ottersbach et al. |
| 6,326,417 | B1 | 12/2001 | Jia |
| 6,350,397 | B1 | 2/2002 | Heikkila et al. |
| 6,416,546 | B1 | 7/2002 | Kimura et al. |
| 6,436,419 | B1 | 8/2002 | Sun et al. |
| 6,440,405 | B1 | 8/2002 | Cooper et al. |
| 6,455,134 | B1 | 9/2002 | Rabasco |
| 6,458,876 | B1 | 10/2002 | Rabasco et al. |
| 6,464,971 | B1 | 10/2002 | Matthews et al. |
| 6,465,042 | B2 | 10/2002 | Saitoh et al. |
| 6,468,953 | B1 | 10/2002 | Hitchems et al. |
| 6,492,445 | B2 | 12/2002 | Siddiqui et al. |
| 6,500,004 | B2 | 12/2002 | Jensen et al. |
| 6,538,143 | B1 | 3/2003 | Pinschmidt, Jr. et al. |
| 6,562,329 | B2 | 5/2003 | Hadvary et al. |
| 6,593,395 | B2 | 7/2003 | Angeletakis et al. |
| 6,608,131 | B1 | 8/2003 | Winterowd et al. |
| 6,617,142 | B2 | 9/2003 | Keogh et al. |
| 6,632,291 | B2 | 10/2003 | Rabon et al. |
| 6,716,955 | B2 | 4/2004 | Burgoyne, Jr. |
| 6,720,368 | B2 | 4/2004 | Field |
| 6,756,364 | B2 | 6/2004 | Barbier et al. |
| 6,803,077 | B2 | 10/2004 | Yu |
| 6,858,203 | B2 | 2/2005 | Holmes-Farley et al. |
| 6,887,517 | B1 | 5/2005 | Cook et al. |
| 6,900,265 | B2 | 5/2005 | Schultz et al. |
| 6,908,609 | B2 | 6/2005 | Simon et al. |
| 6,924,325 | B2 | 8/2005 | Qian |
| 6,929,705 | B2 | 8/2005 | Meyers et al. |
| 6,936,640 | B2 | 8/2005 | McQueen et al. |
| 7,014,846 | B2 | 3/2006 | Holmes-Farley et al. |
| 7,314,857 | B2 | 1/2008 | Madhyastha |
| 7,342,083 | B2 | 3/2008 | Chang et al. |
| 7,385,012 | B2 | 6/2008 | Chang et al. |
| 7,713,955 | B2 | 5/2010 | Whiteford et al. |
| 8,067,402 | B2 | 11/2011 | Whiteford et al. |
| 8,067,403 | B2 | 11/2011 | Whiteford et al. |
| 2001/0009931 | A1 | 7/2001 | Pflug et al. |
| 2002/0151570 | A1 | 10/2002 | Kretschik et al. |
| 2002/0177828 | A1 | 11/2002 | Batich et al. |
| 2003/0091641 | A1 | 5/2003 | Tiller et al. |
| 2003/0134933 | A1 | 7/2003 | Jin et al. |
| 2003/0149149 | A1 | 8/2003 | Carlisle et al. |
| 2003/0175659 | A1 | 9/2003 | Tiba et al. |
| 2003/0190820 | A1 | 10/2003 | Hill et al. |
| 2003/0199605 | A1 | 10/2003 | Fischer |
| 2004/0092896 | A1 | 5/2004 | Thompson |
| 2004/0199994 | A1 | 10/2004 | Sherif et al. |
| 2004/0267009 | A1 | 12/2004 | Redko et al. |
| 2005/0008763 | A1 | 1/2005 | Schachter |
| 2005/0008777 | A1 | 1/2005 | McCleskey et al. |
| 2005/0118911 | A1 | 6/2005 | Oles et al. |
| 2005/0129937 | A1 | 6/2005 | Patton et al. |
| 2005/0158252 | A1 | 7/2005 | Romanowski et al. |
| 2005/0175966 | A1 | 8/2005 | Falsafi et al. |
| 2005/0208249 | A1 | 9/2005 | Wen et al. |
| 2005/0249818 | A1 | 11/2005 | Sawan et al. |
| 2005/0252413 | A1 | 11/2005 | Kangas et al. |
| 2005/0256223 | A1 | 11/2005 | Kolb et al. |
| 2005/0265931 | A1 | 12/2005 | Qian |
| 2005/0271780 | A1 | 12/2005 | Schroeder et al. |
| 2007/0202342 | A1 | 8/2007 | Whiteford et al. |
| 2008/0020127 | A1 | 1/2008 | Whiteford et al. |
| 2008/0021212 | A1 | 1/2008 | Whiteford et al. |
| 2008/0207581 | A1 | 8/2008 | Whiteford et al. |
| 2008/0275141 | A1 | 11/2008 | Whiteford |
| 2009/0054528 | A1 | 2/2009 | Whiteford |
| 2009/0069435 | A1 | 3/2009 | Whiteford |
| 2009/0074833 | A1 | 3/2009 | Whiteford |
| 2009/0270005 | A1 | 10/2009 | Takahashi et al. |
| 2010/0004218 | A1 | 1/2010 | Whiteford |
| 2010/0016270 | A1 | 1/2010 | Whiteford |
| 2011/0015300 | A1 | 1/2011 | Whiteford et al. |

FOREIGN PATENT DOCUMENTS

| | | |
|---|---|---|
| JP | 2005154379 | 6/2005 |
| WO | 2007/029855 | 3/2007 |
| WO | 2007/070801 | 6/2007 |
| WO | 2008/103847 | 8/2008 |

OTHER PUBLICATIONS

Drew, M. G. B. et al., "d10 Cations within triple-helical cryptand hosts; a structural and modelling study" J. Chem. Soc., Dalton Trans., 2000, 1513-1519.

Gibb, B. C. "Strict Self-Assembly and Self-Assembly with Covalent Modifications" Encyclopedia of Supramolecular Chemistry, Aug. 17, 2004, 1372-1378, DOI: 10.1081/E-ESMC-120012781.

Gomez, R. et al., "Synthesis, characterization and photocativity of nanosized sol-gel TiO2-ZrO2 mixed oxides." The 13th International Congress on Catalysis, Jul. 10-15, 2004.

Han, S. et al., "Low-Temperature Synthesis of Highly Crystalline TiO2 Nanocrystals and their Application to Photocatalysis" Small, 2005, vol. 1, No. 8-9, 812-816.

Huang, J. et al., "Thermomechanical properties of polyimide-epoxy nanocomposites from cubic silsesquioxane epoxides" J. Mater. Chem., 2004, vol. 14, 2858-2863.

Imhof, A. "Preparation and Characterization of Titania-Coated Polystyrene Spheres and Hollow Titania Shells" Langmuir, 2001, vol. 17, 3579-3585.

Kraft, A. et al. "Electroluminescent Conjugated Polymers—Seeing Polymers in a New Light" Angew. Chem. Int. Ed., 1998, vol. 37, 402-428.

Lawrence, N. J. et al., "Polymethylhydrosiloxane: a versatile reducing agent for organic synthesis" J. Chem. Soc., Perkin Trans. 1, 1999, 3381-3391.

Lin, J. et al. "Insights into bactericidal action of surface-attached poly(vinyl-N-hexylpyridinium) chains" Biotechnology Letters, 2002, vol. 24, 801-805.

Lin, J. et al. "Making thin polymeric materials, including fabrics, microbicidal and also water-repellent" Biotechnology Letters, 2003, vol. 25, 1661-1665.

Maness, P. et al. "Bactericidal Activity of Photocatalytic TiO2 Reaction: toward an Understanding of Its Killing Mechanism" Applied and Environmental Microbiology, Sep. 1999, vol. 65, No. 9, 4094-4098.

Marlin, D. S. et al. "Complexation-Induced Translational Isomerism: Shuttling through Stepwise Competitive Binding" Angewandte Chemie, 2006, vol. 45, pp. 77-83.

Ming, W. et al., "Superhydrophobic Films from Raspberry-like Particles" Nano. Lett, Oct. 1, 2005, vol. 5, No. 11, 2298-2301.

Ni, B. et al. "Design and Synthesis of Pyridinium Chiral Ionic Liquids Tethered to a Urea Functionality" J. Org. Chem., 2006, vol. 71, 9857-9860.

Pernak, J. et al., "Synthesis and anti-microbial activities of some pyridinium salts with alkoxymethyl hydrophobic group" Eur. J. Med. Chem., 2001, vol. 36, 899-907.

Rivas, F. M. et al. "Aromatic Amination/Imination Approach to Chiral Benzimidazoles" J. Org. Chem., 2002, vol. 67, 1708-1711.

Rowan, S. J. et al. "Dynamic Covalent Chemistry" Angew Chem Int Ed Engl., 2002, vol. 41, No. 6, 898-952.

Salvatore, R. N. et al., "Synthesis of secondary amines" Tetrahedron, 2001, vol. 57, 7785-7811.

Schweizer, H. P. "Efflux as a mechanism of resistance to antimicrobials in *Pseudomonas aeruginosa* and related bacteria: unanswered questions" Genetics and Molecular Research, Mar. 31, 2003, vol. 2, No. 1, 48-62.

Slack, J. M. et al. "Identification of Actinomyces and Related Bacteria in Dental Calculus by the Fluorescent Antibody Technique" J. Dent. Res., 1971, vol. 50, No. 1, 78-82.

Strachan, J. "Synthesis and Characterization of Tetrachlorodiarylethyne-Linked Porphyrin dimers. Effects of Linker Architecture on Intradimer Electronic Communication" Inorg. Chem., 1998, vol. 37, 1191-1201.

Thorsteinsson, T. et.al. "Soft Antimicrobial Agents: Synthesis and Activity of Labile Environmentally Friendly Long Chain Quaternary Ammonium Compounds" J. Med. Chem., 2003, vol. 46, 4173-4181.

Tiller, J. C. et al. "Designing surfaces that kill bacteria on contact" PNAS, 2001, vol. 98, No. 11, 5981-5985.

Tom, R. T. et al., "Freely Dispersible Au@TiO2, Au@ZrO2, Ag@TiO2, and Ag@ZrO2 Core-Shell Nanoparticles: One-Step Synthesis, Characterization, Spectroscopy, and Optical Limiting Properties" Langmuir, 2003, vol. 19, 3439-3445.

Trentler, T. J. et al., "Epoxy Resin-Photopolymer Composites for Volume Holography" Chem. Mater., 2000, vol. 12, 1431-1438.

Waschinski, C. J. et al. "Poly(oxazoline)s with Telechelic Antimicrobial Functions" Biomacromolecules, 2005, vol. 6, 235-243.

Zhang, X. "From Supramolecular Vanadate Receptors to Enzyme Models of Vanadium Haloperoxidase" Philosophisch-Naturwissenschaftlichen Fakultät der Universität Basel, Feb. 2005.

Zhisheng, C. et al "Recent Advances in Antimicrobial Dendrimers", Advanced Materials 2000, vol. 12, No. 11, 843-846.

International Search Report and Written Opinion for PCT/US06/61936 mailed Sep. 12, 2007.

Co-Pending U.S. Appl. No. 11/800,052 entitled, "Methods and Systems for Coating a Surface" to Whiteford et al. filed May 2, 2007.

Marcil, V. et.al. "Butyrate Impairs Lipid Transport by Inhibiting Microsomal Triglyceride Transfer Protein in Caco-2 Cells" J. Nutr. 2003, 133: 2180-2183.

Wren et al. "Dirlotapide: a review of its properties and role in the management of obesity in dogs" 2007 J. vet. Pharmacol. Therap. 30 (Suppl. 1), 11-16.

Hussain, M. M. et.al. "Microsomal triglyceride transfer protein and its role inapoB-lipoprotein assembly" Journal of Lipid Research, 2003, vol. 44, 22-32.

Ni, B. et al. "Design and Synthesis of Pyridinium Chiral Ionic Liquids Tethered to a Urea Functionality", J. Org. Chem. 2006, 71, 26, 9857-9860.

Curd, F. H. S. et al. "Synthetic Antimalarials, Part X, Some Aryldiguanide (-biguanide) Derivatives" J. Chem. Soc. 729-737 (1946).

Chandler, C.E. et al. "CP-346086: an MTP inhibitor that lowers plasma cholesterol and triglycerides in experimental animals and in humans" Journal of Lipid Research, vol. 44, 1887-1901, Oct. 2003.

Curd, F. H. S. et al. "Synthetic Antimalarials, Part XXVIII, An alternative route to N1-aryl-N5-alkyldiguanides" J. Chem. Soc. 1630-1636 (1948).

Co-Pending U.S. Appl. No. 12/775,277 entitled, "Methods and Systems for Coating a Surface" to Whiteford et al. filed May 6, 2010.

Examination Report for Patent Application No. 569756 mailed Feb. 26, 2010.

Written Opinion for European Application No. 08 730 417.6-1216 mailed Aug. 5, 2010.

Office Action for U.S. Appl. No. 11/638,327 mailed on Oct. 2, 2008.
Office Action for U.S. Appl. No. 11/638,327 mailed on May 29, 2009.
Office Action for U.S. Appl. No. 11/638,327 mailed on Nov. 16, 2009.
Office Action for U.S. Appl. No. 11/638,327 mailed on Jun. 1, 2010.
Advisory Action for U.S. Appl. No. 11/638,327 mailed on Sep. 14, 2010.
Office Action for U.S. Appl. No. 11/800,052 mailed on Mar. 5, 2009.
Office Action for U.S. Appl. No. 11/800,052 mailed on Oct. 29, 2009.
Office Action for U.S. Appl. No. 11/800,069 mailed on Aug. 18, 2009.
Office Action for U.S. Appl. No. 11/800,069 mailed on Mar. 22, 2010.
Advisory Action for U.S. Appl. No. 11/800,069 mailed on Jun. 9, 2010.
Office Action for U.S. Appl. No. 12/035,351 mailed on Aug. 5, 2010.
Examination Report for New Zealand Patent Application No. 579785 mailed Oct. 8, 2010. pp. 2.

Bhattacharjee, M. et al. "Synthesis of a New Macrocyclic Ligand with Six Amide Receptor Sites" Tetrahedron Letters (1996) vol. 37, No. 20, 3579-3580.

Office Action for U.S. Appl. No. 11/638,327 mailed on Jan. 20, 2011.
Office Action for U.S. Appl. No. 11/800,069 mailed on Jan. 6, 2011.
Final Office Action for U.S. Appl. No. 12/035,351 mailed on Feb. 3, 2011.
Non-Final Office Action for U.S. Appl. No. 12/228,262 mailed on Mar. 31, 2011.

International Preliminary Report on Patentability for PCT/US2009/053464 mailed Feb. 24, 2011.
Non-Final Office Action for U.S. Appl. No. 12/228,263 mailed on Mar. 31, 2011.
Non-Final Office Action for U.S. Appl. No. 12/228,264 mailed on Mar. 31, 2011.
Final Office Action for U.S. Appl. No. 11/638,327 mailed on Jul. 11, 2011.
Examination Report for Patent Application No. 569756 mailed Apr. 5, 2011.
Advisory Action for U.S. Appl. No. 12/035,351 mailed on May 20, 2011.
Non-Final Office Action for U.S. Appl. No. 12/193,529 mailed on May 27, 2011.

Co-Pending U.S. Appl. No. 12/035,351 entitled, "Bridged Polycyclic Compound Based Compositions for the Inhibition and Amelioration of Disease" to Whiteford filed Feb. 21, 2008.

Hossain, M. A. et al. "Parallels in Cation and Anion Coordination: A New Class of Cascade Complexes" Angew. Chem. Int. Ed., vol. 41, No. 13, 2335-2338, 2002.

Chen, Q. Y. et al. "Synthesis, crystal structure and properties of the first trinuclear copper(II) cryptate bridged by an imidazole anion" J. Chem. Soc., Dalton Trans., 1315-1318, 2002.

Chen, Q. Y. et al. "A study on the heterodinuclear cryptates [LnCuL(DMF)](ClO4)2•MeCN (Ln = Gd, Eu, Tb, Dy, Y)—synthesis, characterization, magnetic and electrochemical properties" J. Chem. Soc., Dalton Trans., 2873-2878, 2002.

Kang, S. G. et al. "Template Synthesis and Crystal Structure of a Novel Mononuclear Nickel(II) Complex with a Face-ti-Face Bis(macrocyclic) Ligand" Inorg. Chem., vol. 36, No. 11, 2478-2481, 1997.

Conejo-Garcia, A. et al. "Synthesis and NMR Studies on a C3-Symmetrical Triquinolina Triscationic Bicyclophane" J. Org. Chem., vol. 70, 5748-5751, 2005.

Shintani, H. "Modification of Medical Device Surface to attain Anti-Infection" Trends Biomater. Artif. Organs, vol. 18 (1), 1-8, 2004.

Kickelbick, G. "Concepts for the incorporation of inorganic building blocks into organic polymers on a nanoscale" Prog. Polym. Sci., vol. 28, 83-114, 2003.

Kull, F. C. et al. "Mixtures of Quaternary Ammonium Compounds and Long-chain Fatty Acids as Antifungal Agents" Appl. Microbiol., vol. 9, No. 6, 538-541, 1961.

Skold, K. et al. "Effect of a chlorhexidine/thymol-containing varnish on prostaglandin E2 levels in gingival crevicular fluid" Eur. J. Oral Sci.., vol. 106, 571-575, 1998.

Co-Pending U.S. Appl. No. 12/228,262 entitled, "Bridged Polycyclic Compound Based Compositions for Coating Oral Surfaces in Pets" to Whiteford filed Aug. 11, 2008.

Dirksen, A. et al. "Nucleophilic Catalysis of Oxime Ligation" Angew. Chem. Int. Ed. (2006) 45, 7581-7584.

Co-Pending U.S. Appl. No. 12/228,264 entitled, "Bridged Polycyclic Compound Based Compositions for Topical Applications for Pets" to Whiteford filed Aug. 11, 2008.

Co-Pending U.S. Appl. No. 12/193,529 entitled, "Bridged Polycyclic Compound Based Compositions for Controlling Bone Resorption" to Whiteford filed Aug. 18, 2008.

Zhuang, X.-M. et al. "Cyanide and imidazolate bridged macrocyclic dinuclear CuII complexes: Synthesis, structure and magnetic properties" Inorganica Chimica Acta 358 (2005) 2129-2134.

Pierre, J. L. et al. "Synthesis of a Novel Macrobicyclic Cavity Possessing Six Convergent Hydroxyl Groups and Acting as a Siderophore" Angew. Chem. Int. Ed. Engl. 30 (1991) No. 1, 85-86.

Shin, C. et al. "Novel Synthesis of the Main Central 2,3,6-Trisubstituted Pyridine Skeleton [Fragment A-B-C] of a Macrobicyclic Antibiotic, Cyclothiazomycin" Bull. Chem. Soc. Jpn. 75, (2002) 1583-1596.

International Search Report and Written Opinion for PCT/US2008/054611 mailed Oct. 7, 2008.

Advisory Action for U.S. Appl. No. 11/638,327 mailed on Jul. 28, 2011.

Notice of Allowance for U.S. Appl. No. 11/638,327 mailed on Aug. 24, 2011.

Non-Final Office Action for U.S. Appl. No. 11/800,066 mailed on Aug. 1, 2011.

Final Office Action for U.S. Appl. No. 11/800,069 mailed on Sep. 16, 2011.

Notice of Allowance for U.S. Appl. No. 11/800,069 mailed on Oct. 4, 2011.

Examination Report for New Zealand Patent Application No. 579785 mailed Aug. 1, 2011. pp. 2.

http://www.bio.brandeis.edu/classes/biochem104/hydrophobic_effect.pdf, 2010.

International Preliminary Report on Patentability for PCT/US06/61936 mailed Jun. 9, 2009.

International Search Report and Written Opinion for PCT/US2009/053464 mailed Feb. 2, 2010.

Chen, D. et al. "The synthesis of new binucleating polyaza macrocyclic and macrobicyclic ligands: dioxygen affinities of the cobalt complexes" Tetrahedron, vol. 47, Issue 34, Aug. 19, (1991), 6895-6902.

Rosenbaum, D. P. et al. "Effect of RenaGel, a non-absorbable, cross-linked, polymeric phosphate binder, on urinary phosphorus excretion in rats" Nephrol Dial Transplant, (1997) 12, 961-964.

Chertow, G. M. et al. "Poly[allylamine hydrochloride] (RenaGel): a noncalcemic phosphate binder for the treatment of hyperphosphatemia in chronic renal failure" Am J Kidney Dis., (1997), 29, 66-71.

David, S. A. et al. "Towards a rational development of anti-endotoxin agents: novel approaches to sequestration of bacterial endotoxins with small molecules" J. Mol. Recognit. (2001); 14: 370-387.

March, Advanced Organic Chemistry, 1992, reaction 6-14, pp. 896-897.

Dayagi, S. et al. "Methods of formation of the carbon-nitrogen double bond", chapter 2 of The Chemistry of the Carbon-Nitrogen Double Bond, editor Saul Patai, 1970, pp. 61-69.

http://www.sigmaaldrich.com/catalog/search/substructure/SubstructureSearchPage, 2010.

Savica, V. et al. "Phosphate binders and management of hyperphosphataemia in end-stage renal disease" Nephrol Dial Transplant (2006) 21: 2065-2068.

Dhal, P. K. et al. "Biologically active polymeric sequestrants: Design, synthesis, and therapeutic applications" Pure Appl. Chem., vol. 79, No. 9, pp. 1521-1530, (2007).

Non-Final Office Action for U.S. Appl. No. 12/035,351 mailed on Oct. 24, 2011.

Final Office Action for U.S. Appl. No. 12/228,262 mailed on Dec. 27, 2011.

Final Office Action for U.S. Appl. No. 12/228,263 mailed on Oct. 18, 2011.

Notice of Allowance for U.S. Appl. No. 12/228,263 mailed on Nov. 25, 2011.

Final Office Action for U.S. Appl. No. 12/228,264 mailed on Oct. 18, 2011.

Notice of Allowance for U.S. Appl. No. 12/228,264 mailed on Nov. 25, 2011.

BRIDGED POLYCYCLIC COMPOUND BASED COMPOSITIONS FOR COATING ORAL SURFACES IN HUMANS

PRIORITY CLAIM

This application claims priority to U.S. Provisional Patent Application No. 60/964,312 entitled "BRIDGED POLYCYCLIC COMPOUND BASED COMPOSITIONS FOR COATING SURFACES" filed on Aug. 10, 2007, U.S. Provisional Patent Application No. 60/965,154 entitled "BRIDGED POLYCYCLIC POLYMER BASED COMPOSITIONS FOR THE INHIBITION AND AMELIORATION OF DISEASE" filed on Aug. 17, 2007, U.S. Provisional Patent Application No. 61/029,332 entitled "BRIDGED POLYCYCLIC COMPOUND BASED COMPOSITIONS FOR COATING SURFACES" filed on Feb. 16, 2008, and U.S. Provisional Patent Application No. 61/074,488 entitled "BRIDGED POLYCYCLIC COMPOUND BASED COMPOSITIONS FOR COATING ORAL SURFACES IN HUMANS" filed on Jun. 20, 2008, all of which are incorporated by reference herein.

BACKGROUND OF THE INVENTION

1. Field of the Invention

The present disclosure generally relates to bridged polycyclic based compounds for the inhibition and amelioration of disease. More particularly, the disclosure generally relates to systems and methods for formulating antiviral, antibacterial, antifungal, antidisease, cleaning compositions using these bridged polycyclic based compounds for treating and/or applying to oral cavities of humans.

2. Description of the Relevant Art

Dendrimers are branched polymers with densely packed end-functional groups that can be used to attach the dendrimers to bioactive molecules such as drugs, targeting ligands and imaging agents. Since a significant portion of a dose of pharmaceutical drugs is lost in the circulation due to impaired uptake by the cells especially in the case of drug resistant cells. The actual concentration of a drug inside the cells is much less than what is present extracellularly. Hence, to accomplish highly effective treatment of diseases it is important to increase the intracellular amount of the drug. Dendrimers have already been used as a carrier agent for several known antiviral agents. Attaching these known agents to a dendrimer has been shown to increase the activity of the agent verses using the agent alone and uncoupled to a dendrimer. However, there are problems associated with using dendrimers, especially when scaling up production to commercial quantities.

Two main methods exist for the synthesis of dendrimers: a divergent approach, where the dendrimer is assembled in a totally linear manner or a convergent method where fragments of the dendrimer are condensed together. These two methods both suffer from major problems when it comes to practical synthesis, in particular, the necessity for repeated and time-consuming purifications.

Additional problems associated with the synthesis of dendrimers are: defects in the molecular structure; and the molecular structure of dendrimers is so crowded that many times other molecules become trapped within the spaces within the molecular structure of the dendrimer Therefore there is a need for a pharmaceutical composition comprising a compound which increases the intracellular amount of pharmaceutical drugs but which is easier and cheaper to synthesize than dendrimers and which are capable of attaching different functionalities more easily.

In the field of dentistry, the increased average age of patients and improvements in the treatment of teeth have resulted in an increased average age of teeth which need to be treated.

The prevention of cavities and periodontitis can therefore not be limited to children and adolescents as the lifelong conservation of teeth demands a preventive approach also for middle-aged and elderly patients. Otherwise there is the risk that the positive results of early preventive measures will be lost within a few years ending up with tooth loss at old age.

Dental applications are challenging and require top performance from dental care providers and materials technology. Materials used in these applications need to be comfortable, hard, wear resistant, strong and yet also visibly appealing. Poorly formulated dental materials can result in discomfort, complications, and increased health care cost to consumers.

All types of teeth and gum diseases can lead to serious health problems in humans. Maintenance of good oral health and prevention of oral disease is a necessity for humans. Unlike animals humans have the ability to exercise control over oral and dental hygiene by using proper preventative techniques. However, humans still experience oral problems ranging from cavities to more severe cases of gum disease.

Human's teeth and gums are susceptible to many oral health problems (e.g., gingivitis and periodontal disease). Periodontal disease affects both human and mammals alike. Periodontal disease is caused by bacteria and plaque that attach to the soft gum tissue of the mouth. The first stage of periodontal disease is gingivitis and is very common. In this stage, the bacteria have mixed with saliva and formed plaque. The plaque adheres to the teeth and hardens, forming tartar and calculus. These tartar deposits irritate the gum tissue and cause inflammation, swelling and infection. It is at this stage that gingivitis is most notable.

There are indications that oral health status has a profound effect on a human's general health. Periodontal disease may cause bacteria and toxins to enter the bloodstream with potentially deleterious effects on internal organs. Conversely, poor systemic health may manifest in the oral cavity in various ways and may also exacerbate periodontal disease. Some humans suffer from chronic oral infection (e.g., stomatitis, a poorly understood condition that is difficult to treat) and oral cancer.

What is needed therefore is an easy to use, effective system for maintaining good oral health as well as preventing and treating oral disease. What are needed are effective methods and compositions for maintaining good oral hygiene, as well as for preventing and treating oral disease in humans. Preferably such methods and compositions should be easy-to-use and comprise antimicrobial and anti-plaque agents. Such methods and compositions should provide long-term effectiveness against oral problems including tartar build-up on teeth, gingivitis, and halitosis. Such methods and compositions should result in improved appearance of the oral cavity such as whiter teeth and healthy gums. Such methods and compositions should be affordable, safe and easy to use on a regular basis.

SUMMARY

Embodiments of the present invention address the problems described above by providing novel compositions and methods for reducing and/or ameliorating maladies associated with an oral cavity. Embodiments of the present invention provide unique methods and compositions that are safe and effective for use by humans.

In some embodiments, a chemical composition may include a chemical compound. The chemical compound may include one or more bridged polycyclic compounds. At least one of the bridged polycyclic compounds may include at least two cyclic groups. At least two pharmaceutically active agents and/or derivatives of pharmaceutically active agents may be coupled to the bridged polycyclic compound.

In some embodiments, at least one of the pharmaceutically active agents may include an anticancer agent, an anti-inflammatory agent, an antimicrobial agent, a lipase inhibitor, a bile acid sequestrant, a cholesterol reduction agent, a periodontal disease inhibitor, a periodontal bacteria attachment inhibitor, a periodontal disease enzyme inhibitor, a periodontal disease enzyme attachment inhibitor.

In some embodiments, a chemical composition may include a chemical compound, wherein the chemical compound has a general structure (Ia):

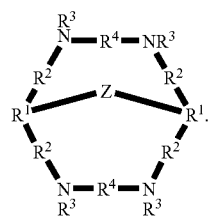

(Ia)

Each $R^1$ may be independently an alkyl group, a substituted alkyl group, an aryl group, a substituted aryl group, N, N⁺H, $N^+R^3$, a heterocycle group, or a substituted heterocycle group. Each $R^2$ may be independently an alkyl group, a substituted alkyl group, an aryl group, a substituted aryl group, a heterocycle group, a substituted heterocycle group, a covalent bond, or an alkene. Each $R^3$ may be independently a hydrogen, pharmaceutically active agent, an ester, an alkyl group, a substituted alkyl group, an aryl group, a substituted aryl group, a heterocycle group, a substituted heterocycle group, an alkene, an ether, an ester, a PEG, an amide, an amine, a guanidine, or a PEI. Each $R^4$ may be independently an alkyl group, a substituted alkyl group, an aryl group, a substituted aryl group, a heterocycle group, a substituted heterocycle group, an ether, an amide, an alcohol, an ester, a sulfonamide, a sulfanilamide, or an alkene. Z may include at least one bridge. At least one of the bridges may be $-R^2-N^+R^3{}_2-R^4-N^+R^3{}_2-R^2-$, $-R^2-NR^3-R^4-N^+R^3{}_2-R^2-$, $-R^2-NR^3-R^4-NR^3-R^2-$, or $-R^2-N=R^4=N-R^2-$. Each bridge may independently couple $R^1$ to $R^1$. The chemical compound may include one or more negatively charged counterions.

In some embodiments, a bridged polycyclic compound may include a salt of compound Ia.

In some embodiments, a chemical composition may include a chemical compound, wherein the chemical compound has a general structure:

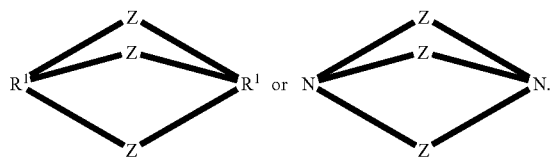

Z may

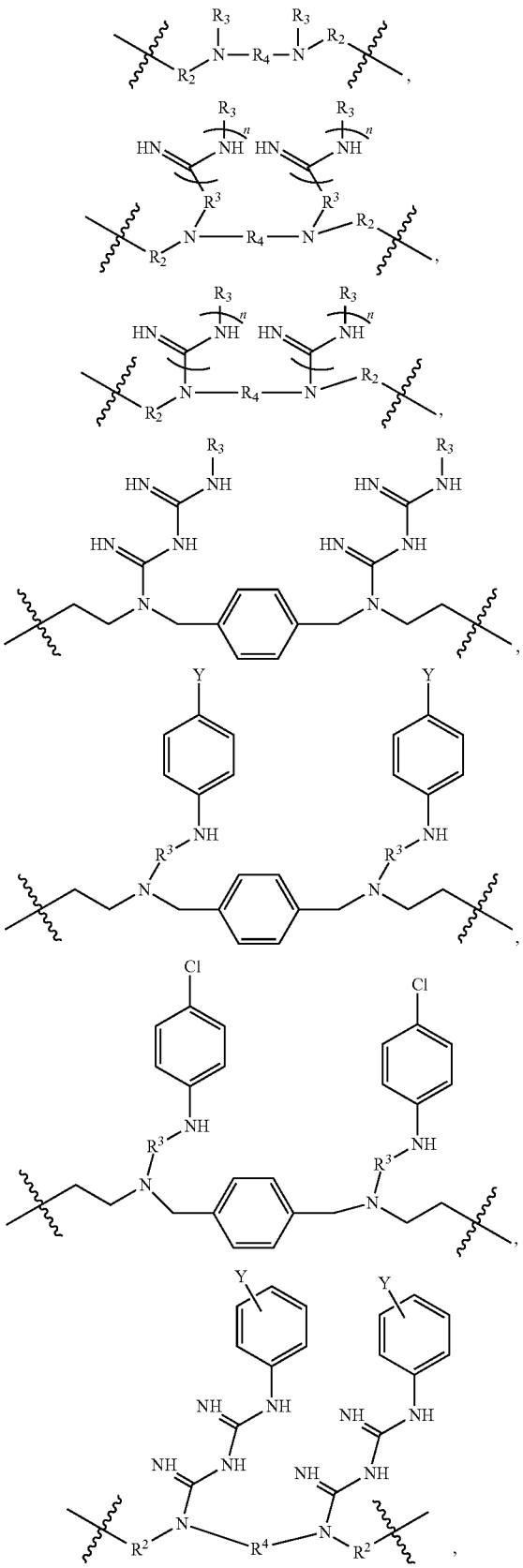

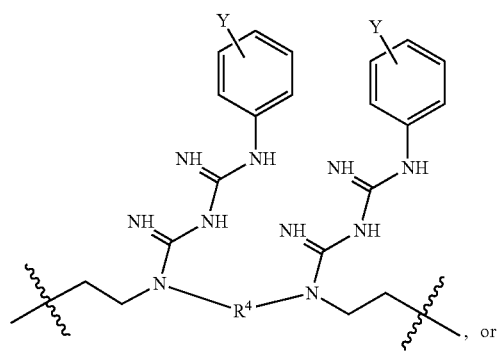, or
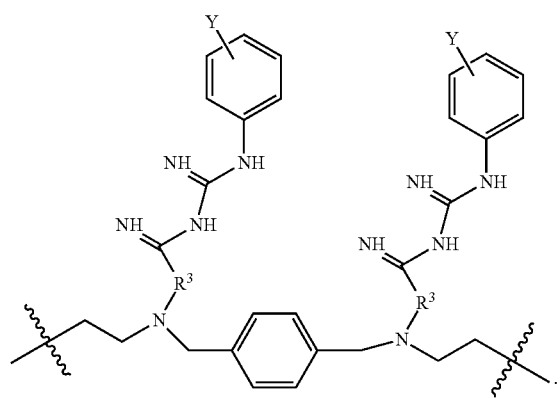
include
In some embodiments, Z may include at least two bridges.
In some embodiments, a chemical composition may include a chemical compound, wherein the chemical compound has a general structure:
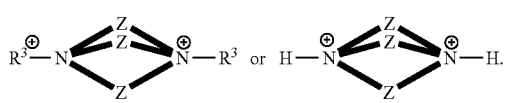
Z may include
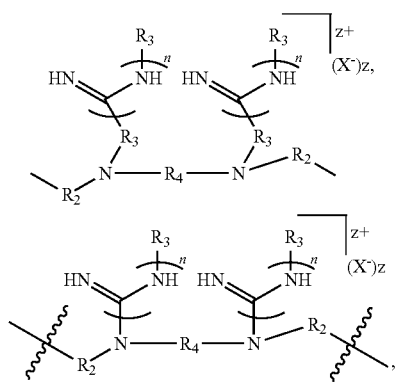
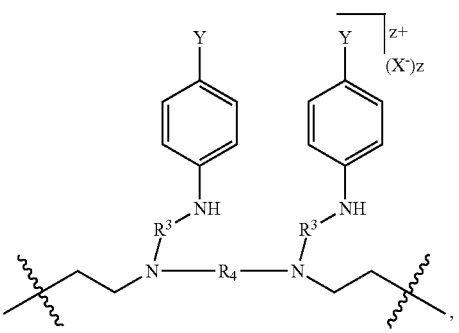,
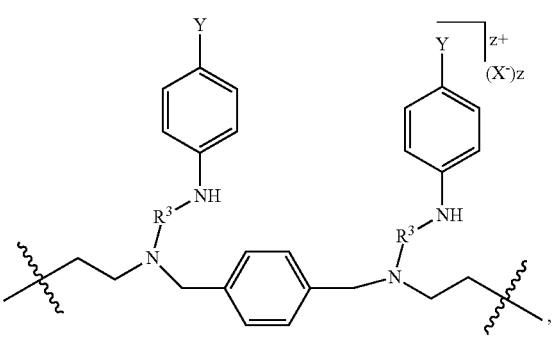,
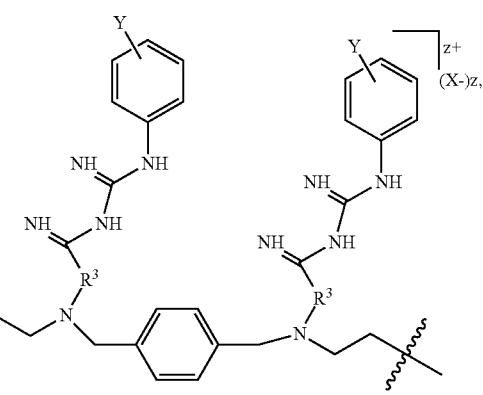
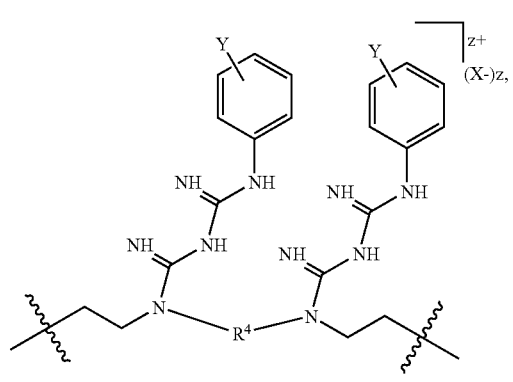

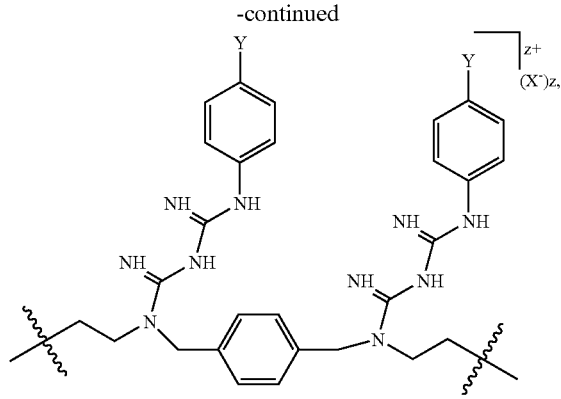
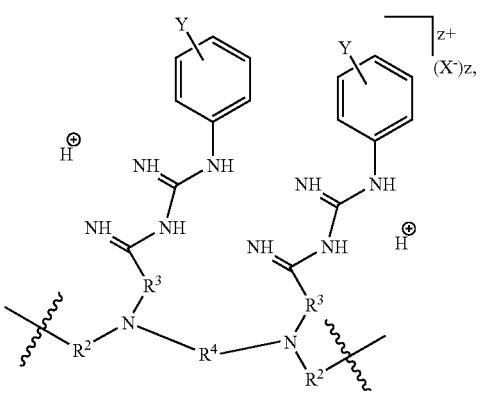
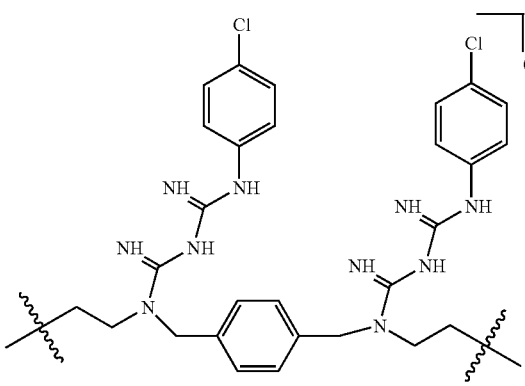
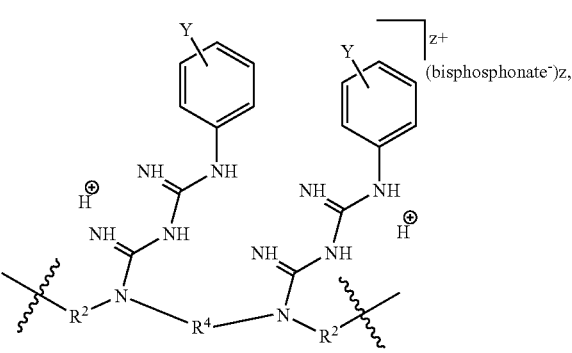
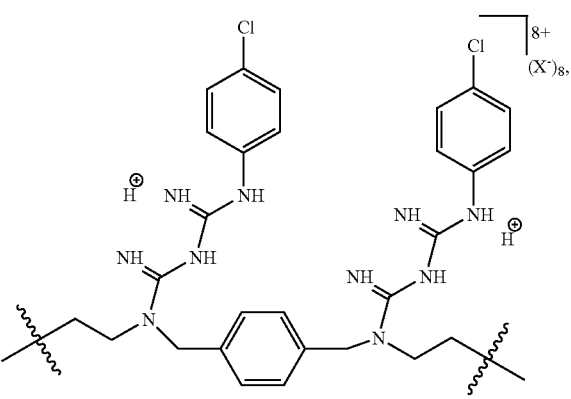
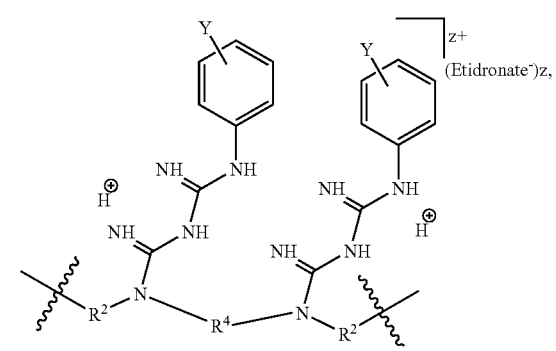
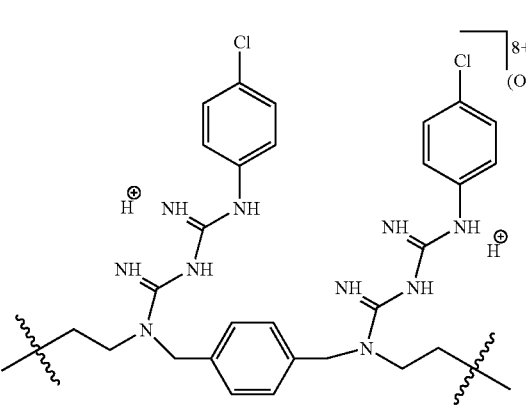
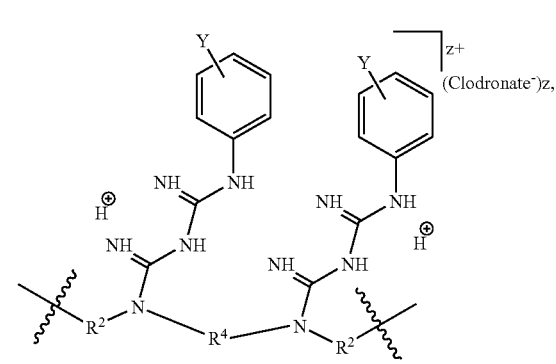

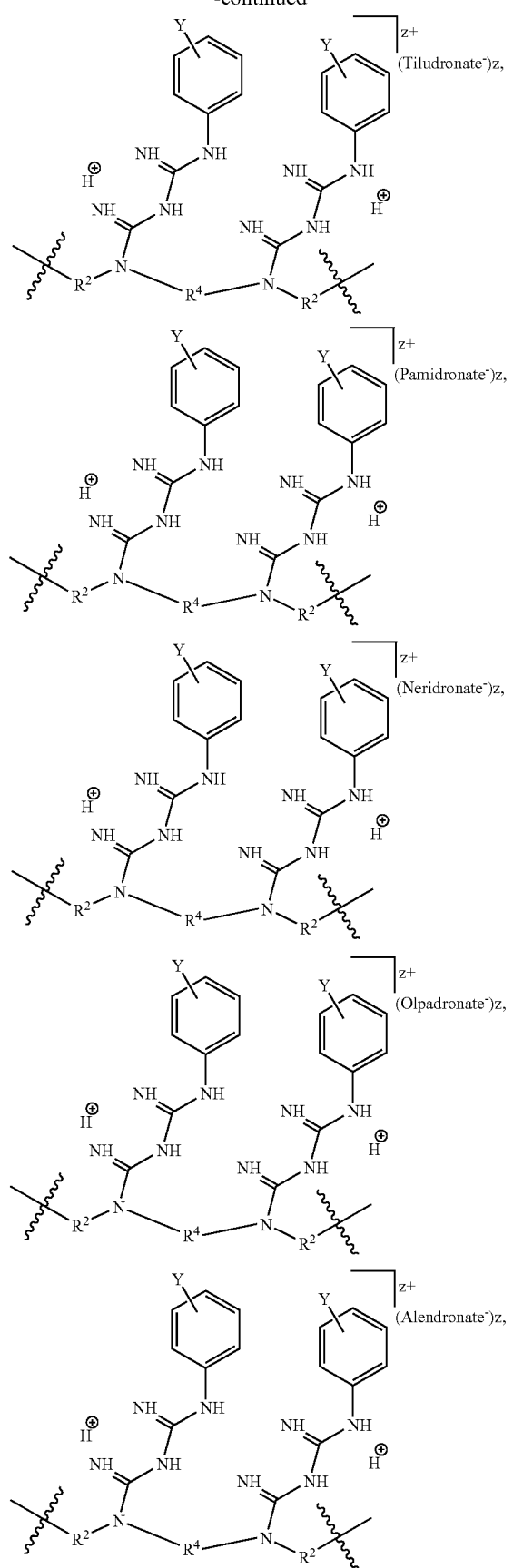
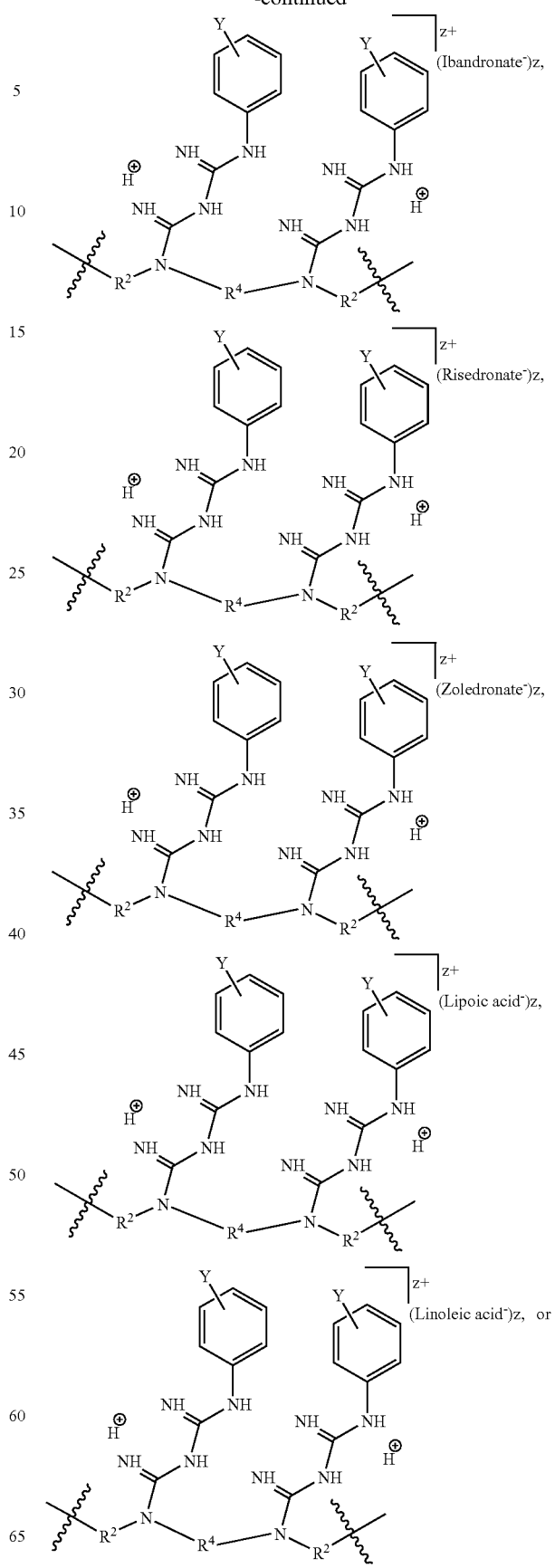

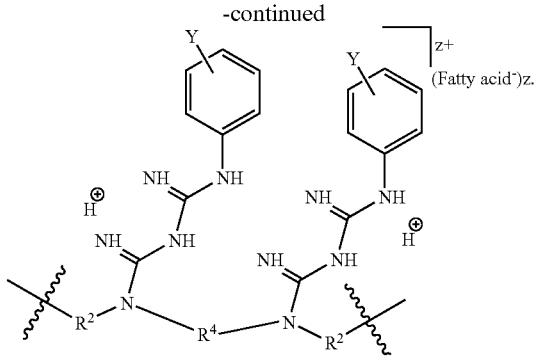

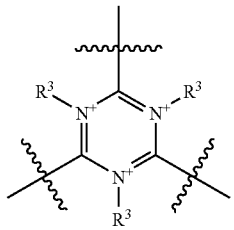

In some embodiments, $R^3$ may include a guanidine moiety, a guanidine derivative and/or a halogenated aryl moiety. $R^3$ may include any of the other moieties associated with $R^3$ herein.

In some embodiments, a chemical compound is a salt of the chemical compound. At least one counterion forming the salt may include an acetate ion.

In some embodiments, Y may include a halogen or an alcohol.

In some embodiments, a chemical composition may include a polymer or a prepolymer. At least one polymer is poly(vinyl acetate-co-crotonic acid).

In some embodiments, a z may represent a charge on the chemical compound and an appropriate number of counterions. z may range from 1-16, 2-14, 6-14, or 8-14.

In some embodiments, y may represent a number of bridges coupling the Nitrogens of the chemical compound. y may range from 3-8, 3-5, or 3-4.

In some embodiments, n may range from 1-8, 1-4, 2-4, or 1-3. n may be at least 2.

In some embodiments, a chemical composition may include at least one solvent.

In some embodiments, a chemical composition may include water and/or an alcohol (e.g., ethanol).

In some embodiments, a chemical composition may include a pharmaceutically acceptable viscous liquid (e.g., glycerin).

In some embodiments, a protective coating composition may include a compound. A compound may include a bridged polycyclic compound. A bridged polycyclic compound may be a cavitand. Portions of the bridged polycyclic compound may include two or more quaternary ammonium moieties. The coating composition may be antimicrobial.

In some embodiments, a protective coating composition may be antimicrobial.

In some embodiments, a compound may include a shape with a substantially curved surface.

In some embodiments, a coating may inhibit microbial adhesion.

In some embodiments, a compound may have a minimum inhibitory concentration of less than 0.1 mg/mL.

In some embodiments, a composition may have a minimum inhibitory concentration of less than 0.05 mg/mL.

In some embodiments, at least one $R^1$ is $N^+R^3$. In some embodiments, at least one $R^1$ is In some embodiments, at least one $R^3$ is hydrophilic. In some embodiments, at least one $R^3$ is a polymer. In some embodiments, at least one $R^3$ is an oxazoline polymer. In some embodiments, at least one $R^3$ is hydrophobic.

In some embodiments, at least one $R^4$ may be

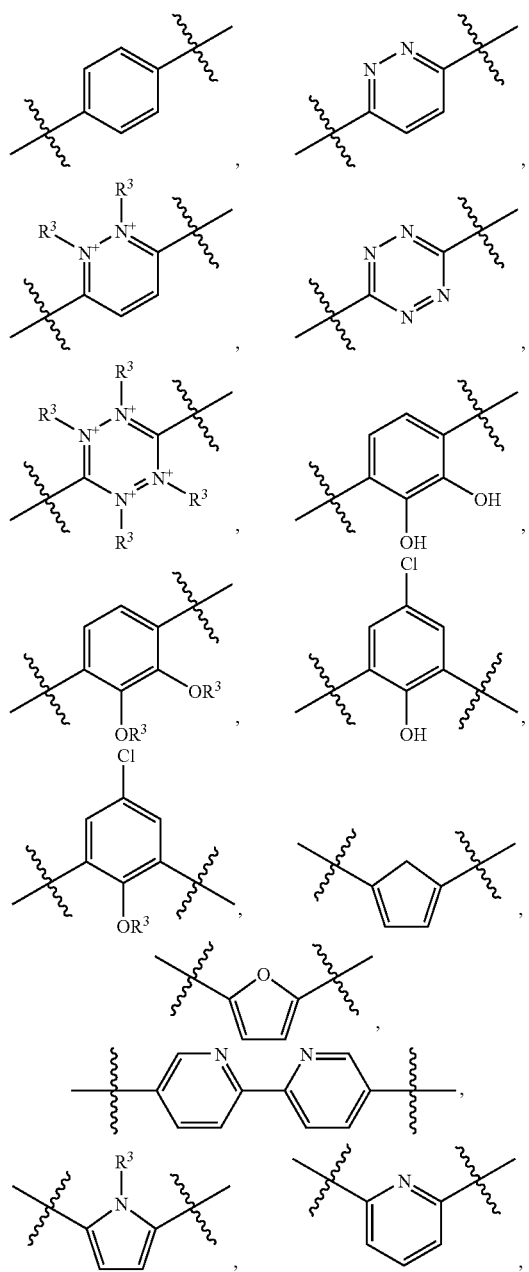

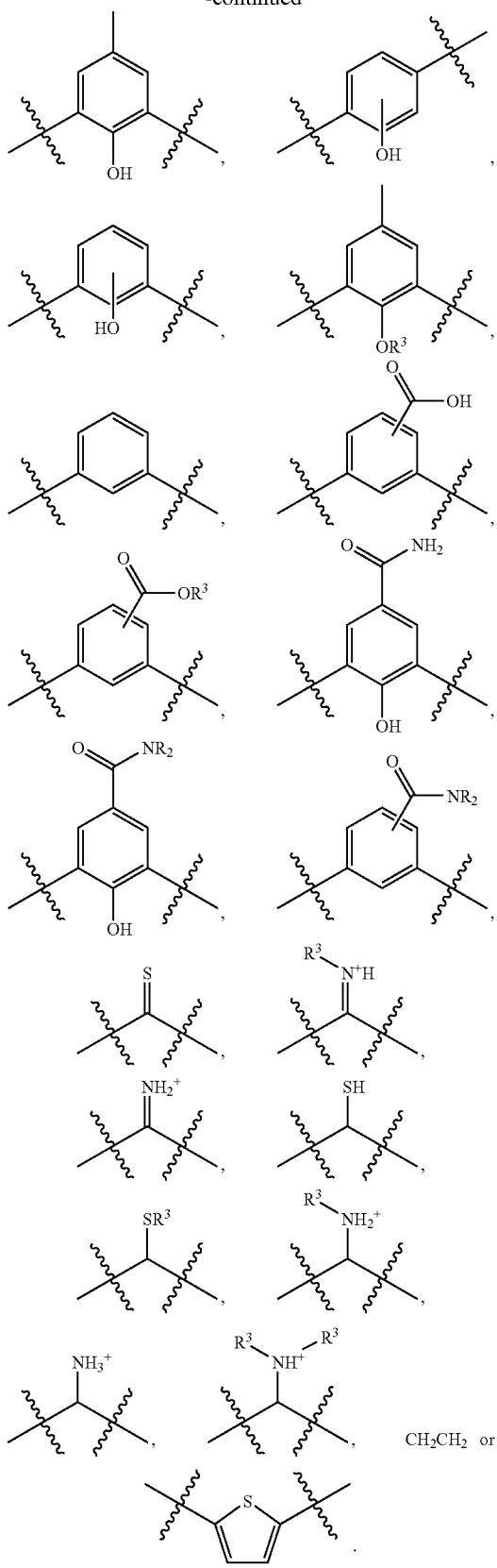

In some embodiments, a composition may include at least one metal (M) coordinated to at least a portion of the compound. At least one M may include a cation. At least one M may be positioned inside a space defined by $R^2$ and $R^4$, and wherein at least one M is coordinated to one or more $N^+R^3_2$'s.

In some embodiments, at least one X may include a halogen ion.

In some embodiments, at least one X may include one or more elements with antimicrobial activity.

In some embodiments, at least one X may include one or more elements with anti-inflammatory activity In some embodiments, at least one X may include boron.

In some embodiments, a composition may include one or more metals and/or metal ions with antimicrobial properties.

In some embodiments, a composition may include one or more metals and/or metal ions with anti-inflammatory properties.

In some embodiments, at least a portion of a chemical composition may form an antimicrobial coating over at least a portion of a surface. The chemical composition may include one or more bridged polycyclic compounds. At least one of the bridged polycyclic compounds may include at least two cyclic groups.

In some embodiments, a compound and/or a composition may have a minimum inhibitory concentration of greater than 900 μM (e.g., 900 μM-1500 μM, 900 μM-2000 μM, 1500 μM-2500 μM, etc.). In some embodiments, a compound and/ or a coating composition may have a minimum inhibitory concentration of less than 10.0 mg/mL, less than 5.0 mg/mL, less than 1.0 mg/mL, less than 0.1 mg/mL, or less than 0.05 mg/mL. In such compositions, antimicrobial properties may not be the primary function of a coating composition.

In some embodiments, a method of coating an oral surface may include applying a composition to a surface of an oral surface. The composition may include one or more bridged polycyclic compounds. At least one of the bridged polycyclic compounds may include at least two cyclic groups. The method may include forming an antimicrobial coating over at least a portion of the surface.

The oral surface may include at least a portion of a tooth surface, at least a portion of a gum, at least a portion of soft tissue, or at least a portion of a dental fixture. A dental fixture may include a filling, at least a portion of a bridge, or at least a portion of a denture.

The composition may be in the form of a gel, a sealant, a varnish, a resin, and/or a coating.

In some embodiments, a composition may include a coalescing solvent.

The method may include using the composition as a bonding agent.

The method may include using the composition as a resin cement.

The method may include using the composition as a sealant.

The method may include using the composition as a varnish.

The method may include using the composition as a resin.

In some embodiments, an oral surface may be coated with a coating. The coating may include a chemical composition at least a portion of which forms an antimicrobial coating over at least a portion of the oral surface. The coating may include a chemical composition at least a portion of which forms an anti-inflammatory coating over at least a portion of the oral surface. The coating may include a chemical composition at least a portion of which decreases bleeding over at least a portion of the oral surface. The coating may include a chemical composition at least a portion of which decreases inflammation over at least a portion of the oral surface. The coating may include a chemical composition at least a portion of decreases bacterial, viral and/or fungal infection over at least a portion of the oral surface. The coating may include a chemical composition at least a portion of which decreases infection over at least a portion of the oral surface. The chemical composition may include one or more bridged polycyclic compounds. At least one of the bridged polycyclic compounds may include at least two cyclic groups. At least two cyclic groups may be defined in part by quaternary ammonium moieties.

In some embodiments, a method of inhibiting or ameliorating a disease may include administering to a subject an effective amount of a pharmaceutically acceptable formulation comprising a chemical composition as described herein.

In some embodiments, a subject may include a human.

In some embodiments, a method may include administering at least two different pharmaceutically active agents. The agents may be coupled to the same and/or different bridged polycyclic compounds.

In some embodiments, a chemical compound may decompose during use, wherein one or more of the products of the decomposition may be more biologically active relative to the chemical compound.

In some embodiments, a method may include administering the pharmaceutically acceptable formulation to a subject in the form of an emulsion.

BRIEF DESCRIPTION OF THE DRAWINGS

Advantages of the present invention may become apparent to those skilled in the art with the benefit of the following detailed description of the preferred embodiments and upon reference to the accompanying drawings in which.

Figure 1:
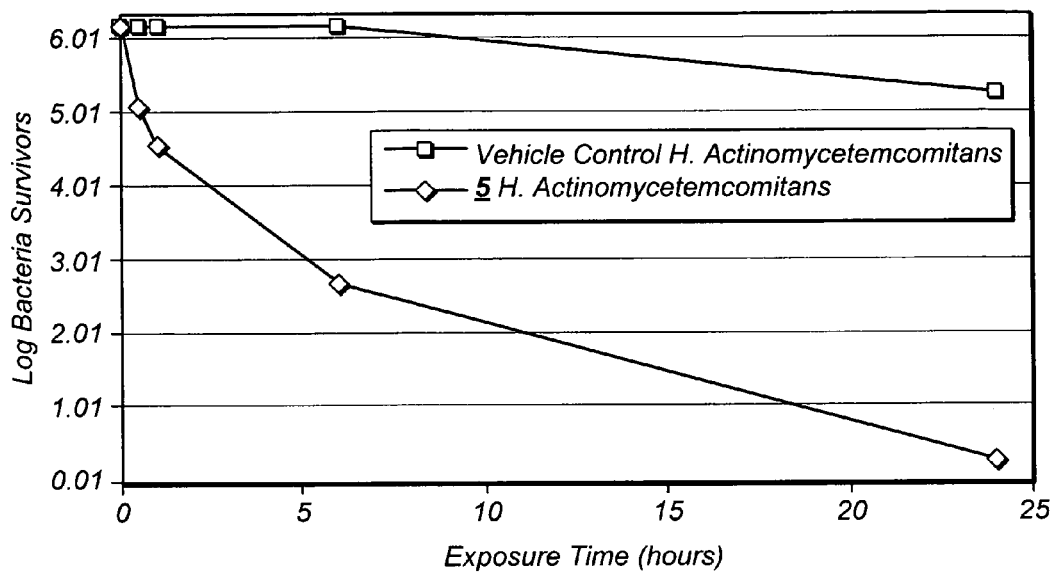
FIG. 1 depicts a graphical representation of time kill assay tests for a bridged polycyclic compound tested against *Haemophilus* Actinomycetemcomitans.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

Definitions

Unless defined otherwise, all technical and scientific terms used herein have the same meaning as commonly understood by one of ordinary skill in the art.

The term "accelerator" as used herein generally refers to a substance that speeds a chemical reaction.

The term "acyl" as used herein generally refers to a carbonyl substituent, —C(O)R, where R is alkyl or substituted alkyl, aryl, or substituted aryl, which may be called an alkanoyl substituent when R is alkyl.

The terms "administration," "administering," or the like, as used herein when used in the context of providing a pharmaceutical, cosmoceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered parenteral, subcutaneous, intravenous, intracoronary, rectal, intramuscular, intra-peritoneal, transdermal, or buccal routes of delivery. Alternatively, or concurrently, administration may be by the oral route. The dosage administered will be dependent upon the age, health, weight, and/or disease state of the recipient, kind of concurrent treatment, if any, frequency of treatment, and/or the nature of the effect desired. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The term "aldehyde" as used herein generally refers to any of a class of organic compounds containing the group

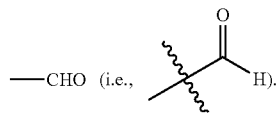

The term "aldehyde forming moiety" as used herein generally refers to any of a class of organic compounds which form an aldehyde in solution or react in an equivalent manner to an aldehyde such that an at least similar chemical product is achieved as would have been achieved with an aldehyde.

The terms "alkenyl" and "alkene" as used herein generally refer to any structure or moiety having the unsaturation C═C. As used herein, the term "alkynyl" generally refers to any structure or moiety having the unsaturation C≡C.

The term "alkoxy" generally refers to an —OR group, where R is an alkyl, substituted lower alkyl, aryl, substituted aryl. Alkoxy groups include, for example, methoxy, ethoxy, phenoxy, substituted phenoxy, benzyloxy, phenethyloxy, t-butoxy, and others.

The term "alkyl" as used herein generally refers to a chemical substituent containing the monovalent group $C_nH_{2n}$, where n is an integer greater than zero. Alkyl includes a branched or unbranched monovalent hydrocarbon radical. An "n-mC" alkyl or "(nC-mC)alkyl" refers to all alkyl groups containing from n to m carbon atoms. For example, a 1-4C alkyl refers to a methyl, ethyl, propyl, or butyl group. All possible isomers of an indicated alkyl are also included. Thus, propyl includes isopropyl, butyl includes n-butyl, isobutyl and t-butyl, and so on. The term alkyl may include substituted alkyls.

The term "alkyl-aryl" as used herein generally refers to a chemical substituent containing an alkyl group coupled to an aryl group or a substituted aryl group.

The terms "amino" or "amine" as used herein generally refer to a group —NRR', where R and R' may independently include, but are not limited to, hydrogen, alkyl, substituted alkyl, aryl, substituted aryl or acyl. Amine or amino may include a salt of the amine group.

The terms "amine forming moiety" as used herein generally refers to any of a class of organic compounds which form an amine in solution or react in an equivalent manner to an amine such that an at least similar chemical product is achieved as would have been achieved with an amine.

The terms "amphiphile" or "amphiphilic" as used herein generally refer to a molecule or species which exhibits both hydrophilic and lipophilic character. In general, an amphiphile contains a lipophilic moiety and a hydrophilic moiety. The terms "lipophilic" and "hydrophobic" are interchangeable as used herein. An amphiphile may form a Langmuir film.

Non-limiting examples of hydrophobic groups or moieties include lower alkyl groups, alkyl groups having 6, 7, 8, 9, 10, 11, 12, or more carbon atoms, including alkyl groups with 14-30, or 30 or more carbon atoms, substituted alkyl groups, alkenyl groups, alkynyl groups, aryl groups, substituted aryl groups, saturated or unsaturated cyclic hydrocarbons, heteroaryl, heteroarylalkyl, heterocyclic, and corresponding substituted groups. A hydrophobic group may contain some hydrophilic groups or substituents insofar as the hydrophobic character of the group is not outweighed. In further variations, a hydrophobic group may include substituted silicon atoms, and may include fluorine atoms. The hydrophobic moieties may be linear, branched, or cyclic.

Non-limiting examples of hydrophilic groups or moieties include hydroxyl, methoxy, phenyl, carboxylic acids and salts thereof, methyl, ethyl, and vinyl esters of carboxylic acids, amides, amino, cyano, isocyano, nitrile, ammonium salts, sulfonium salts, phosphonium salts, mono- and di-alkyl substituted amino groups, polypropyleneglycols, polyethylene glycols, glycosyl groups, sugars, epoxy groups, acrylates, sulfonamides, nitro, —OP(O)(OCH$_2$CH$_2$N$^+$RRR)O$^-$, guanidinium, aminate, acrylamide, pyridinium, piperidine, and combinations thereof, wherein each R is independently selected from H or alkyl. Further examples include polymethylene chains substituted with alcohol, carboxylate, acrylate, or methacrylate. Hydrophilic moieties may also include alkyl chains having internal amino or substituted amino groups, for example, internal —NH—, —NC(O)R—, or —NC(O)CH═CH$_2$— groups, wherein R is H or alkyl. Hydrophilic moieties may also include polycaprolactones, polycaprolactone diols, poly(acetic acid)s, poly(vinyl acetates)s, poly(2-vinyl pyridine)s, cellulose esters, cellulose hydroxylethers, poly(L-lysine hydrobromide)s, poly(itaconic acid)s, poly(maleic acid)s, poly(styrenesulfonic acid)s, poly(anilines)s, or poly(vinyl phosphonic acids)s. A hydrophilic group may contain some hydrophobic groups or substituents insofar as the hydrophilic character of the group is not outweighed.

The term "animal" as used herein generally refers to any member of the kingdom Animalia, comprising multicellular organisms that have a well-defined shape and usually limited growth, can move voluntarily, actively acquire food and digest it internally, and have sensory and nervous systems that allow them to respond rapidly to stimuli: some classification schemes also include protozoa and certain other single-celled eukaryotes that have motility and animallike nutritional modes. Generally the term animal as used herein does not refer to humans.

The term "antiinflammatory" as used herein generally refers to a substance acting to reduce certain signs of inflammation (e.g., swelling, tenderness, fever, and pain).

The term "antimicrobial" as used herein generally refers to a substance capable of destroying or inhibiting the growth of microbes, prevents the development of microbes, and/or inhibits the pathogenic action of microbes as well as viruses, fungi, and bacteria.

The term "aryl" as used herein generally refers to a chemical substituent containing an aromatic group (e.g., phenyl). An aromatic group may be a single aromatic ring or multiple aromatic rings which are fused together, coupled covalently, or coupled to a common group such as a methylene, ethylene, or carbonyl, and includes polynuclear ring structures. An aromatic ring or rings may include, but is not limited to, substituted or unsubstituted phenyl, naphthyl, biphenyl, diphenylmethyl, and benzophenone groups. The term "aryl" includes substituted aryls The term "avian" as used herein generally refers to any of the biological family Aves including a class of vertebrates comprising the birds. Aves are generally characterized by have a complete double circulation, oviparous, reproduction, front limbs peculiarly modified as wings; and they bear feathers. All existing birds have a horny beak, without teeth.

The term "bridged polycyclic compound" as used herein generally refers to a compound that is composed of two or more cyclic systems that share two or more atoms. A cyclic system is formed from a group of atoms which together form a continuous loop. A bridged polycyclic compound may include a bridging atom or group of atoms that connects two or more non-adjacent positions of the same ring. An example of a bridged bicyclic system (i.e., a compound composed of two cyclic systems) with two atoms (atoms "A") common to both cyclic systems is depicted below. One of the linking groups "L" represents a bridging atom or group of atoms.

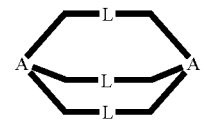

The term "building substrate" as used herein generally refers to a natural or synthetic material used in the construction of a residential or commercial structure.

The term "canine" as used herein generally refers to any of the biological family Canidae including carnivorous mammals including wolves, jackals, foxes, coyote, and the domestic dog.

The term "cavitand" as used herein generally refers to a natural or synthetic molecular compound with enforced cavities large enough to complex complementary compounds or ions. More specifically, a cavitand may be generally defined as a three-dimensional compound that maintains a substantially rigid structure and binds a variety of molecules in the cavities produced by the structure of the three-dimensional compound.

The term "chelating agent or complexing agent" as used herein generally refers to any of various compounds that combine with metals to form chelates.

The term "coalescing agents or solvents" as used herein generally refers to any of various compounds that are used in coatings to promote film formation (e.g., in architectural and industrial latex coating).

The terms "coupling" and "coupled" with respect to molecular moieties or species, atoms, synthons, cyclic compounds, and nanoparticles refers to their attachment or association with other molecular moieties or species, atoms, synthons, cyclic compounds, and nanoparticles. The attachment or association may be specific or non-specific, reversible or non-reversible, the result of chemical reaction, or complexation or charge transfer. The bonds formed by a coupling reaction are often covalent bonds, or polar-covalent bonds, or mixed ionic-covalent bonds, and may sometimes be Coulombic forces, ionic or electrostatic forces or interactions.

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal typically does not extend beyond the boundaries of the crystal. In this case, "long-range ordering" will mean substantial order across at least the majority of the dimension of the nanostructure. In some instances, a nanostructure may bear an oxide or other coating, or may be comprised of a core and at least one shell. In such instances it will be appreciated that the oxide, shell(s), or other coating need not exhibit such ordering (e.g., it may be amorphous, polycrystalline, or otherwise). In such instances, the phrase "crystalline," "substantially crystalline," "substantially monocrystalline," or "monocrystalline" refers to the central core of the nanostructure (excluding the coating layers or shells). The terms "crystalline" or "substantially crystalline" as used herein are intended to also encompass structures comprising various defects, stacking faults, atomic substitutions, etc., as long as the structure exhibits substantial long range ordering (e.g., order over at least about 80% of the length of at least one axis of the nanostructure or its core). It may be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein.

The term "cyclic" as used herein generally refers to compounds having wherein at least some of the atoms are arranged in a ring or closed-chain structure.

The term "dental compositions" as used herein generally refers to any substances typically associated with any type of dental work and/or in related fields and includes, but is not limited to, dental primers, adhesives, surface sealants, liners, luting cements, varnishes, impression materials, equipment and impression systems, and composite restoratives.

The term "dental fixture" as used herein generally refers to an at least partially synthetic material configured to positioned in and/or coupled to at least a portion of an oral cavity. For example a dental fixture may include, but is not limited to, a filling, a bridge, a false tooth, a cap, or denture.

The term "disease" as used herein generally refers to a disordered or incorrectly functioning organ, part, structure, or system of the body resulting from the effect of genetic or developmental errors, infection, poisons, nutritional deficiency or imbalance, toxicity, or unfavorable environmental factors; illness; sickness; ailment.

The terms "effective concentration" or "effective amount" as used herein generally refers to a sufficient amount of the pharmaceutically active agent is added to decrease, prevent or inhibit the growth of a virus and/or cancerous growth. The amount will vary for each compound and upon known factors related to the item or use to which the pharmaceutically active agent is applied.

The phrase "enteric coating" as used herein generally refers to a barrier applied to oral medication that controls the location in the digestive system where it is absorbed. Enteric refers to the small intestine, therefore enteric coatings prevent release of medication before it reaches the small intestine. Most enteric coatings work by presenting a surface that is stable at the highly acidic pH found in the stomach, but breaks down rapidly at a less acidic (relatively more basic) pH. For example, they will not dissolve in the acidic juices of the stomach (pH~3), but they will in the higher pH (above pH 5.5) environment present in the small intestine.

The term "feline" as used herein generally refers to any of the biological family Felidae including lithe-bodied carnivorous mammals (as the lion, lynx, and cheetah, as well as the common house cat) having often strikingly patterned fur, comparatively short limbs with soft pads on the feet, usually sharp curved retractile claws, a broad and somewhat rounded head with short but powerful jaws equipped with teeth suited to grasping, tearing, and shearing through flesh, erect ears, and typically eyes with narrow or elliptical pupils and especially adapted for seeing in dim light.

The terms "functionalized" or "functional group" as used herein generally refers to the presence of a reactive chemical moiety or functionality. A functional group may include, but is not limited to, chemical groups, biochemical groups, organic groups, inorganic groups, organometallic groups, aryl groups, heteroaryl groups, cyclic hydrocarbon groups, amino (—NH$_2$), hydroxyl (—OH), cyano (—C≡N), nitro (NO$_2$), carboxyl (—COOH), formyl (—CHO), keto (—CH$_2$C(O)CH$_2$—), ether (—CH$_2$—O—CH$_2$—), thioether (—CH$_2$—S—CH$_2$—), alkenyl (—C═C—), alkynyl, (—C≡C—),

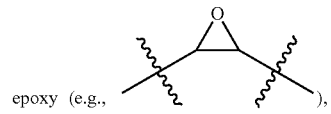

epoxy (e.g., ), metalloids (functionality containing Si and/or B) and halo (F, Cl, Br, and I) groups. In some embodiments, the functional group is an organic group.

The term "gram-negative bacteria" or "gram-negative bacterium" as used herein generally refers to bacteria which have been classified by the Gram stain as having a red stain. Gram-negative bacteria have thin walled cell membranes consisting of a single layer of peptidoglycan and an outer layer of lipopolysacchacide, lipoprotein, and phospholipid. Exemplary organisms include, but are not limited to, Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*. Other exemplary gram-negative organisms not in the family Enterobacteriacea include, but are not limited to, *Pseudomonas aeruginosa, Stenotrophomonas maltophilia, Burkholderia, Cepacia, Gardenerella, Vaginalis*, and *Acinetobacter* species.

The term "gram-positive bacteria" or "gram-positive bacterium" as used herein generally refers to bacteria, which have been classified using the Gram stain as having a blue stain. Gram-positive bacteria have a thick cell membrane consisting of multiple layers of peptidoglycan and an outside layer of teichoic acid. Exemplary organisms include, but are not limited to, *Staphylococcus aureus*, coagulase-negative staphylococci, streptococci, enterococci, corynebacteria, and *Bacillus* species.

The term "guanidine" as used herein generally refers to

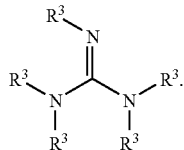

Guanidine may (e.g., 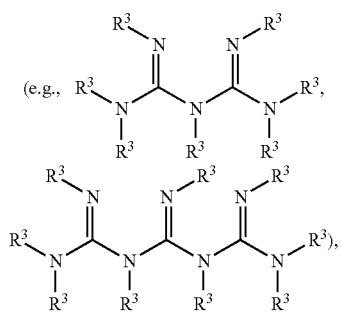), also refer to derivatives of guanidine (e.g., including, for example, salts of guanidine.

The term "heteroaryl" generally refers to a completely unsaturated heterocycle.

The term "heterocycle" as used herein generally refers to a closed-ring structure, in which one or more of the atoms in the ring is an element other than carbon. Heterocycle may include aromatic compounds or non-aromatic compounds. Heterocycles may include rings such as thiophene, pyridine, isoxazole, phthalimide, pyrazole, indole, furan, or benzo-fused analogues of these rings. Examples of heterocycles include tetrahydrofuran, morpholine, piperidine, pyrrolidine, and others. In some embodiments, "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms (e.g., N, O, and S) and wherein the nitrogen and sulfur heteroatoms may optionally be oxidized, and the nitrogen may optionally be quaternized, and including any bicyclic group in which any of the above-defined heterocyclic rings is fused to a benzene ring. In some embodiments, heterocycles may include cyclic rings including boron atoms. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzofuranyl, benzothiophenyl, carbazole, chromanyl, chromenyl, cinnolinyl, decahydroquinolinyl, furanyl, furazanyl, imidazolidinyl, imidazolinyl, imidazolyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, oxazolidinyl, oxazolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, pyrrolyl, quinazolinyl, quinolinyl, quinoxalinyl, quinuclidinyl, carbolinyl, tetrahydrofuranyl, tetrahydroisoquinolinyl, tetrahydroquinolinyl, tetrazolyl, thianthrenyl, thiazolyl, thienyl, thiophenyl, triazinyl, xanthenyl. Also included are fused ring and spiro compounds containing, for example, the above heterocycles.

The term "initiator" as used herein generally refers to a substance that initiates a chemical reaction.

The term "ion" as used herein generally refers to an atom(s), radical, or molecule(s) that has lost or gained one or more electrons and has thus acquired an electric charge.

The terms "in need of treatment" or "in need thereof" when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The term "malady" as used herein generally refers to any disorder or disease of the body or any undesirable or disordered condition including, but not limited to, illness, sickness, affliction, complaint, ailment, indisposition, virus, disease, fungus, infection, disease, etc.

The term "mammal" as used herein generally refers to any vertebrate of the class Mammalia, having the body more or less covered with hair, nourishing the young with milk from the mammary glands, and, with the exception of the egg-laying monotremes, giving birth to live young. Generally the term mammal as used herein does not refer to humans.

The term "matrix" generally refers to a material, often a polymeric material and/or a prepolymeric material, into which a second material (e.g., a nanostructure) is embedded, surrounded, or otherwise associated. A matrix is typically composed of one or more monomers, but may include other matrix components/constituents. Often the matrix constituents include one or more "addressable" components or complementary binding pairs, that optionally promote assembly and/or cross-linkage of the matrix.

The term "medical device" as used herein generally refers to a device used which pertains to treating or determining the state of one's health. Medical devices are any article that contacts subjects or are used in health care, and may be for use either internally or externally.

The term "microbe" as used herein generally refers to a minute life form; a microorganism. In some embodiments, a microbe may include a bacterium that causes disease.

The term "modulate," as used herein, generally refers to a change or an alteration in the magnitude of a be used herein to biological parameter such as, for example, foci formation, tumorigenic or neoplastic potential, apoptosis, growth kinetics, expression of one or more genes or proteins of interest, metabolism, oxidative stress, replicative status, intercellular communication, or the like. "Modulation" may refer to a net increase or a net decrease in the biological parameter.

The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal.

The terms "monofunctional", "bifunctional", "trifunctional", and "multifunctional" generally refers to a number of attachment sites a particular compound, molecule, atom, etc. may include (monofunctional having one site, bifunctional having two sites, trifunctional having three sites, and multifunctional having more than one site).

The term "nanocrystal" as used herein generally refers to a nanostructure that is substantially monocrystalline. A nanocrystal thus has at least one region or characteristic dimension with a dimension of less than about 500 nm, e.g., less than about 200 nm, less than about 100 nm, less than about 50 nm, or even less than about 20 nm. The region or characteristic dimension may be along the smallest axis of the structure. Examples of such structures include nanowires, nanorods, nanotubes, branched nanowires, nanotetrapods, nanotripods, nanobipods, nanocrystals, nanodots, quantum dots, nanoparticles, nanoribbons, etc. Nanostructures may be substantially homogeneous in material properties, or in certain embodiments may be heterogeneous (e.g., heterostructures). Optionally, a nanocrystal may comprise one or more surface ligands (e.g., surfactants). The nanocrystal is optionally substantially single crystal in structure (a "single crystal nanostructure" or a "monocrystalline nanostructure"). Nanostructures may be fabricated from essentially any convenient material or material, the nanostructure may be prepared from an inorganic material, e.g., an inorganic conductive or semiconductive material. A conductive or semi-conductive nanostructure often displays 1-dimensional quantum confinement, e.g., an electron may often travel along only one dimension of the structure. Nanocrystals may be substantially homogeneous in material properties, or in certain embodiments may be heterogeneous (e.g., heterostructures). The term "nanocrystal" is intended to encompass substantially monocrystalline nanostructures comprising various defects, stacking faults, atomic substitutions, etc., as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be. The nanocrystals may be fabricated from essentially any convenient material or materials.

The terms "nanostructure" or "nanoparticle" are used herein to generally refer to a structure having at least one region or characteristic dimension with a dimension of less than about 500 nm, e.g., less than about 200 nm, less than about 100 nm, less than about 50 nm, or even less than about 20 nm. The region or characteristic dimension may be along the smallest axis of the structure. Examples of such structures include nanowires, nanorods, nanotubes, branched nanocrystals, nanotetrapods, tripods, bipods, nanocrystals, nanodots, quantum dots, nanoparticles, branched tetrapods (e.g., inorganic dendrimers), etc. Nanostructures may be substantially homogeneous in material properties, or in certain embodiments may be heterogeneous (e.g., heterostructures). Nanostructures may be, e.g., substantially crystalline, substantially monocrystalline, polycrystalline, amorphous, or a combination thereof. In one aspect, each of the three dimensions of the nanostructure has a dimension of less than about 500 nm, e.g., less than about 200 nm, less than about 100 nm, less than about 50 nm, or even less than about 20 nm. Nanostructures may comprise one or more surface ligands (e.g., surfactants).

The term "nonsystemic" as used herein, generally refers to a compound or composition which is not substantially absorbable into the bloodstream of a human or animal.

The terms "oligomeric" and "polymeric" as used herein are generally used interchangeably herein to generally refer to multimeric structures having more than one component monomer or subunit.

The term "organ" is used herein to generally refer to a part of the body of an animal or of a human generally refers to the collection of cells, tissues, connective tissues, fluids and structures that are part of a structure in an animal or a human that is capable of performing some specialized physiological function. Groups of organs constitute one or more specialized body systems. The specialized function performed by an organ is typically essential to the life or to the overall well-being of the animal or human. Non-limiting examples of body organs include the heart, lungs, kidney, ureter, urinary bladder, adrenal glands, pituitary gland, skin, prostate, uterus, reproductive organs (e.g., genitalia and accessory organs), liver, gall-bladder, brain, spinal cord, stomach, intestine, appendix, pancreas, lymph nodes, breast, salivary glands, lacrimal glands, eyes, spleen, thymus, bone marrow. Non-limiting examples of body systems include the respiratory, circulatory, cardiovascular, lymphatic, immune, musculoskeletal, nervous, digestive, endocrine, exocrine, hepato-biliary, reproductive, and urinary systems. In animals, the organs are generally made up of several tissues, one of which usually predominates, and determines the principal function of the organ.

The term "opthalmic" as used herein generally is of or relating to or resembling the eye; "ocular muscles"; "an ocular organ"; "ocular diseases".

The term "oral surface" as used herein generally refers to a portion of the mouth and/or something positioned in and/or coupled to a portion of the mouth. For example an oral surface may include, but is not limited to, at least a portion of a tooth, at least a portion of the gum, at least a portion of the tongue, at least a portion of a dental fixture (e.g., a filling, a bridge, a cap a false tooth).

The term "otic" as used herein generally is of, relating to, or located near the ear; auricular.

The term "pharmaceutically acceptable salts" as used herein generally includes salts prepared from by reacting pharmaceutically acceptable non-toxic bases or acids, including inorganic or organic bases, with inorganic or organic acids. Pharmaceutically acceptable salts may include salts derived from inorganic bases include aluminum, ammonium, calcium, copper, ferric, ferrous, lithium, magnesium, manganic salts, manganous, potassium, sodium, zinc, etc. Examples include the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-dibenzylethylenediamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, etc.

The term "pharmaceutically active agent" as used herein generally refers to a drug or other substance that has therapeutic value to a living organism including without limitation antithrombotics, anticoagulants, antiplatelet agents, thrombolytics, antiproliferatives, antiviral, antitumor, anticancer, antimicrobial, antifungal, anti-inflammatories, agents that inhibit restenosis, smooth muscle cell inhibitors, antibiotics, and the like, and mixtures thereof.

Terms such as "pharmaceutical composition," "pharmaceutical formulation," "pharmaceutical preparation," or the like, are used herein to generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

The term "pharmacologically inert," as used herein, generally refers to a compound, additive, binder, vehicle, and the like, that is substantially free of any pharmacologic or "drug-like" activity.

The term "polycyclic," as used herein, generally refers to a chemical compound having two or more atomic rings in a molecule. Steroids are polycyclic compounds.

The term "polymerizable compound," as used herein, generally refers to a chemical compound, substituent or moiety capable of undergoing a self-polymerization and/or co-polymerization reaction (e.g., vinyl derivatives, butadienes, trienes, tetraenes, dialkenes, acetylenes, diacetylenes, styrene derivatives).

By "prophylactically effective amount" is meant an amount of a pharmaceutical composition that will substantially prevent, delay or reduce the risk of occurrence of the biological or physiological event in a cell, a tissue, a system, animal or human that is being sought by a researcher, veterinarian, physician or other caregiver.

The term "quaternary ammonium moiety," as used herein, generally refers to a tetravalent charged nitrogen (e.g., $N^+R^3_4$).

The terms "R'''" in a chemical formula refer to a hydrogen or a functional group, each independently selected, unless stated otherwise. In some embodiments the functional group may be an organic group. In some embodiments the functional group may be an alkyl group. In some embodiment, the functional group may be a hydrophobic or hydrophilic group.

The terms "reducing," "inhibiting" and "ameliorating," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

The term "subject" as used herein generally refers to a human.

The term "sealant," as used herein, generally refers to any of various liquids, paints, chemicals, or soft substances that may be applied to a surface or circulated through a system of pipes or the like, drying to form a hard, substantially watertight coating. When used in the context of dentistry sealant generally refers to any of several transparent synthetic resins applied to the chewing surfaces of an oral cavity as a preventive measure against tooth decay in the occlusal pits and fissures.

The term "substituted alkyl" as used herein generally refers to an alkyl group with an additional group or groups attached to any carbon of the alkyl group. Substituent groups may include one or more functional groups such as alkyl, lower alkyl, aryl, acyl, halogen, alkylhalo, hydroxy, amino, alkoxy, alkylamino, acylamino, acyloxy, aryloxy, aryloxyalkyl, mercapto, both saturated and unsaturated cyclic hydrocarbons, heterocycles, and other organic groups.

The term "substituted alkyl-aryl" as used herein generally refers to an alkyl-aryl group with an additional group or groups attached to any carbon of the alkyl-aryl group. Additional groups may include one or more functional groups such as lower alkyl, aryl, acyl, halogen, alkylhalo, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), coupled covalently or coupled to a common group such as a methylene or ethylene group, or a carbonyl coupling group such as in cyclohexyl phenyl ketone, and others.

The term "substituted aryl" as used herein generally refers to an aryl group with an additional group or groups attached to any carbon of the aryl group. Additional groups may include one or more functional groups such as lower alkyl, aryl, acyl, halogen, alkylhalo, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), coupled covalently or coupled to a common group such as a methylene or ethylene group, or a carbonyl coupling group such as in cyclohexyl phenyl ketone, and others.

The term "substituted heterocycle" as used herein generally refers to a heterocyclic group with an additional group or groups attached to any element of the heterocyclic group. Additional groups may include one or more functional groups such as lower alkyl, aryl, acyl, halogen, alkylhalos, hydroxy, amino, alkoxy, alkylamino, acylamino, acyloxy, aryloxy, aryloxyalkyl, thioether, heterocycles, both saturated and unsaturated cyclic hydrocarbons which are fused to the heterocyclic ring(s), coupled covalently or coupled to a common group such as a methylene or ethylene group, or a carbonyl coupling group such as in cyclohexyl phenyl ketone, and others.

The term "substrate" as used herein generally refers to a body or base layer or material (e.g., onto which other layers are deposited).

The phrase "therapeutically effective amount" generally refers to an amount of a drug or pharmaceutical composition that will elicit at least one desired biological or physiological response of a cell, a tissue, a system, animal or human that is being sought by a researcher, veterinarian, physician or other caregiver.

The term "thioether" as used herein generally refers to the general structure R—S—R' in which R and R' are the same or different and may be alkyl, aryl or heterocyclic groups. The group —SH may also be referred to as "sulfhydryl" or "thiol" or "mercapto."

As used herein, the term "tissue", when used in reference to a part of a body or of an organ, generally refers to an aggregation or collection of morphologically similar cells and associated accessory and support cells and intercellular matter, including extracellular matrix material, vascular supply, and fluids, acting together to perform specific functions in the body. There are generally four basic types of tissue in animals and humans including muscle, nerve, epithelial, and connective tissues.

The term "topical" as used herein generally is of, pertaining to, or applied externally to a particular part of the body; local.

The term "virus" as used herein generally refers to an ultramicroscopic (20 to 300 nm in diameter), metabolically inert, infectious agent that replicates only within the cells of living hosts, mainly bacteria, plants, and animals: composed of an RNA or DNA core, a protein coat, and, in more complex types, a surrounding envelope.

Bridged Polycyclic Compounds

New antimicrobials are required to combat the new antimicrobial resistant microbes. New antimicrobials may be effective verses microbes which are currently resistant to currently known antimicrobials. New antimicrobials may resist leaching off into the environment beyond a predetermined amount to inhibit polluting the environment unnecessarily (which may concurrently increase the occurrence of antimicrobial resistant microbes from overexposure of antimicrobials).

One strategy for combating antimicrobial resistant organisms is by modifying known antimicrobials to increase their effectiveness. In some embodiments, quaternary ammonium compounds may be modified to increase their effectiveness. It is typically thought that quaternary ammonium compounds denature the proteins of the bacterial or fungal cell, affect the metabolic reactions of the cell and allow vital substances to leak out of the cell, finally causing death. In addition, quaternary ammonium compounds are not known to be toxic towards higher forms of life (e.g., humans).

One of the main considerations in examining the mode of action is the characterization of quaternary ammonium compounds as cationic surfactants. This class of chemical reduces the surface tension at interfaces, and is attracted to negatively charged surfaces, including microorganisms. Quaternary ammonium compounds denature the proteins of the bacterial or fungal cell, affect the metabolic reactions of the cell and allow vital substances to leak out of the cell, finally causing death.

Most uses of quaternary ammonium compounds as antimicrobials involve formulations of disinfectants and sanitizers which are not bound to a surface, resulting in effluent stream pollution and contamination. They are simply wetted onto the surface such as in disinfecting wipes which are primarily ammonium salts as their liquid active ingredient. When they are incorporated into surfaces they are not crosslinked but are allowed to float to the surface thereby becoming depleted over time the same way silver and triclosan are incorporated in plastics. Coupling quaternary ammonium compounds to a surface or formation within a polymer matrix may inherently reduce the effectiveness of the quaternary ammonium compounds, by decreasing the accessibility of microbes to the most active cationic portion of the molecule. Increasing accessibility to the quaternary ammonium compounds within a surface coating or with any use increases the effectiveness of the quaternary ammonium compound.

In some embodiments, the effectiveness of an antimicrobial (e.g., quaternary ammonium compound) may be increased by coupling the antimicrobial within or on a curved surface, where the curved surface is on a molecular scale. For example, a curved surface may be created using nanoparticles (e.g., spherical nanoparticles). Nanoparticles may incorporate into their structure antimicrobial compounds with greater exposed surface area due to the curved surface of the nanoparticle.

In some embodiments, a compound may include a nanoparticle. The nanoparticle may include a bridged polycyclic compound. A compound may be formed using self-assembly techniques and principles. A compound may be formed from portions which are themselves antimicrobial (e.g., quaternary ammonium compounds). A compound may bind moieties to at least portions of itself which have, for example, antimicrobial properties.

In some embodiments, a protective coating composition may include a compound. A compound may be a bridged polycyclic compound. A bridged polycyclic compound may be a cavitand. Portions of the bridged polycyclic compound may include two or more quaternary ammonium moieties. The protective coating composition may be antimicrobial.

New carrier agents are required to more effectively deliver existing and future pharmaceutical agents.

One strategy for more effectively delivering pharmaceutical agents is to couple a multitude of pharmaceutical agents (e.g., a single type of agent or a combination of different agents) to a single molecular entity.

In some embodiments, the effectiveness of a pharmaceutically active agent may be increased by coupling the agent within or on a curved surface, where the curved surface is on a molecular scale. For example, a curved surface may be created using nanoparticles (e.g., spherical nanoparticles). Nanoparticles may incorporate into their structure pharmaceutically active agent with greater exposed surface area due to the curved surface of the nanoparticle.

In some embodiments, a pharmaceutically active agent may include using derivatives of pharmaceutically active agents. Pharmaceutically active agents may be modified in order to couple the agent to one or more bridged polycyclic compounds. Pharmaceutically active agents may be modified in order to increase their effectiveness.

In some embodiments, a compound may include a nanoparticle. The nanoparticle may include a bridged polycyclic compound. A compound may be formed using self-assembly techniques and principles. A compound may be formed from portions which are pharmaceutically active agents. A compound may bind moieties to at least portions of itself which are pharmaceutically active agents.

In some embodiments, a composition may include one or more bridged polycyclic compounds. At least one of the bridged polycyclic compounds may include at least two cyclic groups. A general example of a bridged polycyclic compound including only two cyclic groups may include, but is not limited to, a compound 100 having a general structure

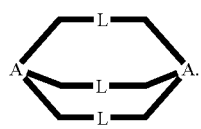

In some embodiments, at least two cyclic groups may be defined in part by quaternary ammonium moieties, by the nitrogen of the quaternary ammonium moiety comprising one of the atoms which forms a part of the cyclic structure itself. For example, a cyclic structure which is formed at least in part by a quaternary ammonium moiety may include, but is not limited to structure 101

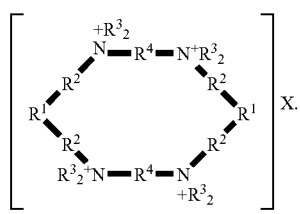

Structure 101 is an example of quaternary ammonium moieties defining at least in part a cyclic group, however, compound 101 is not an example of a polycyclic compound and compound 101 is not an example of a bridged polycyclic compound.

In some embodiments, a bridged polycyclic compound may include at least two quaternary ammonium moieties, at least three quaternary ammonium moieties, at least four quaternary ammonium moieties, at least five quaternary ammonium moieties, at least six quaternary ammonium moieties, at least seven quaternary ammonium moieties, or at least eight quaternary ammonium moieties.

In some embodiments, a compound 100 may have a general structure

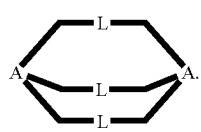

Compound 100 may be formed by coupling a trifunctional corner unit A with a bifunctional linker unit L as depicted in Scheme 2.

Scheme 2. Schematic depiction of the formation of compound 100.

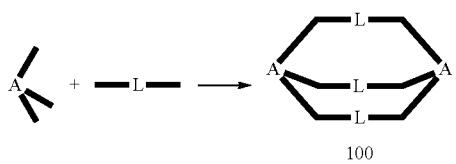

Scheme 2 should not be used to limit the disclosure set forth herein. Corner unit A may include multiple dentate linkers other than the one depicted in Scheme 2 (e.g., a trifunctional linker A is depicted in Scheme 2) including, but not limited to, bifunctional, tetrafunctional (e.g., compound 100a) etc. In some embodiments, a corner unit A may be coupled to a linker unit L in any multitude of ways known to one skilled in the art.

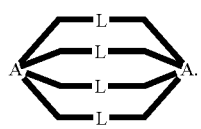

In some embodiments, a compound 100c may have a general structure

Compound 100c may be a bridged polycyclic compound. In some embodiments, Z may include at least one bridge. Bridge Z may couple 2 non adjacent atoms.

In some embodiments, at least one of the bridges is —$R^2$—$N^+R^3{}_2$—$R^4$—$N^+R^3{}_2$—$R^2$—, such that each bridge independently couples A to A. In some embodiments, at least one of the bridges may be —$R^2$—$NR^3$—$R^4$—$N^+R^3{}_2$—$R^2$—. Each bridge may independently couple A to A. In some embodiments, at least one of the bridges may be —$R^2$—$NR^3$—$R^4$—$NR^3$—$R^2$—. Each bridge may independently couple A to A. In some embodiments, at least one of the bridges may be —$R^2$—N=$R^4$=N—$R^2$—. Each bridge may independently couple A to A.

For example when Z is 1 compound 100c may be a compound 100 having a general structure

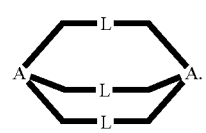

When, for example, Z is 2a compound 100c may be a compound 100a having a general structure

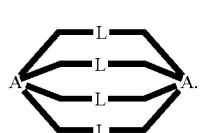

When, for example, Z is 3a compound 100c may be a compound 100d having a general structure

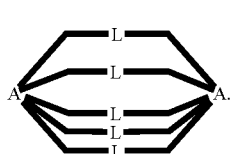

In some embodiments, a compound may include a bridged polycyclic compound formed from two corner units (e.g., compound 100b). Compound 100b may be formed by coupling a multifunctional (e.g., trifunctional) corner unit A with a second multifunctional (e.g., trifunctional) corner unit A as depicted in Scheme 2a.

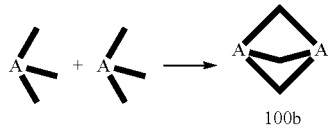

100b

Scheme 2a. Schematic depiction of the formation of compound 100b.

In some embodiments, a compound 102 may have a general structure

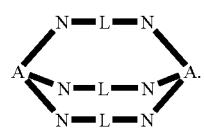

102

Compound 102 may include a moiety coupling corner unit A with linker unit L, the moiety including a nitrogen.

In some embodiments, a compound 103 may have a general structure

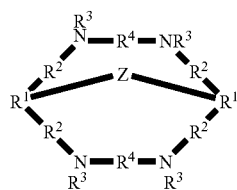

(103a)

In some embodiments, $R^1$ may be independently alkyl, substituted alkyl, aryl, substituted aryl, N, $N^+R^3$, heterocycle, or substituted heterocycle. $R^2$ may be independently alkyl, substituted alkyl, aryl, substituted aryl, heterocycle, substituted heterocycle, covalent bond, or alkene. $R^3$ may be independently a pharmaceutically active agent, alkyl, substituted alkyl, aryl, substituted aryl, heterocycle, substituted heterocycle, alkene, ether, PEG, contains boron, or PEI. $R^4$ may be independently alkyl, substituted alkyl, aryl, substituted aryl, $N^+R^3$, heterocycle, substituted heterocycle, alkyl ether, PEG, PEI, ether, or alkene. $R^4$ may independently include amide, alcohol, ester, sulfonamide, or sulfanilamide. $R^4$ may be independently alkyl, substituted alkyl, aryl, substituted aryl, heterocycle, substituted heterocycle, ether, amide, alcohol, ester, sulfonamide, sulfanilamide, or alkene. Z may include at least one bridge.

In some embodiments, at least one of the bridges may be —$R^2$—$N^+R^3{}_2$—$R^4$—$N^+R^3{}_2$—$R^2$—. Each bridge may independently couple $R^1$ to $R^1$. In some embodiments, at least one of the bridges may be —$R^2$— $NR^3$— $R^4$—$N^+R^3{}_2$—$R^2$—. Each bridge may independently couple $R^1$ to $R^1$.

In some embodiments, at least one of the bridges may be —$R^2$—$NR^3$—$R^4$—$NR^3$—$R^2$—. Each bridge may independently couple $R^1$ to $R^1$. In some embodiments, at least one of the bridges may be —$R^2$—N=$R^4$=N—$R^2$—. Each bridge may independently couple $R^1$ to $R^1$.

For example when Z is 1 compound 103a may be a compound 104b having a general structure

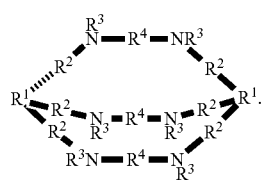

104b

When, for example, Z is 2a compound 103a may be a compound 104c having a general structure

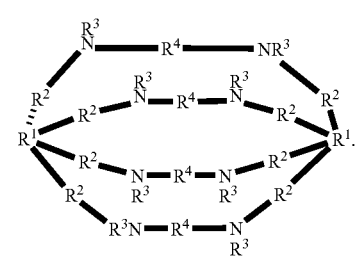

104c

In some embodiments, a pharmaceutically active agent may include guanidine or a derivative of guanidine. Chlorhexidine is a chemical antiseptic. Chlorhexidine functions as a bactericidal to both gram-positive and gram-negative microbes. It is considered less effective with some gram-negative microbes. Chlorhexidine is considered bacteriostatic. The mechanism of action is believed to be membrane disruption, in a similar manner to the quaternary ammonium salts discussed herein. A known guanidine is Chlorhexidine having a structure

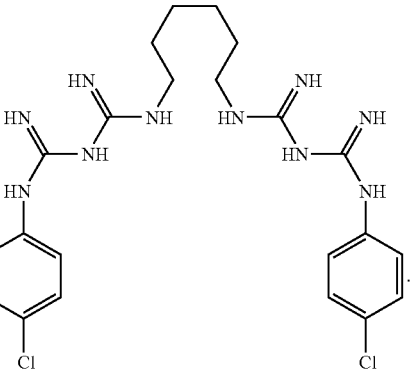

In some embodiments, a guanidine derivative may include a moiety having a structure (including a salt of the moiety)

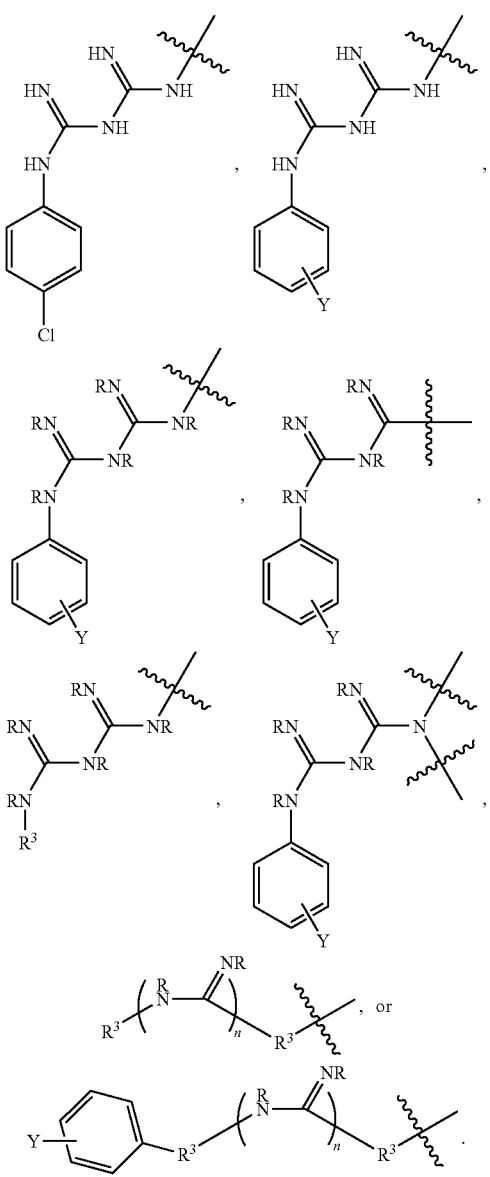

In some embodiments, a guanidine derivative may include a moiety having a structure (including a salt of the structures)

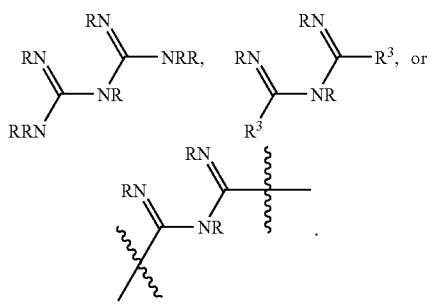

In some embodiments, a guanidine derivative may include an amidine moiety.

In some embodiments, a pharmaceutically active agent may include an anti-viral agent.

In some embodiments, a pharmaceutically active agent may include an anti-inflammatory agent.

In some embodiments, a pharmaceutically active agent may include an antigen blocking agent.

In some embodiments, a pharmaceutically active agent may include an allergen blocking agent.

In some embodiments, a pharmaceutically active agent may include an osteoblast stimulating agent.

In some embodiments, a pharmaceutically active agent may include an osteoclast inhibiting agent.

In some embodiments, a pharmaceutically active agent may include a periodontal bacteria attachment inhibitor In some embodiments, a pharmaceutically active agent may include a periodontal disease enzyme inhibitor.

In some embodiments, a pharmaceutically active agent may include a periodontal disease enzyme attachment inhibitor.

In some embodiments, a pharmaceutically active agent may include a periodontal disease agent.

In some embodiments, a pharmaceutically active agent may include a topical agent.

In some embodiments, a pharmaceutically active agent may include an antifungal agent.

In some embodiments, a pharmaceutically active agent may include antimicrobial agents.

In some embodiments, an example of a compound 104b may include compounds having a general structure:

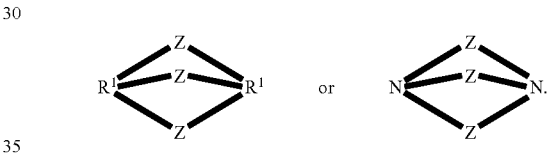

Z may include

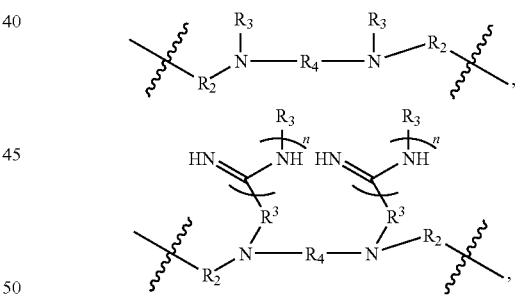

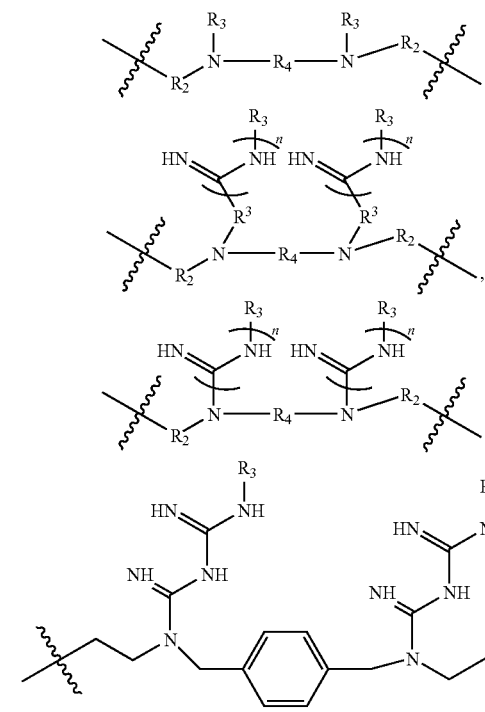

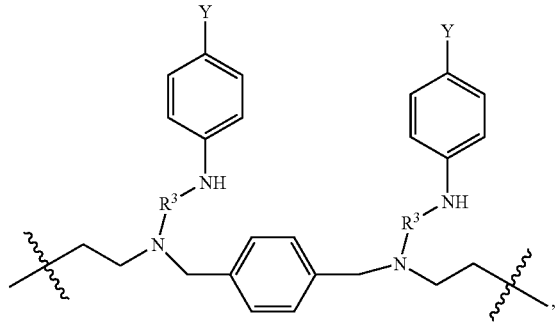
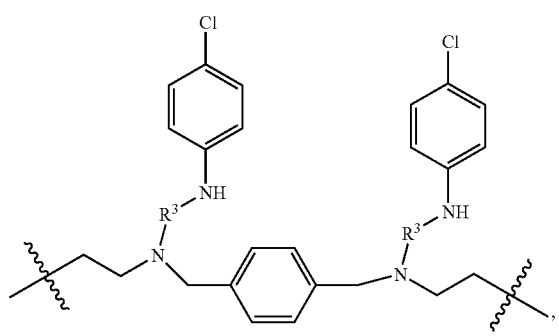
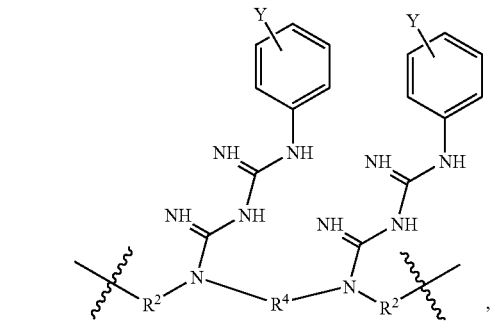
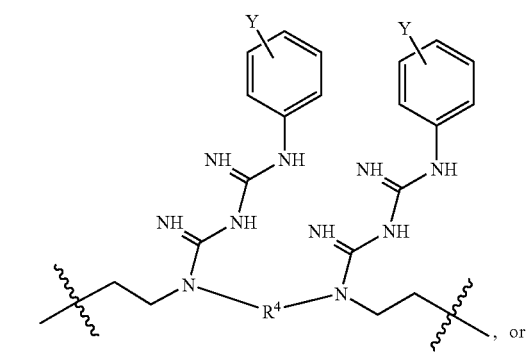
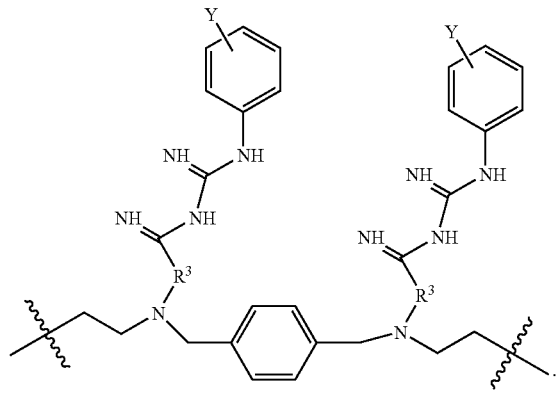
In some embodiments, Z may include at least two bridges.
In some embodiments, a chemical composition may include a chemical compound, wherein the chemical compound has a general structure:
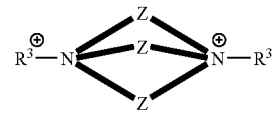
including combinations of Z, X and/or NaOAc as $R^3$ or
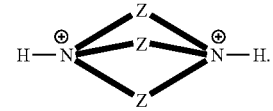
Z may include
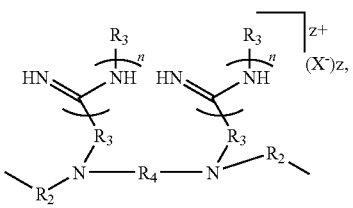
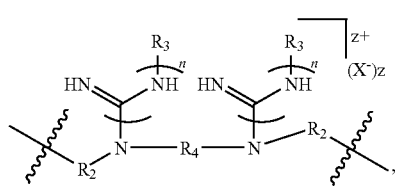

37
-continued
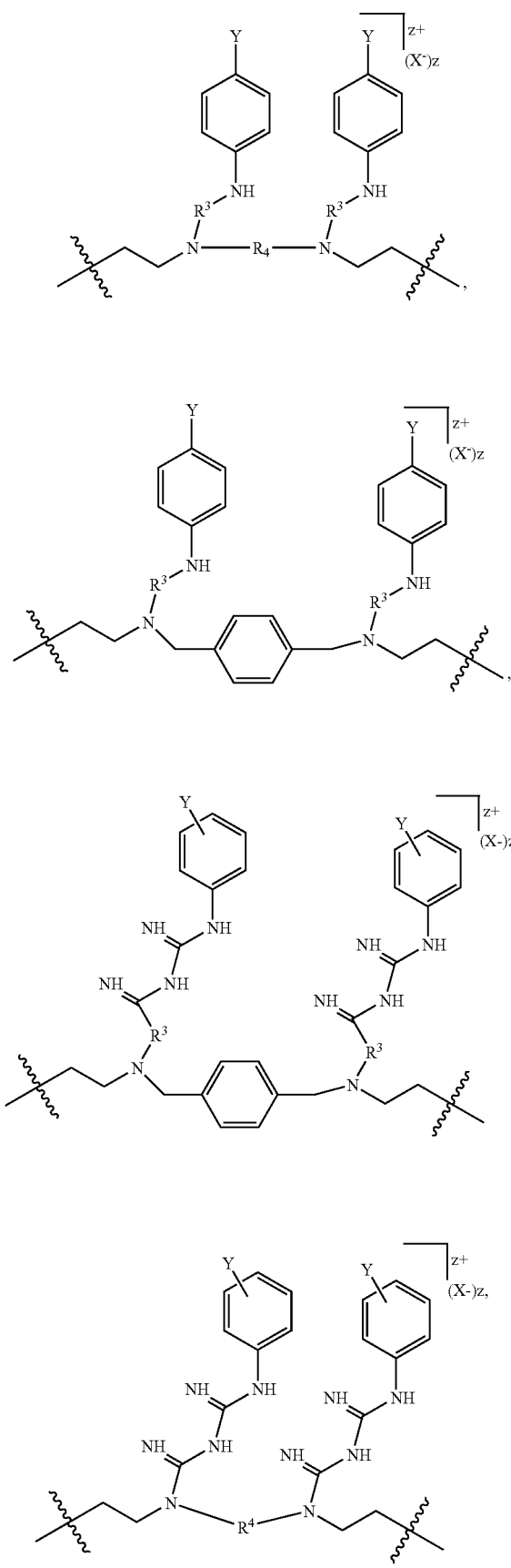
38
-continued
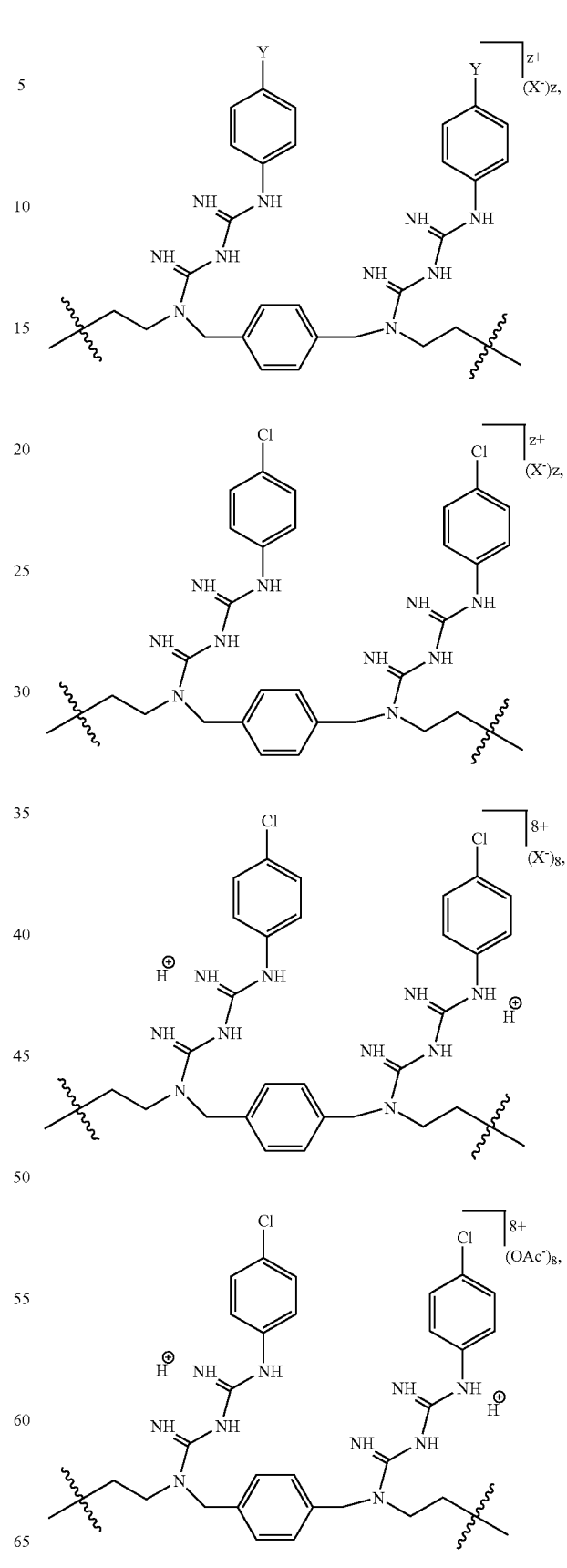

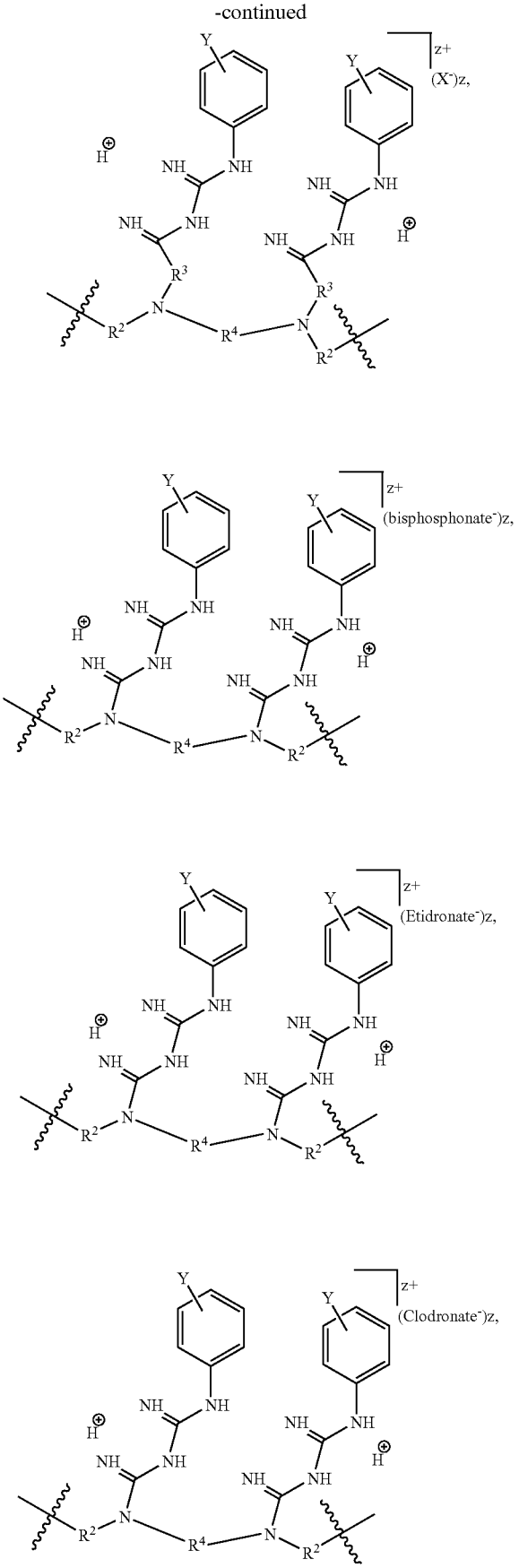
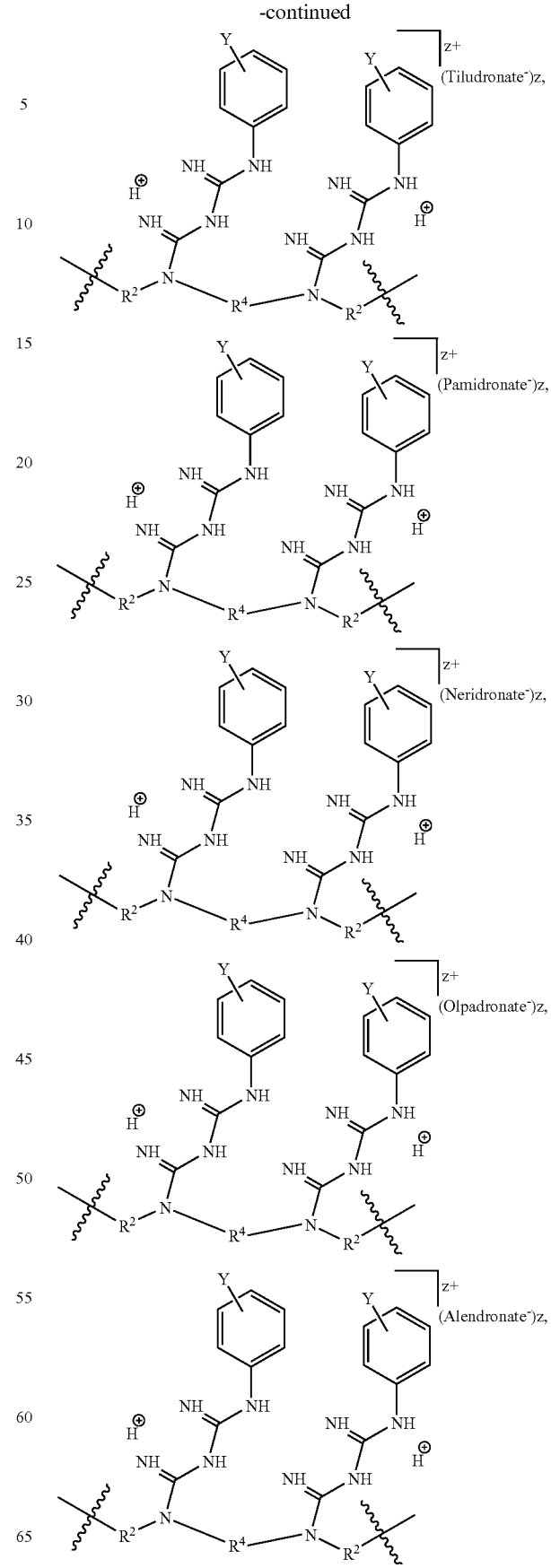

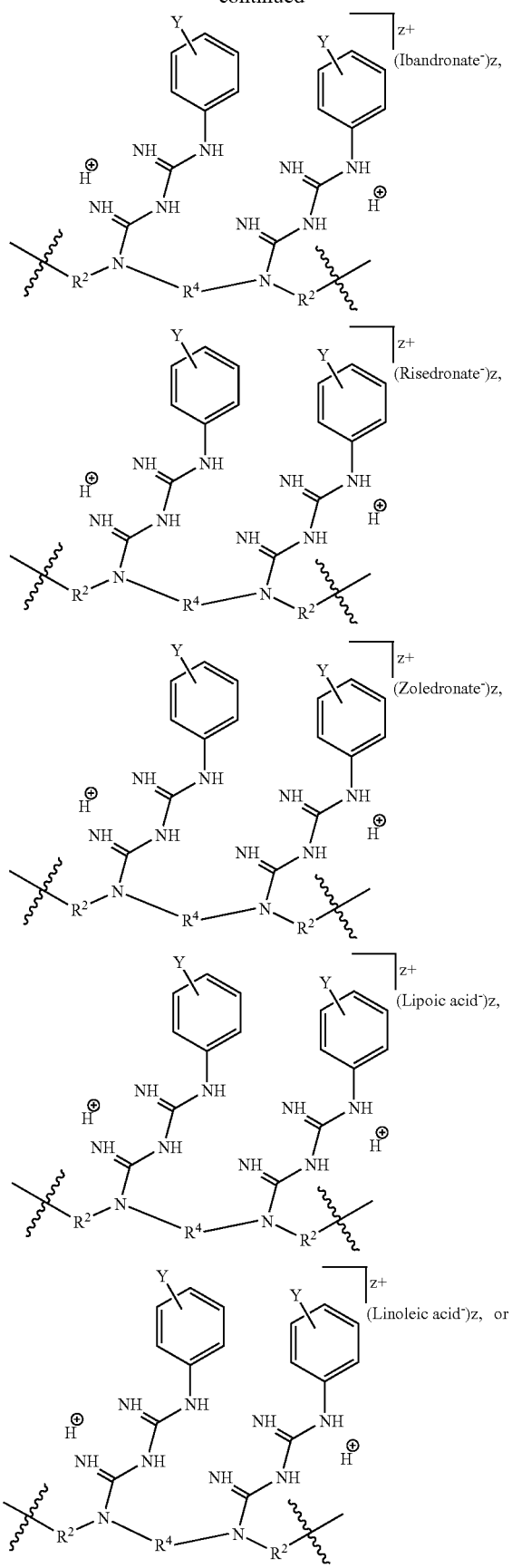

(Ibandronate⁻)z, (Risedronate⁻)z, (Zoledronate⁻)z, (Lipoic acid⁻)z, (Linoleic acid⁻)z, or

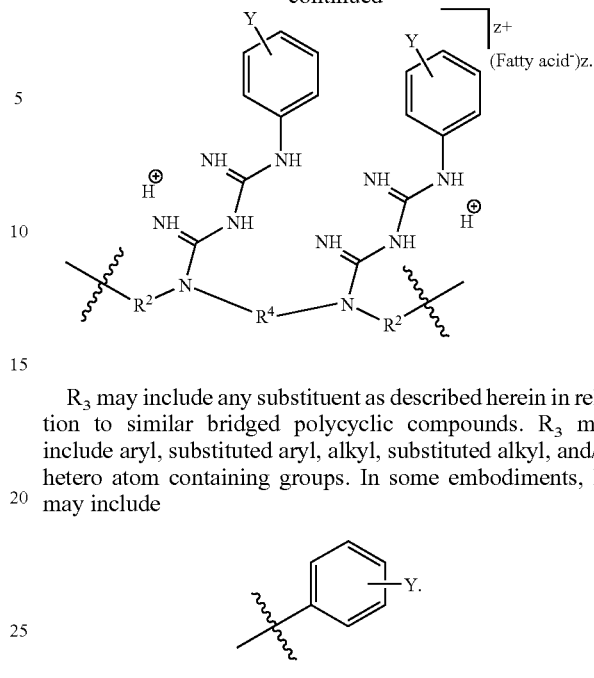

(Fatty acid⁻)z.

$R_3$ may include any substituent as described herein in relation to similar bridged polycyclic compounds. $R_3$ may include aryl, substituted aryl, alkyl, substituted alkyl, and/or hetero atom containing groups. In some embodiments, $R_3$ may include

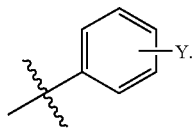

Y may include, for example a halogen (e.g., Cl). Y may include aryl, substituted aryl, alkyl, and/or substituted alkyl. In some embodiments, $R_3$ may include

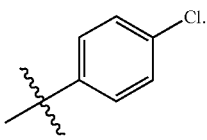

In some embodiments, bridged polycyclic compounds may inhibit bone resorption by adding bisphosphonate counterions. Etidronic acid may be used as a counterion. In some embodiments, a bisphosphonate may include Etidronate, Clodronate, Tiludronate, Pamidronate, Neridronate, Olpadronate, Alendronate, Ibandronate, Risedronate, or Zoledronate. In some embodiments, a counterion may include a derivative of Linoleic acid, fatty acid, or Lipoic acid In some embodiments, $R_3$ may include a guanidine moiety and/or a substituted guanidine moiety. In some embodiments, $R_3$ may include a halogenated aryl group (e.g., (e.g., 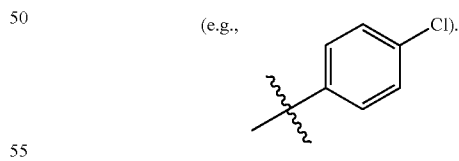 Cl).

n may range from 1-10, 2-8, 2-4, 3-6, 2-3, or 1-3. In some embodiment, n may be 2. In some embodiments, a z may represent a charge on the chemical compound and an appropriate number of counterions. z may range from 1-16, 2-14, 6-14, or 8-14. In some embodiments, y may represent a number of bridges coupling the Nitrogens of the chemical compound. y may range from 3-8, 3-5, or 3-4.

In some embodiments, compounds such as 104b (e.g., 10-24) may include salts of the compounds. Salts may include organic and/or inorganic counterions. Counterions may include a singly or a multiply charged ion. Counterions may include a singly or a monomer or a polymer ion. Counterions may include an acetate ion, a carbohydrate ion, a saccharide ion, or a sugar ion.

Counterions may include any of the examples described herein. In some embodiments, a salt of 104b (e.g., 10-24) may include an acetate counterion. A salt of 104b (e.g., 10-24) may include a charge from 1-20, 1-14, 4-14, 6-14, 4-10, or 4-8.

In some embodiments, a compound 103 may have a general structure

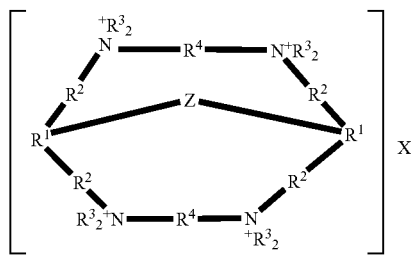

(103)

In some embodiments, $R^1$ may be independently alkyl, substituted alkyl, aryl, substituted aryl, N, $N^+R^3$, heterocycle, or substituted heterocycle. $R^2$ may be independently alkyl, substituted alkyl, aryl, substituted aryl, heterocycle, substituted heterocycle, covalent bond, or alkene. $R^3$ may be independently a pharmaceutically active agent, alkyl, substituted alkyl, aryl, substituted aryl, heterocycle, substituted heterocycle, alkene, ether, PEG, or PEI. $R^4$ may be independently alkyl, substituted alkyl, aryl, substituted aryl, $N^+R^3$, heterocycle, substituted heterocycle, alkyl ether, PEG, PEI, ether, contains boron, or alkene. $R^4$ may independently include amide, alcohol, ester, sulfonamide, or sulfanilamide. $R^4$ may be independently alkyl, substituted alkyl, aryl, substituted aryl, heterocycle, substituted heterocycle, ether, amide, alcohol, ester, sulfonamide, sulfanilamide, or alkene. X may be one or more counterions. Z may include at least one bridge.

In some embodiments, at least one of the bridges may be —$R^2$—$N^+R^3{}_2$—$R^4$—$N^+R^3{}_2$—$R^2$—. Each bridge may independently couple $R^1$ to $R^1$. In some embodiments, at least one of the bridges may be —$R^2$—$NR^3$— $R^4$—$N^+R^3{}_2$—$R^2$—. Each bridge may independently couple $R^1$ to $R^1$. In some embodiments, at least one of the bridges may be —$R^2$—$NR^3$—$R^4$—$NR^3$—$R^2$—. Each bridge may independently couple $R^1$ to $R^1$. In some embodiments, at least one of the bridges may be —$R^2$—N=$R^4$=N—$R^2$—. Each bridge may independently couple $R^1$ to $R^1$.

For example when Z is 1 compound 103 may be a compound 104 having a general structure

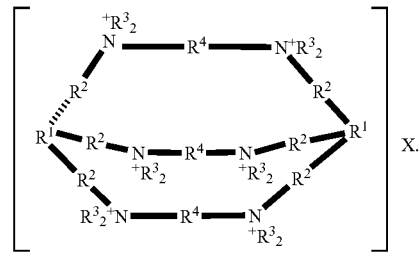

104

When, for example, Z is 2a compound 103 may be a compound 104a having a general structure

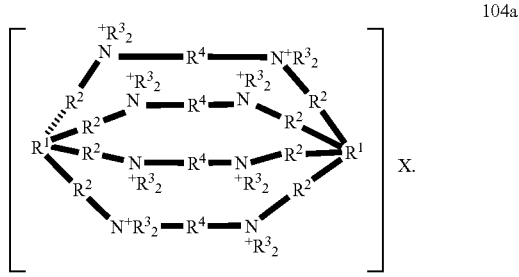

104a

In some embodiments, a compound 104 may have a general structure

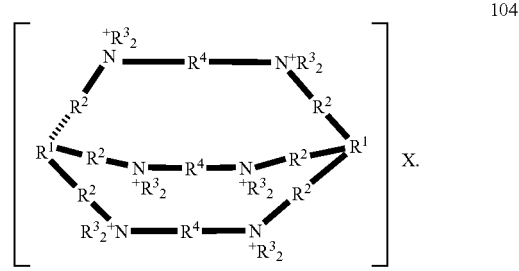

104

In some embodiments, $R^1$ may be alkyl, substituted alkyl, aryl, substituted aryl, $N^+R^3$, heterocycle, or substituted heterocycle. $R^2$ may be alkyl, substituted alkyl, aryl, substituted aryl, $N^+R^3$, heterocycle, substituted heterocycle, covalent bond, or alkene. $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, $N^+R^3$, heterocycle, substituted heterocycle, alkyl ether, PEG, PEI, ether, or alkene. $R^4$ may include amide, alcohol, ester, sulfonamide, or sulfanilamide. X may be one or more counterions.

In some embodiments, counterions may include one or more halogens (e.g., Br, Cl, I, etc.). A specific embodiment of a halogen counterion may include Iodine which has proven as a more effective counterion for antimicrobial compounds. As has been discussed herein, counterions may affect the properties of the chemical compound and subsequent composition. Boron based counterions may increase certain antimicrobial properties (e.g., $BF_4^-$).

In some embodiments, salts of specific counterions may be added to a pharmaceutical composition to increase the effectiveness of the composition. For example, any of the counterions described herein for use in making the bridged polycyclic compound (e.g., counterions which increase a pharmaceutically active agent's effectiveness of the compound), may be added to the composition later (e.g., as a salt such as sodium or potassium tetrafluoroborate). In some embodiments, a combination of the two strategies may be used, additionally allowing for two or more different counterions or salts to be included in the final formulation of the composition. Each of the counterions and/or salts may increase the effectiveness of the composition in a different manner. Other examples of counterions (which may be added as an appropriate salt later in an ion exchange or a desired salt may be used during synthesis of the bridged polycyclic compound) may include an anion, a polymer, a monomer, a halogen, an iodine, a bromine, a chlorine, a triflate, a tosylate, a boron, a borate, tetrafluoroborate, a nitrogen containing gourp, a nitrate, a halogen, a hexafluorophosphate, an acetate, or an NTf$_2$ (wherein Tf is bis(trifluoromethanesulfonyl) imide).

In some embodiments, a compound may include one or more guest molecules coupled to the compound such as compound 106 having a general structure

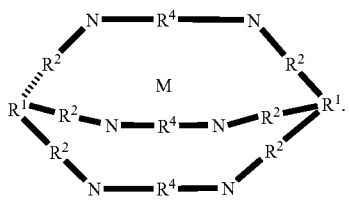

In some embodiments, $R^1$ may be alkyl, substituted alkyl, aryl, substituted aryl, N,N$^+$R$^3$, heterocycle, or substituted heterocycle. $R^2$ may be alkyl, substituted alkyl, aryl, substituted aryl, N$^+$R$^3$, heterocycle, substituted heterocycle, covalent bond, or alkene. $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, N$^+$R$^3$, heterocycle, substituted heterocycle, alkyl ether, PEG, PEI, ether, or alkene. M may include one or more guest molecules associated with one or more portions of compound 107 (e.g., amines). M may be one or more metals. M may include silver, zinc, copper, gold, calcium, nickel, cobalt, barium, strontium, lead, lanthanum, iron, manganese, cadmium, magnesium, yttrium, lanthanum, cesium, praseodymium, neodymium, europium, gadolinium, terbium, dysprosium, holmium, erbium, thulium, ytterbium, or alkaline earth metals or cesium. In some embodiments, M may include organic cation salts as templates (e.g., trimethyl ammonium, etc.). M may include light activated elements such that an antiviral or anticancer property of M is increased. X may be one or more counterions.

In some embodiments, M may be one or more guest molecules. X may be one or more counterions. M (e.g., Ag+ counterion) may bind thereby keeping M in close proximity (e.g., F-ions have been reported and verified by x-ray single crystal structure to bind in ammonium salt cavitands). An anion may bind to an ammonium thus affording a close association of the cation counterion. In some embodiments, M may pi-bond coordinate to R$_4$ (e.g., aryl) or a heterocycle binding (e.g., pyridiyl R$_4$ nitrogen to a Ag+ or a phenol —OH or O— binding to the Ag+).

In some embodiments, M may be two silver metals associated with compound 107 forming a compound 107a having the general structure

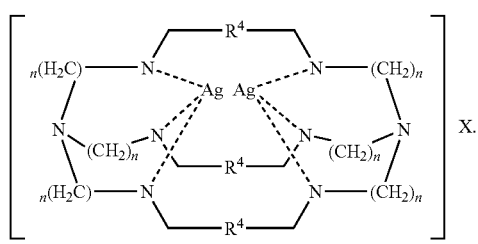

In some embodiments, a compound may include one or more guest molecules coupled to the compound such as compound 108 having a general structure

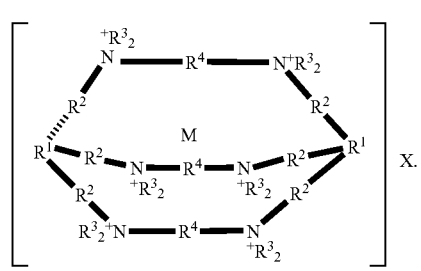

In some embodiments, $R^1$ may be alkyl, substituted alkyl, aryl, substituted aryl, N$^+$R$^3$, heterocycle, or substituted heterocycle. $R^2$ may be alkyl, substituted alkyl, aryl, substituted aryl, N$^+$R$^3$, heterocycle, substituted heterocycle, covalent bond, or alkene. $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, N$^+$R$^3$, heterocycle, substituted heterocycle, alkyl ether, PEG, PEI, ether, or alkene. M may be one or more metals. M may include silver, zinc, copper, gold, calcium, nickel, cobalt, barium, strontium, lead, lanthanum, iron, manganese, cadmium, magnesium, yttrium, lanthanum, cesium, praseodymium, neodymium, europium, gadolinium, terbium, dysprosium, holmium, erbium, thulium, ytterbium, or alkaline earth metals or cesium. In some embodiments, M may include organic cation salts as templates (e.g., trimethyl ammonium, etc.). M may include light activated elements such that an antiviral and/or anticancer property of M is increased. X may be one or more counterions.

It should be understood that any of the compounds depicted herein may or may not have one or more metals coupled to the structure. For example, a structure depicted with a metal associated with the compound also includes a compound without a metal associated with the compound. A structure depicted without a metal associated with the compound also includes a compound with a metal associated with the compound. Although in many instances metals depicted herein are shown positioned within a space defined by compounds described herein, this should not be seen as limiting, metals may be coupled (e.g., complexed to) to a compound along an outer surface of the compound.

Metals may include any elements in the periodic chart designated as metals, known to one skilled in the art. In some embodiments, metals may include any cationic metal known to one skilled in the art (e.g., Zn, Cu, Au, Ag, Cs, Mn, Mg, Ca, Ni, Co, etc.). In some embodiments, metals may include metals which have antiviral and/or anticancer properties and/or anti-inflammatory properties (e.g., Ag, Zn, etc.). In some embodiments, metals may function to couple one or more atoms or molecules within a compound (e.g., compound 108) and/or to the surface of the compound. In some embodiments, one or more metals coupled to a compound may include one or more inorganic/organometallic compounds. A compound (e.g., a bridged polycyclic compound) may include two or more different metals coupled (e.g., associated in some way) to the compound. In some embodiments, a metal may be coupled to a bridged polycyclic molecule.

In some embodiments, $R^1$ may be N$^+$(1-22C alkyl), N$^+$(1-12C alkyl), N$^+$(1-6C alkyl), N$^+$(6C alkyl), N$^+$R$^3$,

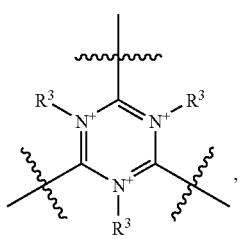

cyclam, aza crown ether, tris ethylamine N substituted cyclam, or

In some embodiments, $R^2$ may be 1-2C alkyl, 1-6C alkyl, 2-4C alkyl, $CH_2$, or a bond (e.g., covalent, ionic) between $R^1$ and a N of, for example, compound 108.

In some embodiments, $R^3$ may be hydrophobic or hydrophilic. $R^3$ may be 1-3C alkyl, 4-5C alkyl, 6-10C alkyl, 7-9C alkyl, 10-22C alkyl, 15-22C alkyl, 6-10C alkyl ether, 7-9C alkyl ether, methyl, PEI (polyethyleneimine), or PEG (polyethyleneglycol). $R^3$ may be 6C alkyl. $R^3$ may be a polymer. $R^3$ may be an oxazoline polymer.

In some embodiments, $R^4$ may include alkyl or substituted alkyl.

In some embodiments, $R^4$ may be an aryl, substituted aryl, heterocycle, or substituted heterocycle. $R^4$ may be

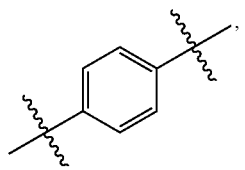 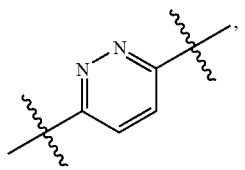

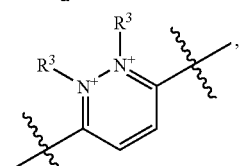 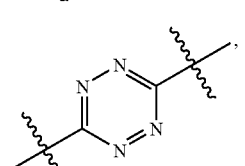

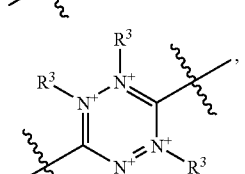 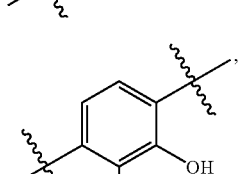

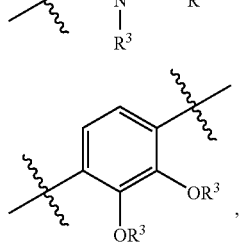 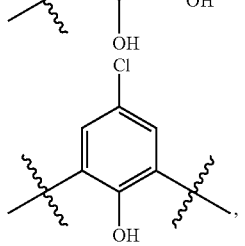

-continued

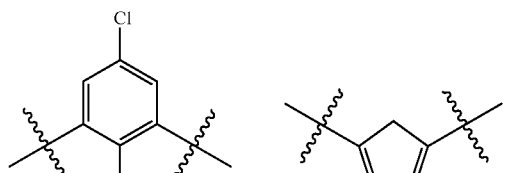 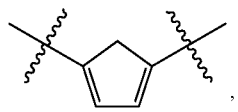

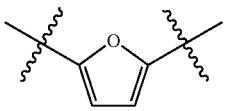

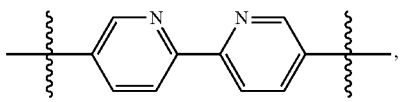

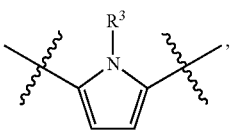 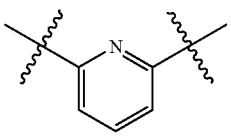

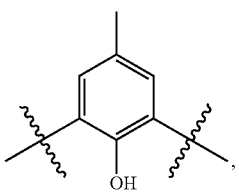 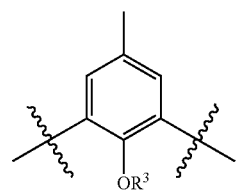

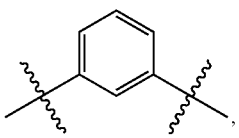 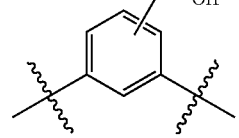

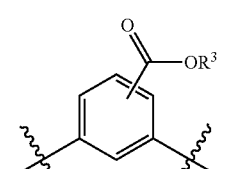 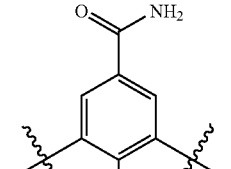

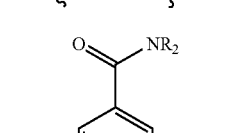 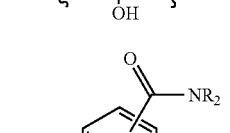

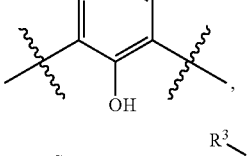 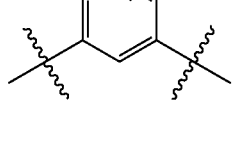

 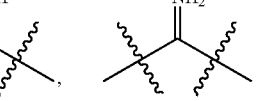

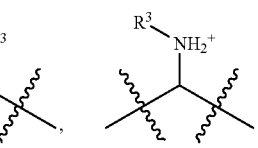

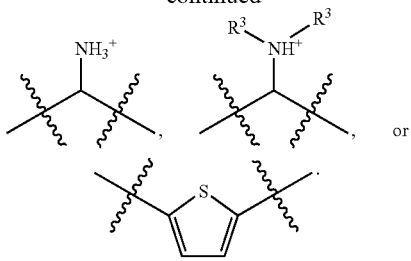

Forming one or more portions of a compound from one or more aromatic rings may provide advantages. Advantages may include providing rigidity to the compound enhancing the stability of the compound. Aromatic rings may facilitate the self-assembly of the constituent parts of the compound. Other advantages may include pie stacking of compounds relative to one another or of "guests" positioned within the compound. A substituted aryl or heterocycle may include moieties (e.g., N) which bind to other elements (e.g., metals such as silver) or molecules. $R^4$ may include substituents (e.g., $R^3$) which effect properties of a compound as a whole (e.g., hydrophobicity, hydrophilicity, self-cleaning, antimicrobial, cross-coupling properties).

In some embodiments, a compound 108 may include an embodiment such as compound 110 having a general structure

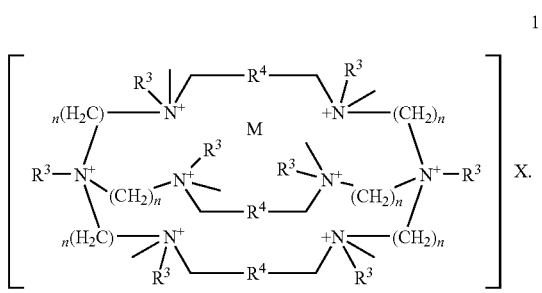

In some embodiments, $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, $N^+R^3$, heterocycle, substituted heterocycle, alkyl ether, PEG, PEI, ether, or alkene. M may include one or more "guest" molecules (e.g., one or more metals). X may be one or more counterions.

In some embodiments, a compound 104 may include an embodiment such as compound 111 having a general structure

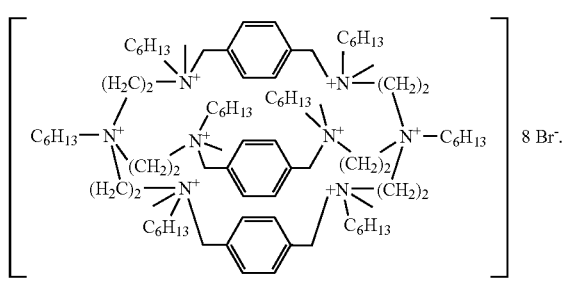

In some embodiments, a compound 104 may include any number of combination of embodiments such as compound 113 having a general structure

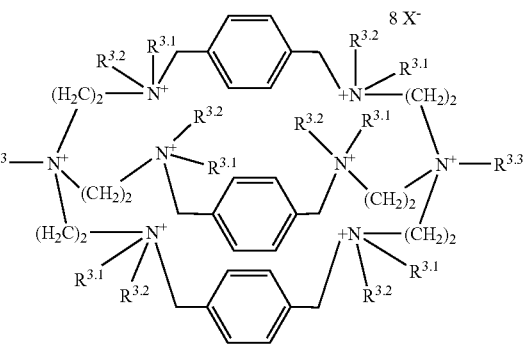

where:
113a is $R^{3.1}$=$C_6H_{13}$, $R^{3.2}$=$CH_3$ and $R^{3.3}$=$R^{3.1}$ or $R^{3.2}$
113b is $R^{3.1}$=$C_8H_{17}$, $R^{3.2}$=$CH_3$ and $R^{3.3}$=$R^{3.1}$ or $R^{3.2}$
113c is $R^{3.1}$=$C_{10}H_{21}$, $R^{3.2}$=$CH_3$ and $R^{3.3}$=$R^{3.1}$ or $R^{3.2}$
113d is $R^{3.1}$=$C_{12}H_{25}$, $R^{3.2}$=$CH_3$ and $R^{3.3}$=$R^{3.1}$ or $R^{3.2}$
113e is $R^{3.1}$=$C_6H_{13}$, $R^{3.2}$=$CH_2Ph$ and $R^{3.3}$=$R^{3.1}$ or $R^{3.2}$
113f is $R^{3.1}$=$C_{12}H_{25}$, $R^{3.2}$=$CH_2Ph$ and $R^{3.3}$=$R^{3.1}$ or $R^{3.2}$
113h is $R^{3.1}$=$C_4H_9$, $R^{3.2}$=$CH_3$ and $R^{3.3}$=$R^{3.1}$ or $R^{3.2}$ In some embodiments, a compound 104 may include a an embodiment such as compound 114 having a general structure

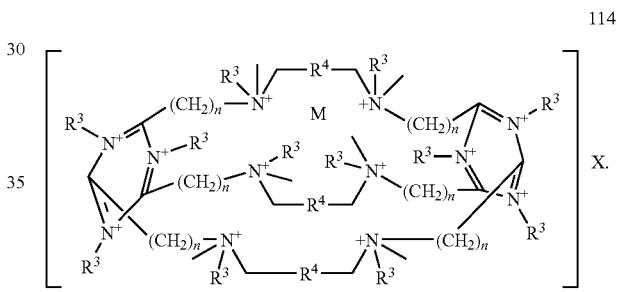

In some embodiments, $R^3$ may be alkyl, substituted alkyl, aryl, substituted aryl, heterocycle, substituted heterocycle, alkyl ether, PEG, PEI, or alkene. $R^4$ may be alkyl, substituted alkyl, aryl, substituted aryl, $N^+R^3$, heterocycle, substituted heterocycle, alkyl ether, PEG, PEI, ether, or alkene. M may be one or more metals. X may be one or more counterions.

Substituents (e.g., $R^3$) may be configured to perform a variety of functions. By using different substituents, properties of a compound such as the bridged polycyclic compounds described herein may be customized to meet a particular industrial and/or individual's need. For example, $R^3$ may be hydrophobic or hydrophilic depending upon the specific property needed.

In some embodiments, a substituent (e.g., $R^3$) may be multifunctional such that it imparts two or more properties to a formed compound. For example a substituent (e.g., $R^3$) may function to increase the hydrophilicity of a compound, as well as, function as a cross-coupling reagent to cross-link compounds to one another under appropriate conditions (e.g., a substituent may include one or more heteroatoms within its structure such as N, O, and S).

In some embodiments, substituents such as $R^3$ may function to enhance hydrophobicity and/or lipophilicity. Depending upon the needs of a customer the hydrophobicity/lipophilicity of a compound may be increased. Adjusting the hydrophobicity/lipophilicity of a compound may consequently adjust the solubility of the compound in a particular solvent and/or matrix. Increasing the liphophilicity of a substituent (e.g., $R^3$) coupled to an ammonium salt may increase the anti-microbial activity of a compound. In some embodiments, a compound may have a minimum inhibitory concentration (MIC) of less than 900 μM, of less than 600 μM, or of less than 300 μM. A discussion of relationship between substituent chain length and antimicrobial activity of quaternary ammonium salts may be found in Pernak et al., "Synthesis and anti-microbial activities of some pyridinium salts with alkoxymethyl hydrophobic group" *Eur. J. Med. Chem.* 36 (2001) 899-907, which is incorporated by reference as if fully set forth herein.

The relationship between substituent chain length and antimicrobial activity is demonstrated in tests conducted on 113a, 113b, 113d, 113e, and 113h detailed herein in the Examples portion. A series of bridged polycyclic compounds were synthesized wherein different substituents were coupled to the quaternary ammonium moieties. Substituents included C1, C4, C6, C8, C12, and benzyl in combinations of C1 with C4, C6, C8, and C12, as well as, combinations of benzyl with C6 and C12. Time kill and residual surface tests of the antimicrobial strength of the compounds were tested against examples of gram+bacteria (e.g., *Staphylococcus aureus*, most common surgical wound infection), gram–bacteria (e.g., *Escherichia coli*, most commonly acquired hospital infection), and fungus (e.g., *Aspergillus niger*, a toxic black mold found in residences). Of the various alkyl chains combined with C1 tested, the C6,C1 compound tested as the strongest antimicrobial compound. When the test results of the C6,C1 were compared to the benzyl derivatives, once again, the C6,C1 derivative tested as the overall strongest antimicrobial.

The 113a C6C1 compound is unique in regards to the relatively short alkyl chain vs. known quaternary antimicrobials and high antimicrobial activity. Discrete quaternary ammonium or pyridinium antimicrobial molecules usually possess long alkyl chains. The most effective discrete (e.g., noncyclic) quaternary ammonium or pyridinium salt antimicrobials have an alkyl chain length between 12 and 18 carbon atoms as described by T. Loftsson et.al. in *J. Med. Chem.* 46, 2003, 4173-4181, which is incorporated by reference as if fully set forth herein.

In general it is known in the art that quaternary ammonium compounds are effective biocidal agents when they possess an alkyl chain with at least eight carbon atoms (S. Block, 'Disinfection, Sterilization and Preservation', $3^{rd}$ Ed., Lea and Febiger, Philadelphia, Pa., 1983; cited in 'Recent Advances in Antimicrobial Dendrimers', S. L. Cooper et.al. *Adv. Mater.* 2000, 12, no. 11, 843-846, which is incorporated by reference as if fully set forth herein). In a study of dendrimer quaternary ammonium salts, dendrimer biocides carrying $C_{10}$ alkyl chains were the most potent (S. L. Cooper et.al. *Biomacromolecules*, 1 (3), 473-480, 2000), which is incorporated by reference as if fully set forth herein.

Typically, non-discrete polymers are some of the only antimicrobials to show any appreciable antimicrobial activity with alkyl groups of <8 carbons. However, non-discrete polymers (e.g. polyethyleneimine quaternary ammonium containing polymers) demonstrated weaker overall antimicrobial activity in antimicrobial residual surface tests (A. M. Klibanov et.al. *Biotechnology Letters*, 25, 2003, 1661-1665), which is incorporated by reference as if fully set forth herein.

Furthermore, the straightforward route and synthesis efficiency makes bridged polycyclic compounds (e.g., 113a) more attractive from a manufacturing standpoint over the more laborious methods required for typical dendrimer synthesis. Both bridged polycyclic compounds (e.g., 113a) and dendrimers have the advantage of being polyvalent (multiple positively charged sites on one molecule to attract microbes) affording increased activity vs. traditional discrete quaternary ammonium salts (S. L. Cooper et. al. U.S. Pat. No. 6,440, 405). However, the dendrimer synthesis requires large volumes of solvents/reagents relative to obtained product and long periods of time (days) to synthesize as described by S. L. Cooper et. al. in U.S. Pat. No. 6,440,405, which is incorporated by reference as if fully set forth herein.

In some embodiments, substituents such as $R^3$ may function to enhance hydrophilicity and/or lipophobicity. Depending upon the needs of a customer the hydrophilicity/lipophobicity of a bridged polycyclic compound may be increased. Adjusting the hydrophilicity/lipophobicity of a compound may consequently adjust the solubility of the compound in a particular solvent and/or matrix.

In some embodiments, substituents such as $R^3$ may function to enhance the self-cleaning properties of which the compound may impart to a surface to which the compound is coupled. In some embodiments, substituents may enhance the antimicrobial properties of the compound. Self-cleaning and antimicrobial properties may function in combination with one another.

The search for self-cleaning surfaces has come about from the observation of such natural surfaces occurring naturally in nature, such as (e.g., lotus leaves). To clean a surface, material has to be transported along it, and best, off it. By tuning the wettability of the substrate, two basic options arise. The surface may be rendered very wettable, and the decontamination process is based on film flow. But, interestingly, biology hints at a different option. Non-wettable plant leaf surfaces, such as those of the famous *Lotus* plant, have a built-in elementary cleaning mechanism. This was noticed in the mid-nineties by botanists studying plant surfaces. They observed that droplets running off the leaves may carry dry contaminants along. Self-cleaning surfaces are believed to be a combination of low surface-energy species and a peculiar topographic feature based on dual-size roughness: the coarse-scale rough structure is about 10-20 μm, whereas the finer structure on top of the coarse structure is in the range of 100 nm to 1 μm. The dual-size structure has proven to be vital in generating the superhydrophobicity of the lotus leaves, especially for obtaining low water rolloff angles. Techniques for forming superhydrophobic surfaces may be found in Ming et al., "Superhydrophobic Films from Raspberry-like Particles" Nano Lett., 5 (11), 2298-2301, 2005, which is incorporated by reference as if fully set forth herein.

In some embodiments, a first compound described herein may include a plurality of second compounds coupled to the surface of the first compound. The first compound may be several times larger than the second compound. The first compound may be an order of magnitude or larger than the second compound. The first compound may include, but is not limited to, compounds such as compound 100. Second compounds may be coupled to active sites on the first compound to form a third compound. In some embodiments, the second compound may include, but is not limited to, compounds such as compound 100, coupled to active sites of a first compound. Coupling the third compound to a surface may provide the necessary surface topography (e.g., a dual-roughness) to produce a self-cleaning surface.

In some embodiments, a topology of a surface treated with the coating compositions described herein may have at least one layer having elevations whose average height may be from 20 nm to 25 μm and whose average separation is from 20 nm to 25 μm, whose average height is from 50 nm to 10 μm and/or whose average separation is from 50 nm to 10 μm, or whose average height is from 50 nm to 4 μm and/or whose average separation is from 50 nm to 4 μm. The topology of a surface treated with the coating compositions described herein may have elevations whose average height is from 0.25 to 1 μm and whose average separation is from 0.25 to 1 μm. The average separation of the elevations is the separation between the highest elevation of an elevation and the most adjacent highest elevation. If an elevation has the shape of a cone, the tip of the cone is the highest elevation of the elevation. If the elevation is a rectangular parallelepid, the uppermost surface of the rectangular parallelepid is the highest elevation of the elevation.

In some embodiments, a hydrophobic coating may be applied over a protective coating including a self-cleaning topological surface.

In some embodiments, substituents (e.g., $R^3$) coupled to portions of a compound may function as the finer structure relative to the coarser structure of the compounds. Substituents such as $R^3$ may increase the hydrophobicity of the compounds to which the substituents are coupled.

However, a disadvantage of the hydrophobic surfaces is that if the structures are sufficiently complicated, (e.g., moldings with undercuts or porous moldings or sponges, water may not then penetrate these voids) the result being that the cleaning properties of the surface may be inhibited. The globular shape of the water droplets on these surfaces may cause visual impairment if the droplets do not roll off from the surface because the surface is, for example, horizontal. In such instances, highly wettable surfaces may be advantageous, since a water droplet on these becomes distributed over almost the entire surface and forms a film of minimum thickness. This occurs in particular if the surface tension of the water is reduced by appropriate means (e.g., surfactants) and/or a hydrophilic surface is present. In some embodiments, hydrophilic substituents (e.g., $R^3$) may be coupled to active sites (e.g., amines) on compounds described herein. In some embodiments, hydrophilic substituents/coatings (e.g., hydrophilic silicas) may be coupled to compounds described herein. A discussion of hydrophilic substances and particles may be found in U.S. Patent Application, Publication No. 20050118911 to Oles et al. ("Oles"), which is incorporated by reference as if fully set forth herein. Increasing the hydrophilicity of a surface may inhibit microbial adhesion. Substituents for inhibiting microbial adhesion may be found in Ming et al., "Bacterial Adhesion at Synthetic Surfaces" *APPLIED AND ENVIRONMENTAL MICROBIOLOGY*, November 1999, p. 4995-5002, which is incorporated by reference as if fully set forth herein.

A self-cleaning surface including compounds may be enhanced by decreasing the surface energy or increasing the hydrophobicity of the self-cleaning surface. Several different techniques may be used in combination with compounds to increase the hydrophobicity and self-cleaning properties of a surface.

In some embodiments, a surface may be first coated with a hydrophobic substance (e.g., a hydrophobic polymer) and followed by applying compounds to the coating. The hydrophobic substance may be a matrix which also reacts with active sites on provided compounds (e.g., siloxy based polymers). In some embodiments, compounds may be dispersed within a matrix before applying the matrix to a surface. The matrix may act as a low energy hydrophobic coating which also couples the compounds to the surface after curing the matrix.

In some embodiments, counterions for a bridged polycyclic compound may be selected to adjust particular properties of a compound or to introduce new properties to the compound. Adjusting properties of a compound based on a selection of a particular counterion allows further customization of a compound. In some embodiments, counterions may include counterions which have or enhance antimicrobial properties and/or anti-inflammatory properties (e.g., boron, zinc). In some embodiment, counterions may adjust the hydrophilicity or hydrophobicity of the complex. Counterions may include metals. Research has held that specific counterions do affect the antimicrobial activity of quaternary ammonium compounds.

Counterions may include, but are not limited to, organic, inorganic, or organometallic moieties. Examples of counterions may include inorganic ions (e.g., halogen ions, such as fluorine, bromine, chlorine and iodine), organic ions (e.g., tosylate, prosylate sulfuric acid, nitric acid and phosphoric acid, and ions of organic acids such as succinic acid, fumaric acid, lactic acid, glycolic acid, citric acid, tartaric acid and benzoic acid), or coordinate type anions (e.g., fluoro sulfate and tetrafluoro borate).

In some embodiments, counterions may include a hydrophobic organic group (e.g., lauryl sulfate, dodecylbenzene sulphonate, diethylhexyl sulphosuccinate, carboxylic acid derivatives with alkane, alkene or alkyne aliphatic tails such as myristic acid salts, octadecanate, dodecanoic acid salts, oleic acid salts, Palmitoleic acid salts, lauric acid salts, Stearic acid salts, phosphinic acid salts, phosphonic acid salts (i.e. tetradecylphosphonate, hexadecylphosphonate) and dodecylsulphonate, dodecylsulfate anions).

In some embodiments, bridged polycyclic compounds may be polymerized. Polymers incorporating bridged polycyclic compounds may have molecular weights high enough to inhibit systemic absorption when, for example, ingested. The minimum molecular weight, and hence the degree of polymerization of bridged polycyclic compounds, required to inhibit systemic absorption may be relatively low. Nonsystemic polymers may include a minimum degree of polymerization of 3 or greater, 6 or greater, 10 or greater, 20 or greater, or 50 or greater. In some embodiments, an enteric coating may be applied to a composition in order to inhibit absorption and/or premature absorption.

In some embodiments, bridged polycyclic compounds may be polymerized in any number of ways known to one skilled in the art. Bridged polycyclic compounds may be polymerized using methods known to polymerize amines. In some embodiments, bridged polycyclic compounds (e.g., compounds 113 herein) may be polymerized via the tertiary amines or the secondary amines. For example, bridged polycyclic compound 401 may be polymerized via the tertiary amines.

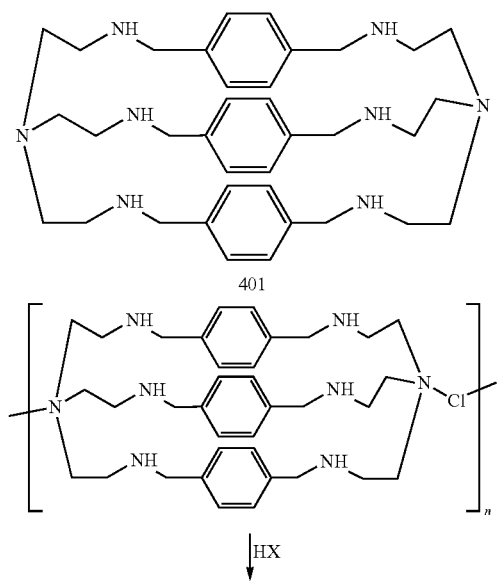

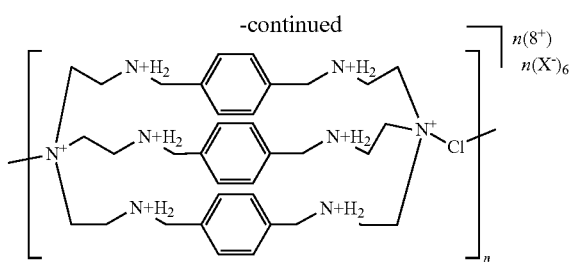

In some embodiments, C1 may be polyethylene glycol (PEG), alkyl, and/or aryl. In some embodiments, X may include niacin, butyrate, a statin (e.g., Atorvastatin, Exetimibe), or other anionic counterion. Any bridged polycyclic compound described herein may be polymerized.

In some embodiments, a polymerized bridged polycyclic compound may be substituted with linkers as described herein such that, for example, more pharmaceutical agents may be coupled to the polymer. For example, guanidine moieties may be used to replace the (H) of (—NH—), then add HX to form the salt of guanidine moiety and the cage amines to give higher overall charge.

Synthesis of Bridged Polycyclic Compounds

For commercialization purposes compounds such as bridged polycyclic compounds (and their metal and/or metal oxide coated counterparts) require an efficient and cost effective method of synthesis. In some embodiments, bridged polycyclic compounds may be formed through the self-assembly of two or more compounds to form much larger complex system in fewer steps and more efficiently than traditional stepwise synthetic means.

At the most general level, the words "self-assembly" are used to identify the phenomenon whereby some kind of higher-level pattern emerges from the interactions of multiple simple components. An example of self-assembly from the Stang group is shown in Scheme 1 (Stang, P. J.; Cao, D. H. *J. Am. Chem. Soc.* 1994, 116, 4981). To set this particular type of self-assembly in its proper context, it should be noted that in the field of chemistry, the term "self-assembly" is used to describe two distinct types of processes. On the one hand, there are assemblies that lead to the formation of essentially infinite arrays, while on the other hand, there are assemblies such as that shown in Scheme 1 that lead to distinct, bounded species. Furthermore, within each of these categories, it is possible to make a further distinction that reflects the scale of organization. For example, for infinite arrays, one may consider processes such as crystallization, where the molecules are ordered at the molecular level (ca. $10^{-9}$ m), or the formation of self-assembled monolayers and bilayers, where there is little order between individual molecules, but a larger scale of organization is evident across say the $10^{-6}$ m level. Likewise, the scale of organization for assemblies leading to distinct species may be broken down into similar categories. It may be noted the self-assembly of macroscale objects ($10^{-3}$ m) is currently being investigated. However, as far as the interaction of molecules to form distinct species goes, it may be considered the formation of micelles and vesicles that constitutes assembly at the $10^{-6}$ m level.

Scheme 1. A typical strict self-assembly reported by Stang et al.

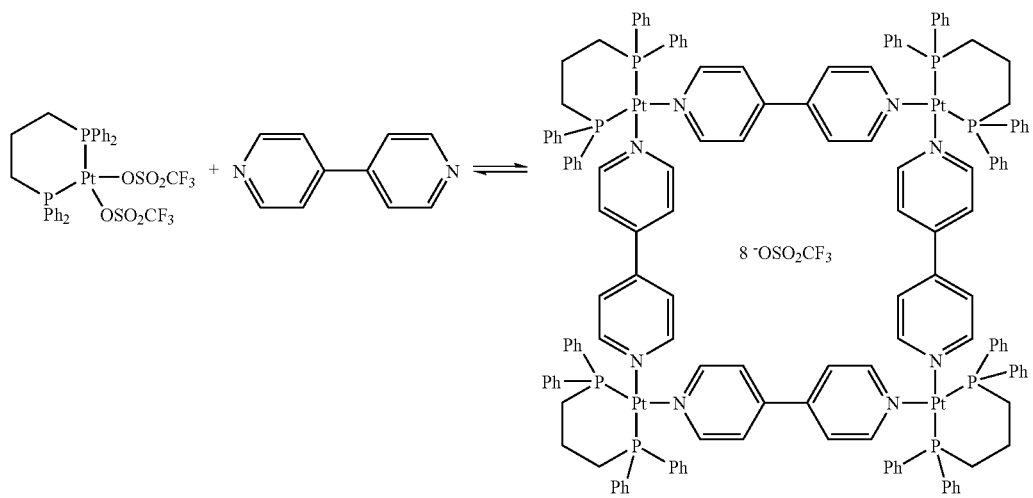

The essential features of chemical assembly processes is that they share a common self-correcting mechanism. In other words, strict self-assemblies are fully reversible, dynamic, systems that lead to a product that represents the global thermodynamic minimum for the system. Sometimes an additive or template is needed to boost the efficiency of the assembly, but this is the only true variable if one is speaking of strict self-assembly. At their cores, strict molecular assemblies consist of subunits, product, and an equilibrium that relates the two.

In some embodiments, self-assembly techniques (e.g., dynamic covalent chemistry) may be employed to synthesize stable compounds, which are themselves large enough to be described as nanoparticles and/or which may be used to form nanoparticles.

Bridged polycyclic compounds represented by compounds 104 and 108 may be synthesized by any means known to one skilled in the art. As has been mentioned, self-assembly may be a useful technique for efficiently synthesizing nanoparticles described herein. In some embodiments, nanoparticles such as compounds 104 and 108 may be formed via self-assembly using Schiff base condensation reactions between amines and aldehydes to form an imine as depicted in Scheme 3. For example, a trifunctional amine (e.g., tris(2-aminoethyl) amine (TREN)) may be reacted with a bifunctional aldehyde (e.g., ethane-1,2-dione (glyoxal)).

Scheme 3. Schematic depiction of the formation of compound 102.

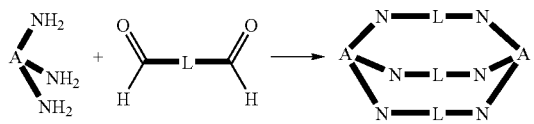

In Scheme 3, the amine depicted is trifunctional and the aldehyde is bifunctional. However, the example depicted in Scheme 3 should not be seen as a limiting embodiment. For example, a Schiff base condensation reaction is depicted in Scheme 4 in which the amine is bifunctional and the aldehyde is trifunctional.

Scheme 4. Schematic depiction of the formation of compound 102.

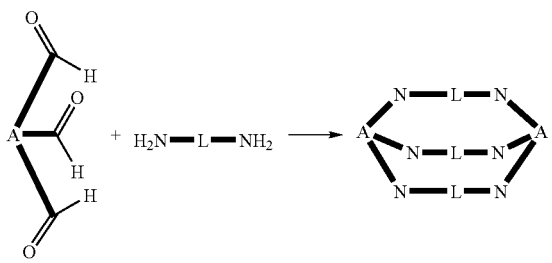

In some embodiments, two different trifunctional molecules may be reacted with one another in order to form an asymmetric adduct. Scheme 4a depicts an embodiment of the formation of an asymmetric adduct.

Scheme 4a. Schematic depiction of the formation of compound 100c.

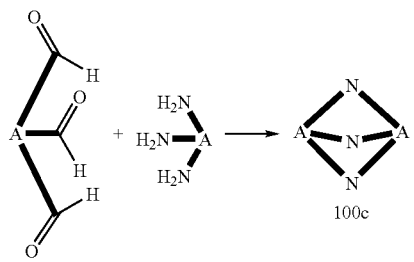

For example, a trifunctional amine (e.g., tris(2-aminoethyl) amine (TREN)) may be reacted with a trifunctional aldehyde (e.g., 1,3,5-aldehyde substituted phenyl). Triethanolamine may be functionalized at the OH with an aminoacid to give N—($CH_2CH_2OC(O)Phenyl(CHO)$). N—($CH_2CH_2OC(O)$) Phenyl(CHO) may be reacted with any triamine to give an asymmetric example of a bridged polycyclic compound. A discussion of synthesis techniques for different multifunctional ligands (e.g., trifunctional aldehydes) may be found in Chand et al. "Synthesis of a Heteroditopic Cryptand Capable of Imposing a Distorted Coordination Geometry onto Cu(II): Crystal Structures of the Cryptand (L), [Cu(L)(CN)](picrate), and [Cu(L)(NCS)]{picrate} and Spectroscopic Studies of the Cu(II) Complexes" Inorg Chem 1996, 35, 3380-3387, which is incorporated by reference as if fully set forth herein.

In some embodiments, formation of a bridged polycyclic compound (e.g., Schemes 4, 4a, or 5) may be carried out in an alcohol (e.g., ethanol).

A more specific example of the self-assembly Schiff base condensation strategy depicted in Scheme 3 is depicted in Scheme 5 showing the formation of imine compound 116. Imine compound 116 may be used as an intermediate toward the formation of compound 110.

Scheme 5. Schematic depiction of the formation of compound 116.

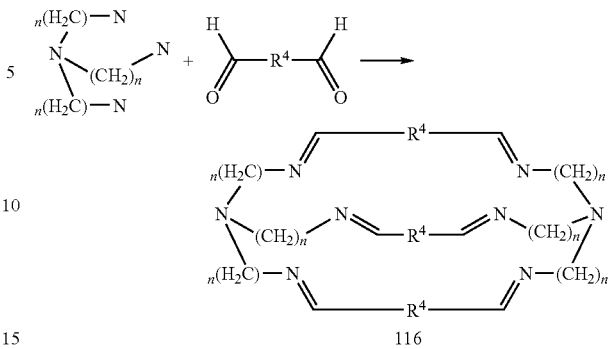

A Schiff base condensation may be carried out using an acid catalyst (e.g., acetic acid). A Schiff base condensation may be carried out using any means known to one skilled in the art. Techniques for amine aldehyde condensations may be found in U.S. Patent Application, Publication No. 2004/0267009 to Redko et al. ("Redko"), which is incorporated by reference as if fully set forth herein.

In some embodiments, a reduction may be carried out in an alcohol (e.g., ethanol) with a reducing agent (e.g., sodium borohydride).

In some embodiments, coupling of corner units or corner units and linker units to form bridged polycyclic imine compounds may be carried out in an alcohol (e.g., ethanol) based solvent. In some embodiments, reduction of at least some of the imines may be carried out without any substantial work up directly following the coupling step (e.g., by adding a reducing agent such as sodium borohydride) to form a bridged polycyclic compound.

In the past reactions such as the coupling and reduction steps have been carried out as two totally separate steps involving for example working up (e.g., purifying and isolating) the reaction after the coupling step before the reducing step. One or more of these steps (e.g., the coupling step) have in the past been carried out in for example acetonitrile resulting in a seemingly polymeric substance, followed by an isoxolate extraction. In reality the isoxolate extraction may have been merely driving the reaction towards the bridged polyclic product, by conversion of polymer and oligomer products.

Running the reactions in a solution of heated ethanol results in almost quantitative yields of the desired product without any substantial work up or isolation protocols.

In some embodiments, coupling of corner units or corner units and linker units to form bridged polycyclic imine compounds may be carried out in a green solvent. In some embodiments, a green solvent may include any solvent which is naturally occurring and which has been found not to harm the environment when used on an industrial scale. In some embodiments, a green solvent may include water or an alcohol based solvent (e.g., ethanol). A catalyst may be used to run the reaction in water. In some embodiments a catalyst may include aniline. A similar method is described in Angewante Chemie Vol. 45, pages 75-81, which is incorporated by reference as if fully set forth herein.

In another example of functionalizing an amine at least in part defining a bridged polycyclic compound, a functionalized substituent may be coupled to the amine. A functionalized substituent may include an alkyl amine group. A non-limiting example of an alkyl amine may include —$CH_2CH_2CH_2NH(CH_2)_5CH_3$. The amine may be further functionalized. For example the amine of the alkyl amine may be alklyated such that another quaternary amine is available increasing the antimicrobial activity of the bridged polycyclic compound. The synthesis of such an embodiment is detailed in the Examples section.

In some embodiments, following a reduction to form a bridged polycyclic amine, such as compound 120 or a compound such as compound 301 having a structure (301)

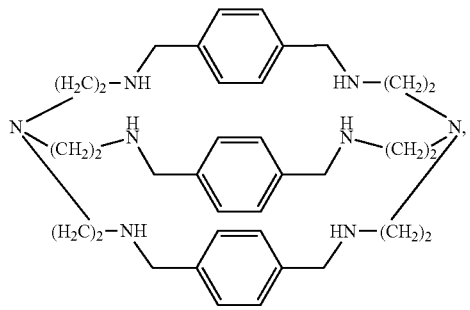

a linking agent (e.g., to couple a pharmaceutically active agent to) or a pharmaceutically active agent may be coupled to a bridged polycyclic amine such as compound (301). Linking agents may be, for example, any of the compounds or reagents identified herein as $R^3$.

Following are some representative example of activating agents and how to synthetically couple them to compounds such as compound 301.

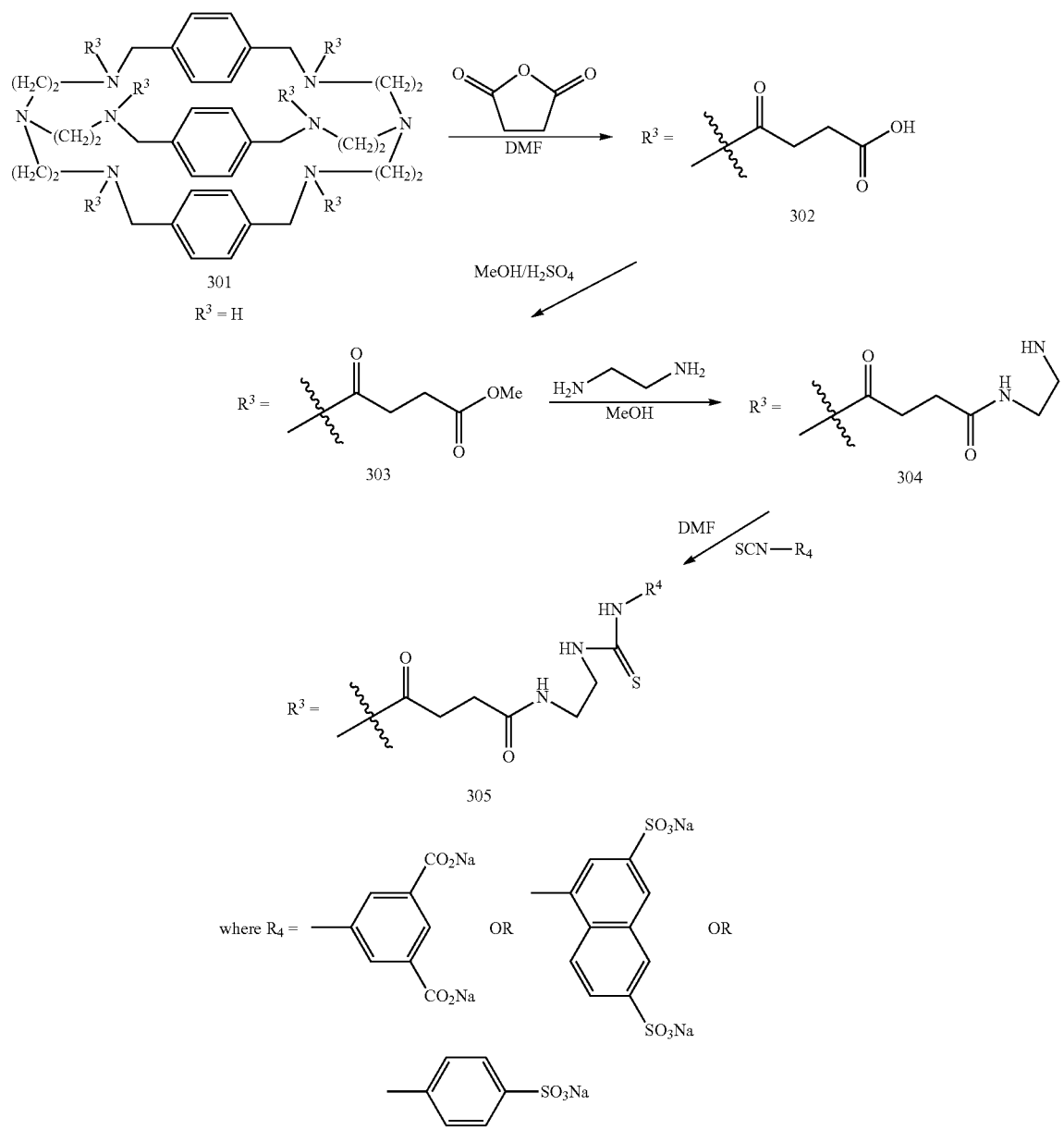

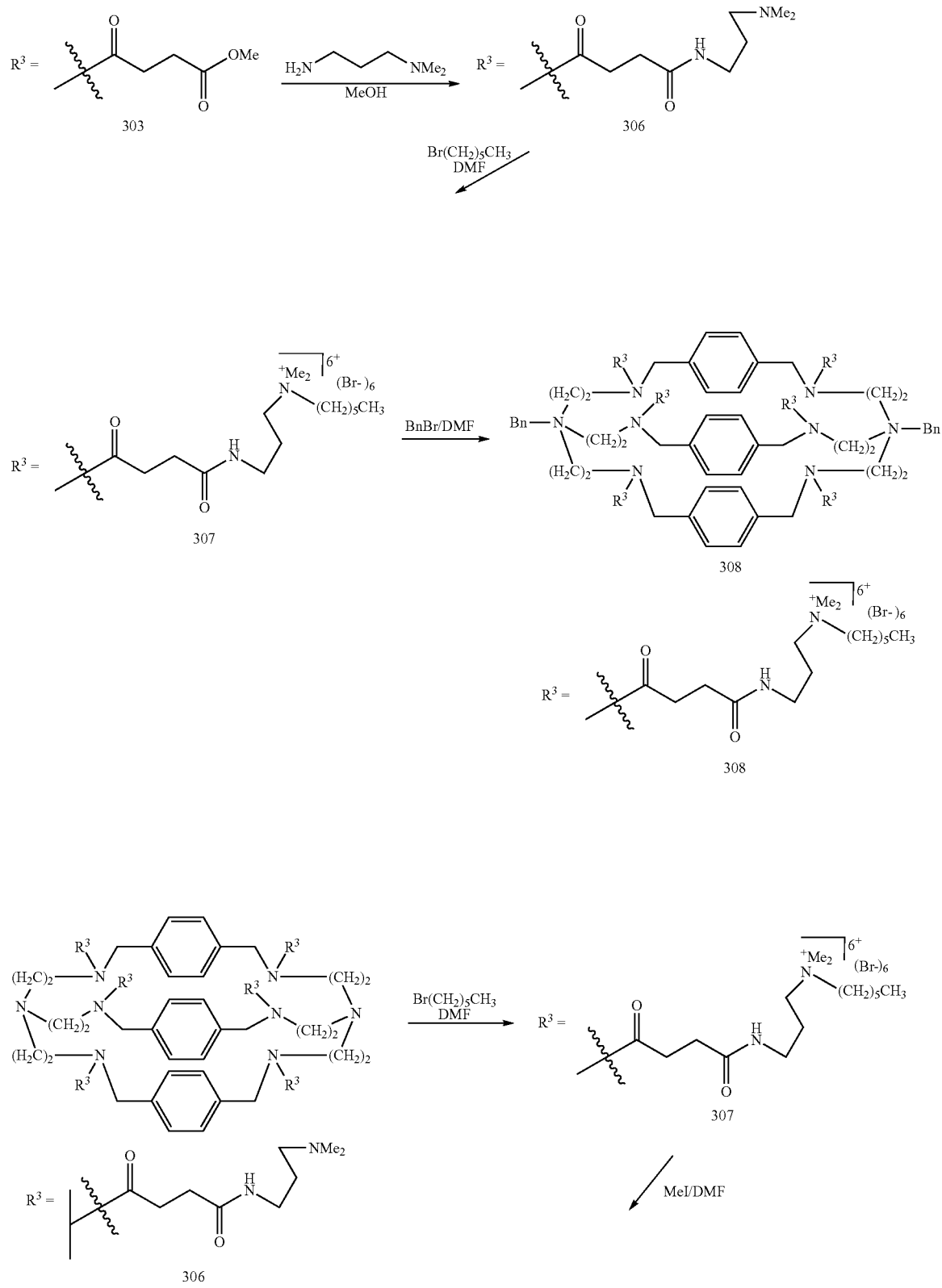

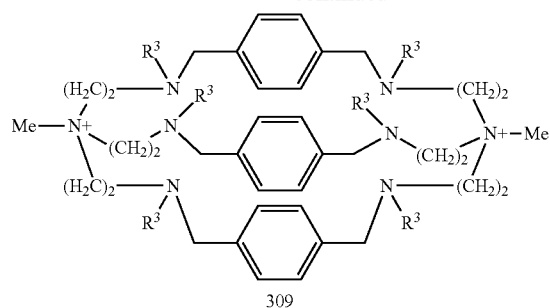
309
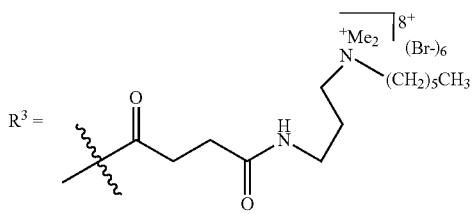
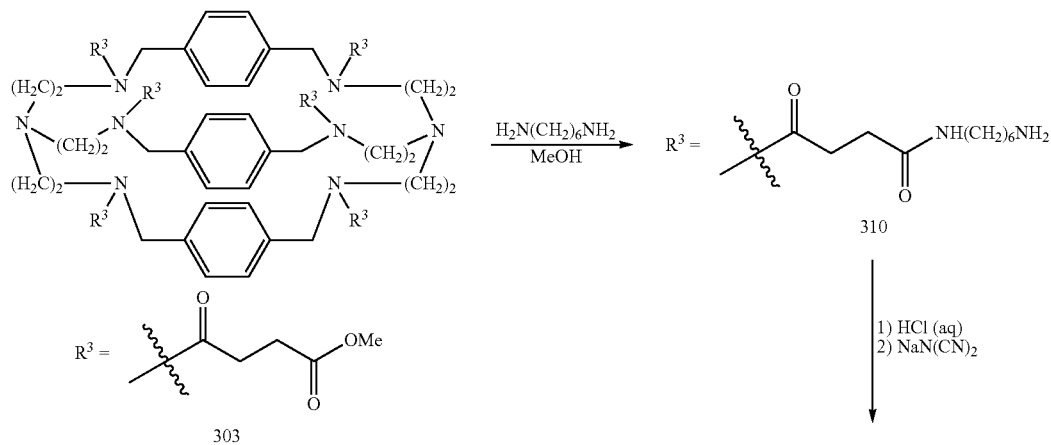
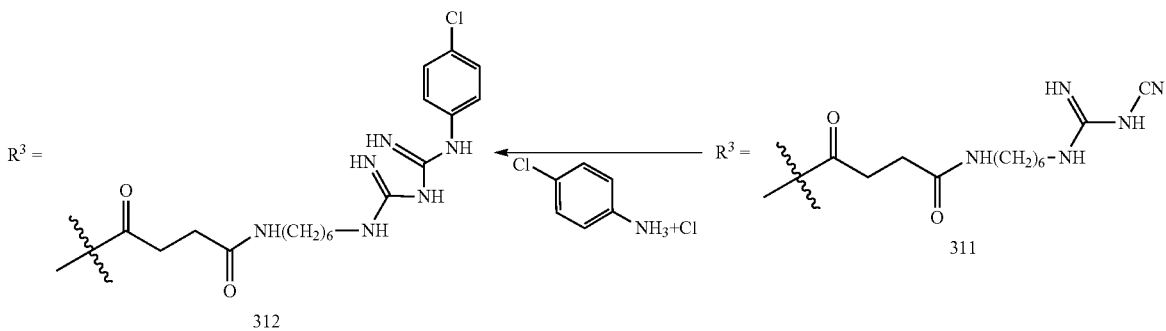
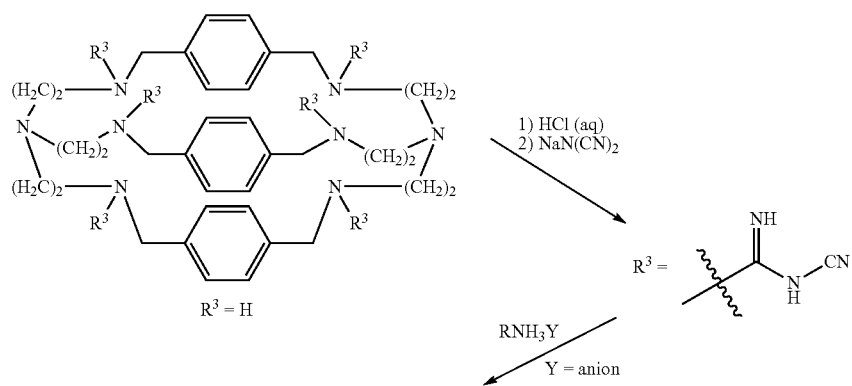

-continued

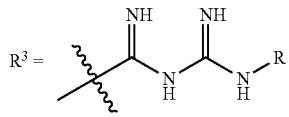 

Where R = aryl, alkyl and substituted aryl and substituted alkyl groups, hetero atom containing groups, or and salt derivatives thereof . . .   X = halogen

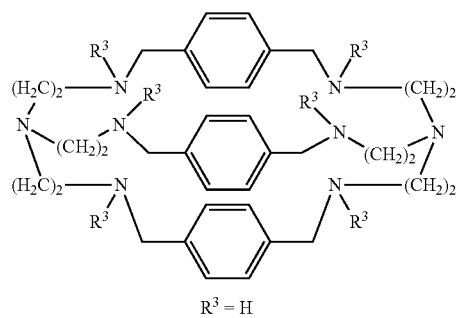 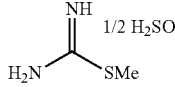 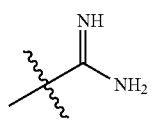

$R^3 = H$ and salt derivatives thereof . . .

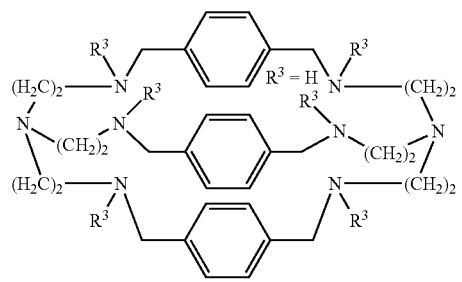 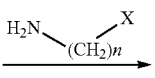 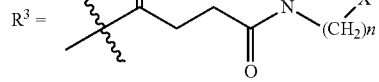

Where $n = 0$ to 12 and X is a sugar or carbohydrate

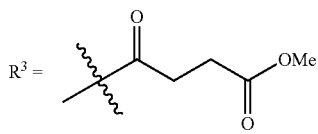

Following is a representative example of how to synthesize a bridged polycyclic compound including a pharmaceutically active agent coupled to the bridged polycyclic compound.

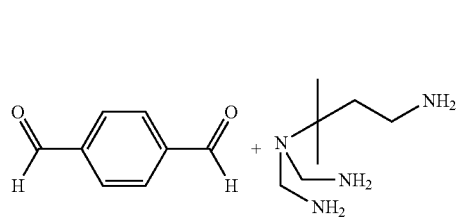 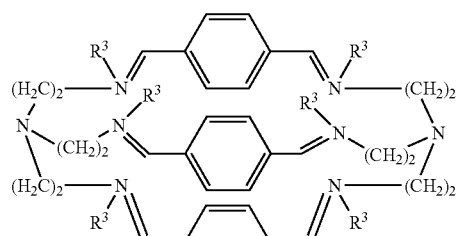

1

↓ NaBH$_4$/67 C.

-continued
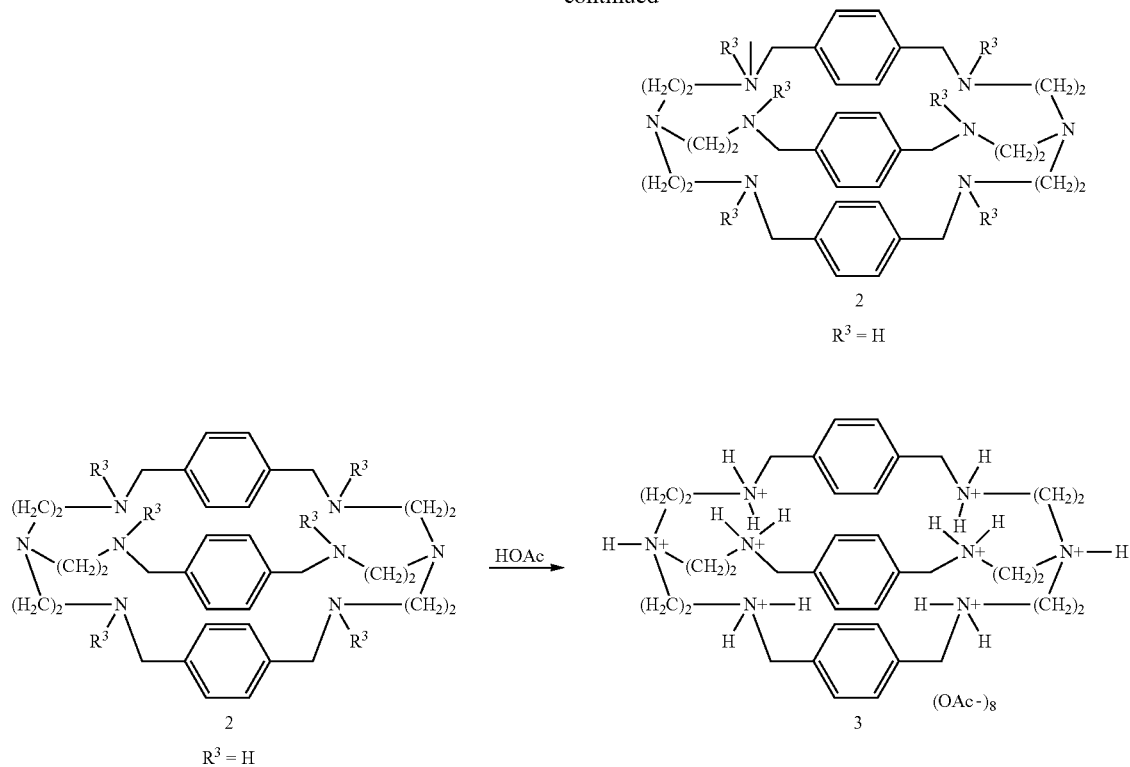
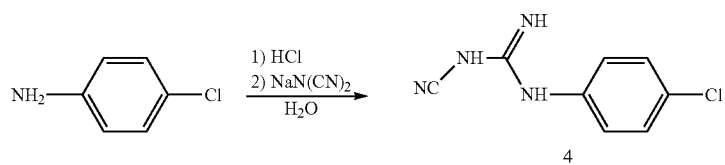
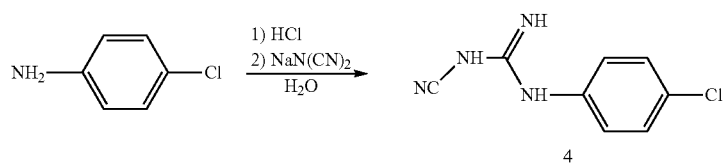
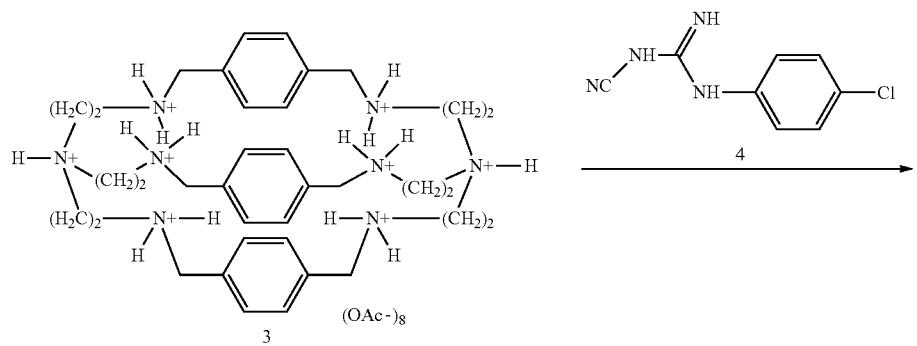

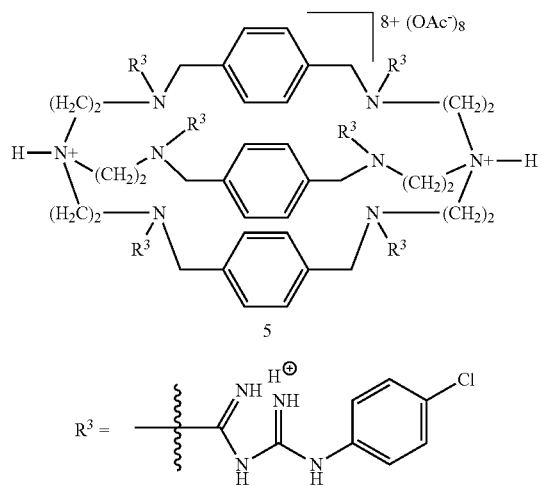
In some embodiments, it may be advantageous to increase the number of active sites on to which to couple pharmaceutically active agents such as depicted directly below in the following two schemes.
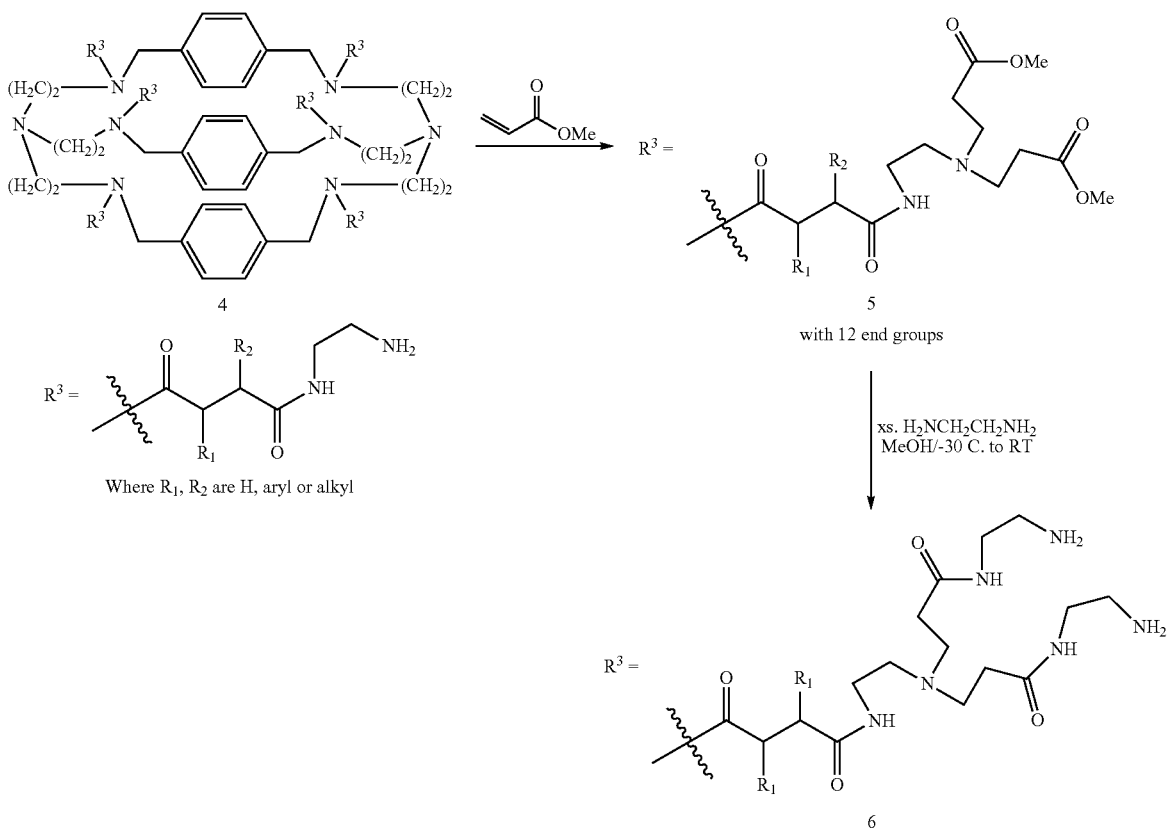

Following are some representative examples of pharmaceutically reactive agents and how to synthetically couple them to linking agents and/or bridged polycyclic compounds such as compound 301.
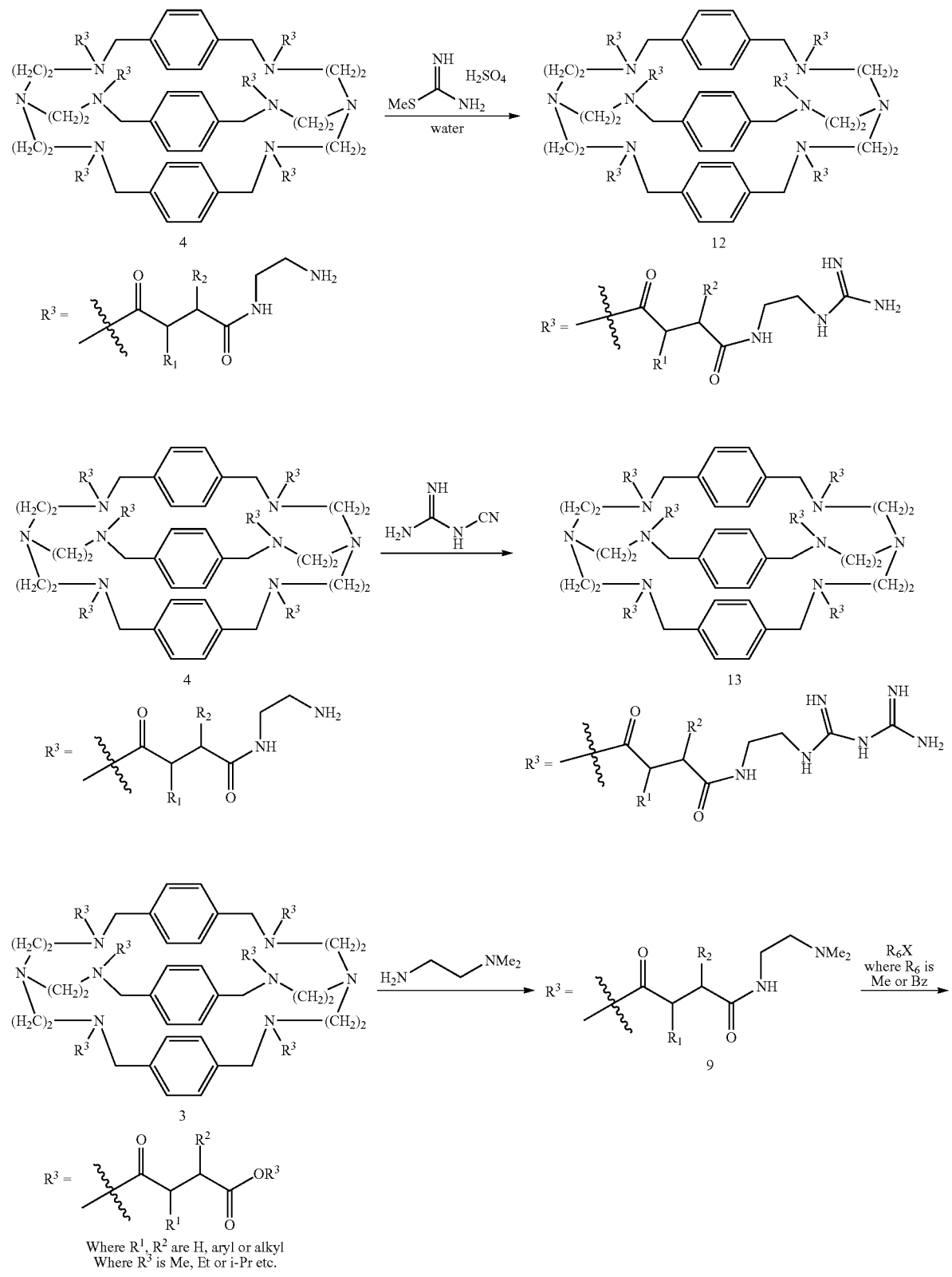

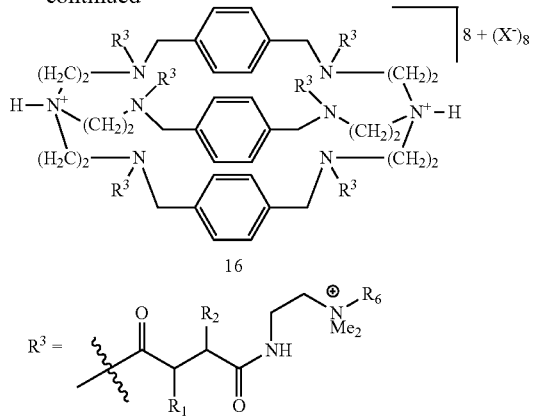

An example would be synthesis with nonenylsuccinic anhydride to make $R_1$ or $R_2$ $CH_2CH=CH(CH_2)_5CH_3$.

Compositions Comprising Bridged Polycyclic Compounds

In some embodiments, bridged polycyclic compounds may be incorporated into a composition which is substantially nontoxic to animals and/or humans. A composition may include a solvent capable of dissolving a bridged polycyclic compound. In some embodiments, a composition may include an environmentally green solvent. A solvent may include water and/or ethyl alcohol. In some embodiments, a composition may consist of water and a bridged polycyclic compound. Such compositions may be administered using any method described herein including, but not limited to, orally, topically, intravenously, absorbed through the skin, injected, etc.

In some embodiments, a composition may be applied to an oral surface. An oral surface may include at least a portion of a tooth surface, at least a portion of a gum, at least a portion of soft tissue, at least a portion of soft tissue on or near a tooth extraction site, at least a portion of soft tissue on or near a root canal site, at least a portion of a tooth on or near a root canal site, at least a portion of soft tissue on or near an oral surgery site, at least a portion of a tooth on or near an oral surgery site, at least a portion of bone on or near a tooth extraction site, at least a portion of bone on or near an oral surgery site, and/or at least a portion of a dental fixture (e.g., a filling, a bridge, a denture).

In some embodiments, an oral composition may include a flavoring. A flavoring may include something a human (e.g., especially children) may find palatable. For example a flavoring may include malt extract, xylitol, splenda, sucralose or any sweetener. A flavoring may range from 0.01% to 0.10%, 0.10% to 1.0%, or 1.0% to 10.0% of a composition.

In some embodiments, a composition may include a colorant. A colorant may include D&C Blue #1 or any FDA approved color. A colorant may range from 0.001% to 0.010%, 0.010% to 0.10%, or 0.10% to 1.0% of a composition.

In some embodiments, an oral composition may include a fragrance.

In some embodiments, a composition may include additional additives which may function in combination or separately from the bridged polycyclic compound in solution. Additives may function to improve a subject's health. Additives may include vitamins including, but not limited to, vitamins D and E.

All types of teeth and gum diseases can lead to serious health problems in humans. Toothache, dental disease and loss of teeth can all have serious consequences for humans. Damage to the teeth and gums in humans may be permanent and irreversible.

In some embodiments, different compositions may be formulated for different types of users. For professionals users (e.g., doctors), compositions may include a greater percentage of active bridged polycyclic compounds than compositions formulated for over the counter sale to nonprofessionals. In some embodiments, professional compositions may not include flavorings or colorants.

In some embodiments this antimicrobial may be incorporated into dental systems for plaque prevention. A system featuring a dental barrier sealant and a plaque prevention gel may significantly reduce the formation of plaque and calculus, two factors in the onset of periodontal disease. Compositions described herein may be used, for example, for general dental oral health and preventative maintenance, dental surgery oral rinse, and/or oral infection (e.g., stomatitis).

In some embodiments, a composition comprising one or more compounds described herein may inhibit and/or ameliorate human oral conditions including, but not limited to, tooth lesions, dental fractures, periodontal disease (gingivitis, periodontitis), stomatitis, gingivitism, inflammation of periodontal structures, infection and/or inflammation from root canal procedures (e.g., used in combination or in place of root canal sealer, paste and or root canal filling material (e.g., rubber compound gutta percha)), abscessed tooth and/or tooth roots, infection and/or inflammation from endodontic surgical procedures, oral mucosa, lips and/or tongue, periodontal disease, palatitis, faucitis (inflammation of the caudal fauca), glossal ulceration, pharyngitis, submandibular lymphadenopathy (swollen glands), fungal infection, infection, viral infection, disease, bacteria, microbes, parasites, herpes, a sore, an oral cavity sore, a wound, a tooth fissure, a tooth cavity, a cut, and/or a canker sore.

Periodontal tissues may be damaged and/or destroyed if intervention does not occur. An unusually aggressive response by a subject's immune system may explain why some individual patients exhibit rapidly progressing more severe disease.

If an oral malady is diagnosed early enough aggressive and regular oral cleaning may eventually clear up the malady, but not necessarily. A dentist and/or subject may have to clean the oral cavity several times a week for months. Many times, especially if the malady is not diagnosed early enough, the only recourse available is oral surgery including, for example, extracting any effected teeth. Infection and/or inflammation can result from oral surgery and sutures where the invention can be used to prevent further infection and/or assist healing.

Demanding requirements such as those for dental materials also exist in numerous other products such as coatings. Recent developments in nanotechnology are increasingly being considered to address these requirements. A key challenge to widespread adoption of nanotechnology to such applications is the ability to manufacture non-agglomerated discrete nanoparticles that can be homogeneously distributed in resins or coatings to produce nanocomposites.

In some embodiments, a dental composition may include bridged polycyclic compounds. At least one of the bridged polycyclic compounds may include at least two cyclic groups. At least two of the cyclic groups may include quaternary ammonium or amine moieties. In some embodiments at least two of the cyclic groups may be defined at least in part by quaternary ammonium moieties. Bridged polycyclic compounds may include any of the compounds described herein.

Dental sealants formed from compositions including bridged polycyclic compound 5 were used in a study on canines for gingivitis gingivitis, gingival bleeding, plaque, and calculus. Results of the canine study included a significant reduction in gingivitis, gingival bleeding, and periodontal disease from a single application of the Dental Sealant Varnish with or without a prophylaxis (dental cleaning). A dental checkup and assessment more than six months after application of the Dental Sealant Varnish showed similar results in the Dental Sealant Varnish Group vs. the Control Group in overall oral health.

Dental sealants formed from compositions including bridged polycyclic compound 5 were used in a study on felines for gingivitis, gingival bleeding, plaque, calculus, FORLs (Feline odontoclastic resorptive lesions), stomatitis and/or CUPS (Chronic ulcerative paradental stomatitis). Results of the feline study included a significant reduction in gingivitis, gingival bleeding, FORLs, CUPS, stomatitis as well as plaque and calculus reduction was observed for the Dental Varnish Sealant Study Group with no significant change for the Control Group.

In some embodiments, a composition may be applied to an oral surface or at least to a portion of an oral surface. An oral surface may include at least a portion of a dental fixture.

A method may include applying a dental composition to dental fixture such as bridges, caps, retainers, dentures and any temporary or permanent dental fixture in the oral cavity. A composition may be applied to at least a portion of a dental fixture or over substantially all of a dental fixture. A composition may be applied to an underside of a dental fixture. Many times problems occur after an oral procedure has been performed. An oral procedure may include periodontal surgery, wherein infections may occur underneath any dental fixtures installed during surgery. A composition applied to a dental fixture may inhibit occurrence of any maladies such as infection.

In some embodiments, a composition may be applied to an oral surface at a point of infection (e.g., lesion, ulcer).

In some embodiments, a dental composition may include core-shell nanoparticles as described herein.

In some embodiments, a dental composition may include nanoparticles as described herein.

A dental composition and method of use of the same may be used in restoring the function and anatomy of a tooth. Dental compositions as described herein may be used in bonding agents, resin cements, sealants, varnishes, gels and resins. Dental compositions may include polymerizable unsaturated monomers, oligomers, prepolymers, or combinations thereof. Dental compositions may inhibit tooth decay and/or microbial growth in and around an oral cavity. Dental compositions may inhibit secondary decay.

Some commonly found bacteria leading to tooth decay and/or other oral maladies have been known for some time (e.g. *Actinomyces israelii, A viscosus, A naeslundii, Arachnia propionica, Rothia dentocariosa, Bacterionema matruchotii*, and *Corynebacterium acnes*) as described by J. M Slack, et.al. in J. Dent. Res 50(1): 78-82, 1971, incorporated by reference as if set forth fully herein. Other bacteria which lead to oral maladies may include *Streptococcus mutans, Porphymonas Gingivalis*, and *Haemophilus actinomycetemcomitans*.

Figure 2:
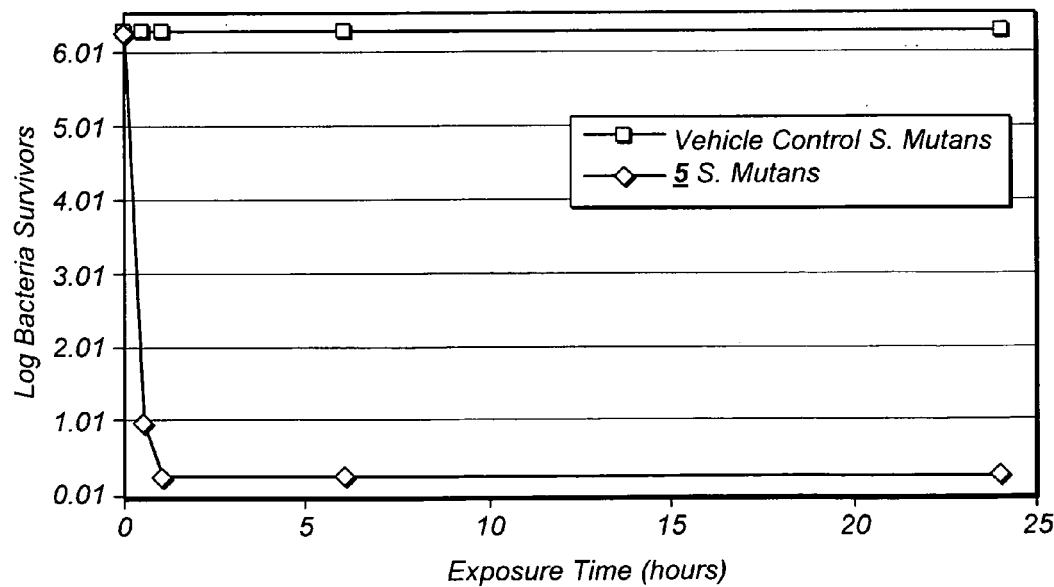
FIG. 2 depicts a graphical representation of time kill assay tests for a bridged polycyclic compound tested against *Streptococcus mutans*.
Figure 3:
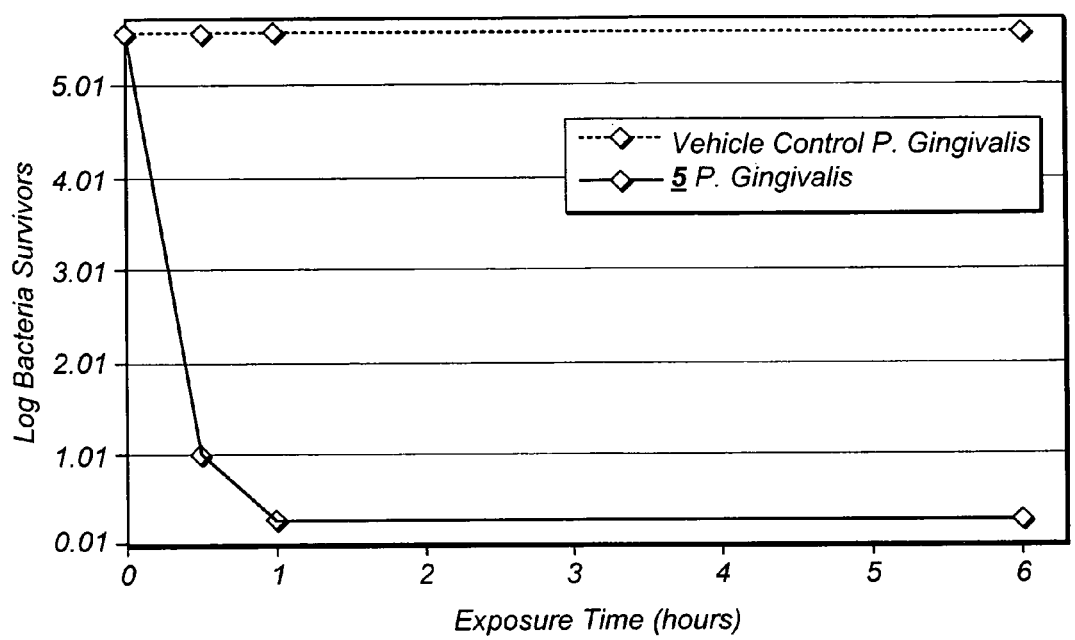
FIG. 3 depicts a graphical representation of time kill assay tests for a bridged polycyclic compound tested against *Porphymonas Gingivalis*.

FIGS. 1-3 depict a graphical representation of time kill assay tests for bridged polycyclic compound 5 tested against *Haemophilus Actinomycetemcomitans, Streptococcus mutans*, and *Porphymonas Gingivalis* respectively. The test results demonstrate how effective bridged polycyclic compounds are against known destructive microbes.

In some embodiments, dental compositions may enhance sustained antimicrobial activity with minimum harm to the living structure and surrounding tissues and without affecting the composition's restorative properties.

In some embodiments, dental compositions described herein may be used for oral trauma treatment. Dental composition may be used for oral trauma treatment field kits used for the temporary or permanent treatment of oral trauma out in the field when specialized help is not readily available. Dental compositions may be used in combination with gelators, absorbents, and/or coagulating agents to prepare oral antimicrobial wound dressings.

Nanoparticles have been shown to enable nearly 50% reduction in filling shrinkage. These nanocomposites are suggested to be particularly useful for fabricating load bearing and cosmetic restorations. Examples of nanoparticles and general properties which they impart to dental compositions may be found in U.S. Pat. No. 6,593,395, which is incorporated by reference as if fully set forth herein.

A dental composite may have a high strength required for load-bearing restorations, yet maintains a glossy appearance, even after substantial wear. Through the use of particles having a mean particle size between about 0.05 .mu.m and about 0.50 micromolar, the composite is useful in stress bearing restorations and in cosmetic restorations. The structural filler used is typically ground to a mean particle size of less than 0.5 micromolar and also includes a nanofiller having discrete particles of a mean particle size less than 100 nm to improve handling and mechanical characteristics. The preferred dental composites maintain their surface finish even after substantial use and also have the strength properties of hybrid composite resins.

In some embodiments, a dental composite, comprising: a polymerizable resin base; and about 10% by volume to about 80% by volume filler consisting essentially of a ground structural filler and a non-ground nanofiller, wherein the ground structural filler comprises between about 10% by volume and about 70% by volume of the composite and consists of ground particles of mean particle size between about 0.05 μm and about 0.50 μm, and wherein the ground structural filler contains less than 50% by volume of particles above 0.5 μm in diameter, and wherein the non-ground nanofiller comprises between about 1.0% by volume and about 15% by volume of the composite and consists essentially of discrete, non-aggregated gamma alumina particles having a mean particle size of about 40 nm or less.

The resin composite, in the cured form, may have a flexural strength of at least 100 MPa.

The resin composite, in the cured form, may have a flexural strength of at least 120 Mpa.

The resin base comprises a polymerizable vinyl compound.

The ground structural filler contains less than 10% by volume of particles above 0.8 micromolar in diameter.

The non-ground nanofiller comprises between about 5 and about 12% by volume of the composite.

The non-ground nanofiller may have a refractive index in the range of about 1.48 to about 1.6.

A dental composite comprising: a polymerizable resin base; and about 11% by volume to about 80% by volume filler in the resin base, the filler consisting essentially of a ground structural filler and a non-ground nanofiller, wherein the ground structural filler comprises between about 10% by volume and about 70% by volume of the composite and consists of ground particles having a mean particle size of between about 0.05 .mu.m and about 0.50 .mu.m, and wherein the non-ground nanofiller comprises between about 1.0% by volume and about 15% by volume of the composite and consists essentially of discrete, non-aggregated aluminosilicate particles having a mean particle size of less than about 100 nm, and a 1:4 molar ratio of alumina to silica.

The resin composite, in the cured form, has a flexural strength of about 120 MPa or greater.

The resin base includes a polymerizable vinyl compound.

The non-ground nanofiller comprises between about 5% by volume to about 12% by volume of the composite.

The aluminosilicate particles have a mean particle size of about 80 nm.

The resin composite, in the cured form, has a flexural strength of at least 100 MPa.

The ground structural filler contains less than 10% by volume of particles above 0.8 .mu.m in diameter.

The non-ground nanofiller has a refractive index in the range of about 1.48 to about 1.6.

A dental composition may include a polymerizable compound, a polymerization initiator system, bridged polycyclic compounds, or combinations thereof. These compositions may be suitable for restoring the functionality and anatomy of a damaged tooth. Uses may include, but are not limited to, use as dental polymers, dental primers, adhesives, dental sealent, bonding agent, dentin bonding agent, dental composite, dental filling, surface sealants, liners, outing cements, varnishes, impression materials, equipment and impression systems, and composite restoratives. Uses may include, but are not limited to, impression materials, coatings for impression trays, and impression systems. In some embodiments, dental compositions may impart antimicrobial activity to a contacted tooth structure and/or surrounding tissue.

In some embodiments, a composition may include a polymer, a polymer may include a poly vinyl, a poly vinyl acetate-copolymer, poly(vinyl acetate-co-acid), latex, an acrylate, an methacrylate, cyanoacrylate, a resin, a light cured resin, a self-cured resin, a cement, a glass ionomer cement (GIC), a polyurethane resin, or a bisphenol A glycidyl (bis-GMA) resin, The present dental compositions may include a polymerizable compound (e.g., at least one polymerizable monomer or prepolymer selected from those known in the art of dental materials) including, but not limited to, polymerizable amides, esters, alkenes, imides, acrylates, methacrylates, urethanes, vinyl esters or epoxy-based materials. Other polymerizable compounds may include those based on styrene, styrene acrylonitrilic, sulfones, acetals, carbonates, phenylene ethers, phenylene sulfides, or other polymerizable units listed herein. Examples of dental compositions and additives typically used may be found in U.S. Pat. No. 6,326,417, which is incorporated by reference as if fully set forth herein. Examples of dental compositions and additives typically used may be found in U.S. Pat. Nos. and Patent Application Nos. 6,500,004; 6,326,417; 20010009931; 20050252413; and 20030134933 (acidic based sealants) which are incorporated by reference as if fully set forth herein.

Polymerizable compounds may include ethylenically unsaturated monomers and prepolymers and include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Wakline, which are incorporated by reference as if fully set forth herein. Methacrylate-based monomers may be used (e.g., condensation product of bisphenol A and glycidyl methacrylate, 2,2'-bis[4-(3-methacryloxy-2-hydroxy propoxy)-phenyl]-propane ("BIS-GMA"), dipentaerythritol pentaacrylate (DPEPA), pentaerythritol dimethacrylate (PEDM), the condensation product of ethoxylated bisphenol A and glycidyl methacrylate ("EBPA-DMA"), and the condensation product of 2 parts hydroxymethylmethacrylate and 1 part triethylene glycol bis(chloroformate) ("PCDMA")). Polymerizable compounds may include polyurethane-based dimethacrylates ("PUDMA").

Polymerizable compounds may include polymerizable diluent monomers. Such monomers are generally used to adjust the viscosity of a polymerizable composition. Suitable methacrylate-based diluent monomers may include, but are not limited to, hydroxyalkyl methacrylates (e.g., 2-hydroxyethyl methacrylate, 1,6-hexanediol dimethacrylate, and 2-hydroxypropyl methacrylate); glyceryl dimethacrylate; and ethyleneglycol methacrylates (e.g., ethyleneglycol methacrylate, diethyleneglycol methacrylate, triethyleneglycol methacrylate, Triethyleneglycol dimethacrylate, and tetraethyleneglycol methacrylate).

When used as primers, adhesives, or primer/adhesive, dental compositions may include a polymerizable compound including hydrophilic polymerizable monomers to enhance the bonding characteristics of the dental composition. Suitable polymerizable hydrophilic monomers may have carboxyl, phosphoryl, sulfonyl, and/or hydroxyl functional groups. Examples of polymerizable hydrophilic monomers having at least one carboxyl group may include, but are not limited to, methacrylic acid, maleic acid p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid and the anhydride thereof, 4-methacryloyloxyethyltrimellitic acid ("4-MET") and an anhydride thereof ("4-META"), 4-(2-hydroxy-3-methacryloyloxy) butyltrimellitic acid and an anhydride thereof, 2,3-bis(3,4-dicarboxybenzoyloxy)propyl methacrylate, methacryloyloxytyrosine, N-methacryloyloxytyrosine, N-methacryloyloxyphenylalanine, methacryloyl-p-aminobenzoic acid, an adduct of 2-hydroxyethyl methacrylate with pyromellitic dianhydride (PMDM), and an adduct of 2-hydroxyethyl methacrylate with 3,3', 4,4'-benzophenonetetracarboxylic dianhydride (BTDA) or 3,3',4,4'-biphenyltetracarboxylic dianhydride. Hydrophilic monomers may include BPDM, the reaction product of an aromatic dianhydride with an excess of 2-HEMA (2-hydroxyethyl methacrylate), as disclosed in U.S. Pat. No. 5,348,988, which are incorporated by reference as if fully set forth herein. Other hydrophilic monomers may include EDMT, the reaction product of 2-hydroxyethyl methacrylate ("2-HEMA") with ethylene glycol bistrimellitate dianhydride; DSDM, the reaction product of 3,3',4,4'-diphenylsulfone tetracarboxylic dianhydride and 2-HEMA; PMDM, and PMGDM, the adduct of pyromellitic dianhydride with glycerol dimethacrylate.

Examples of polymerizable compounds having at least one phosphoric acid group may include, but are not limited to 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, and 2 methacryloyloxyethylphenyl acidophosphate. The phosphoric acid group in these compounds may be replaced with a thiophosphoric acid group.

Examples of polymerizable compounds may include 2-methacryloyloxyethylphenyl acidophosphate and 10-methacryloyloxydecyl acidophosphate. Examples of polymerizable monomers having at least one sulfonic acid group include 2-sulfoethyl methacrylate, 3-sulfo-2-butyl methacrylate, 3-bromo-2-sulfo-2-propyl methacrylate, 3-methoxy-1-sulfo-2-propyl methacrylate, and 1,1-dimethyl-2-sulfoethyl methacrylamide.

All the above polymerizable monomers may be used alone or in combination. All of the above polymerizable compounds may be first polymerized and then added to a composition as a polymer. Polymers may be purchased. In some embodiments, a polymer may be combined with a bridged polycyclic compound to form a composition. Polymers may further polymerize during a curing process after a composition has been applied to an oral surface. In some embodiments, a polymer, added to a composition, may include poly (vinyl acetate-co-crotonic acid). A composition may include a prepolymer and/or a polymer capable of forming a film. A composition may include one or more solvents. Solvents may include environmentally green solvents (e.g., water, alcohol (e.g., ethanol). Solvents may be applied to an oral surface as part of a composition. At least some of the solvents may evaporate as the composition forms a film over the oral surface to which the composition was applied.

A dental composition may include a polymerization initiator system, including light curing, self-curing, dual curing, and vacuum, heat, and pressure curing systems as well as any combination thereof. Visible light curing systems employ light-sensitive compounds (e.g., benzil diketones and DL-camphorquinone) in amounts ranging from about 0.05 to 0.5 weight percent. Visible light curing systems may include polymerization accelerators (e.g., various organic tertiary amines well known in the art). In visible light curable compositions, the tertiary amines are generally acrylate derivatives such as dimethylaminoethyl methacrylate and, particularly, diethylaminoethyl methacrylate ("DEAME") in amounts in the range from about 0.05 to 0.5 weight percent.

Self-curing compositions may contain free radical polymerization initiators such as, for example, peroxides in amounts ranging from about 2 to 6 weight percent. Suitable free radical initiators may include lauryl peroxide, tributyl hydroperoxide, cumene hydroperoxide, and benzoyl peroxide. The heat and pressure curable systems also include heat cure initiators such as aromatic sulfinic acids and salts thereof, benzoyl peroxide, 1,1'-azobis (cyclohexanecarbonitrile), or other free radical initiators. Polymerization accelerators commonly used with these include tertiary amines, generally aromatic tertiary amines such as ethyl 4-(N,N-dimethyl)aminobenzoate ("EDAB"), dimethyl-p-toluidine, dihydroxyethyl-p-toluidine and the like, in amounts ranging from about 0.05 to about 4.0 weight percent.

The dental restorative compositions may also comprise other additives and solvents known in the art, for example, ultraviolet light absorbers, anti-oxidants such as BHT, stabilizers, fillers, pigments, opacifiers, handling agents, and others. An ultraviolet absorber may be employed in amounts ranging from about 0.05 to about 5.0 weight percent. Such ultraviolet absorbers may be desirable in the visible light curable compositions in order to avoid discoloration of the resin from any incident ultraviolet light. Suitable ultraviolet absorbers may include gelators, various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y.

Fillers, such as colloidal silica, barium glasses, fibrous fillers, quartz, ceramic fillers and the like may also be incorporated into dental compositions, particularly when they are to be used as bonding agents, luting cements or filling composites. Suitable fillers may include fillers conventionally used in the dental industry capable of being covalently bonded to the resin matrix itself or to a coupling agent which is covalently bonded to both. Silane coupling agents are known, for example methacryloxypropyl trimethoxy silane. Such fillers are described in U.S. Pat. Nos. 4,544,359 and 4,547,531, which is incorporated by reference as if fully set forth herein. Examples of suitable filling materials may include, but are not limited to, amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof. Particularly suitable fillers for dental filling-type materials prepared are those having a particle size in the range from about 0.1 to about 5.0 microns, together with a silicate colloid having particle sizes in the range from about 0.001 to about 0.07 microns.

Antimicrobials may be generally effective against organisms which cause secondary decay, and must not adversely affect the required physical properties of the cured compositions, in particular water sorption, diametral tensile strength, and hardness. In particular, the ADA specification No. 27 requires dental resin composites to have water sorption values below 50 $\mu g/mm^3$/week. Commercial dental restorative materials used as, filling materials preferably have water sorption values of less than about 30, less than about 20, or less than about 15 $\mu g/mm^3$/week. The ADA specification No. 27 specifies that the diametral tensile strength for filled dental composite (type II) should be a minimum of 34 MPa. Commercial dental restorative materials used as filling materials may have DTS values of greater than about 38, greater than about 40, or greater than about 45 MPa. Dentine bonding strength must be at least about 10 MPa, at least about 15 MPa, at least about 18 MPA, or at least about 20 MPa.

Dental compositions may be used as bonding primers or adhesives. When dental compositions are to be used as bonding primers, adhesives, or primer/adhesives, volatile solvents such as water, alcohol, acetone, and the like are used to dilute the polymerizable compound(s). The particular amounts of polymerizable compound(s) and solvent may be adjusted so as to provide sufficient viscosity such that they can be applied in one or a relatively few number of coats and achieve a uniform thin coating, of the dental substrate, while providing high bonding strengths between the dental substrate and the restorative material or dental component. Optionally, additional polymerizable compounds, optional self-life stabilizers, or other modifying ingredients known in the art may be incorporated.

Dental compositions may be used as a bonding agent and/or base liner under restorative materials such as resin composites, silver amalgam alloys, and the like.

Calculus is the brown build-up of plaque found extending downwards on the tooth from the gum line. Calculus is a haven for bacteria which can have serious consequences for your pet's general health. These bacteria can not only cause abscesses and tooth loss but can have effects further afield—even resulting in organ damage as the bacteria are carried from the mouth, through the bloodstream.

Dental compositions may be used as dental luting cements and/or cavity filling materials.

In some embodiments, elements used within an antimicrobial coatings as described herein is association with other applications or elsewhere herein (e.g., under the "Matrices" heading) may also be incorporated into a composition for dental purposes.

EXAMPLES

Having now described the invention, the same will be more readily understood through reference to the following example(s), which are provided by way of illustration, and are not intended to be limiting of the present invention.

General Experimental: All manipulations were carried out using Schlenk technique. Concentrated hydrochloric acid and acetic acid were purchased from J. T. Baker and used as received. Sodium hydroxide was purchased from Mallinckrodt and used as received. Sodium dicyanamide and sodium bicarbonate were purchased from Aldrich and used as received. Tris(2-aminoethyl)amine was purchased from Acros Organics and distilled before use. Terephthaldicarboxaldehyde and p-chloroaniline were purchased from Aldrich and sublimed before use. Sodium sulfate was purchased from EMD and used as received. Water was sparged for >10 minutes before use. Dichloromethane, ethyl acetate and hexanes were purchased from EMD and used as received. Ethyl alcohol, anhydrous 200 proof, was purchased from Aldrich and used as received. Silica gel 60 (230-400 mesh) was purchased from EMD and used as received. MS analysis was performed on an Applied Biosystems Voyager DE instrument at HT Laboratories in San Diego, Calif. NMR analysis was performed on a JEOL Eclipse+ 400 instrument at Acorn NMR, Inc. in Livermore, Calif.

Synthesis of 2: To a 12 L round bottom flask equipped with a reflux condenser and addition funnel was added methanol (8 L) followed by terephthaldicarboxaldehyde (64.4 g, 0.480 moles). The solution was heated to 65° C. and tris(2-aminoethyl)amine (46.8 g, 47.9 mL, 0.320 moles) was added. Then the solution was refluxed for about 16 h and cooled to room temperature. The solution was filtered to another 12 L round bottom flask equipped with a reflux condenser and sodium borohydride (60.5 g, 1.60 moles) was added. The solution was refluxed for about 16 h and cooled to room temperature. The volatiles were removed by rotational evaporator and the residue dissolved in dichloromethane (720 mL) and hydrochloric acid, 1.0 M (3.2 L). It was stirred for 5 minutes. Then to the solution was added sodium hydroxide, 3.0 M (1.6 L), the solution stirred for 5 minutes and the phases separated. The aqueous was extracted with dichloromethane (2×400 mL, 2×200 mL), the organic phase combined, washed with water (2×600 mL) and dried over sodium sulfate. Then the volatiles were removed by vacuum transfer to leave a slightly off white powder (89.6 g, 150 mmoles, 93.5% yield). Analysis of 2: $^1$H NMR (400 MHz, $CD_2Cl_2$, δ): 2.61, 2.76 (m, 24H, $NCH_2CH_2NHCH_2C_6H_4$), 3.62 (s, 12H, $NCH_2CH_2NHCH_2C_6H_4$), 6.84 (s, 12H, $NCH_2CH_2NHCH_2C_6H_4$). ESI-MS (m/z): $[M+H]^+$ 599, $[M+H]^{2+}$ 300.

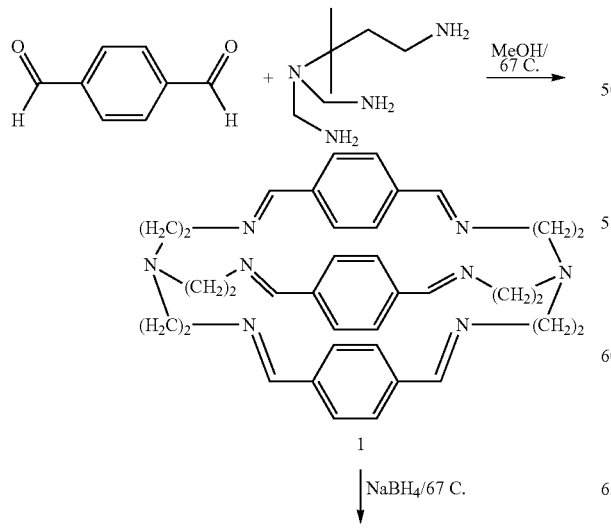

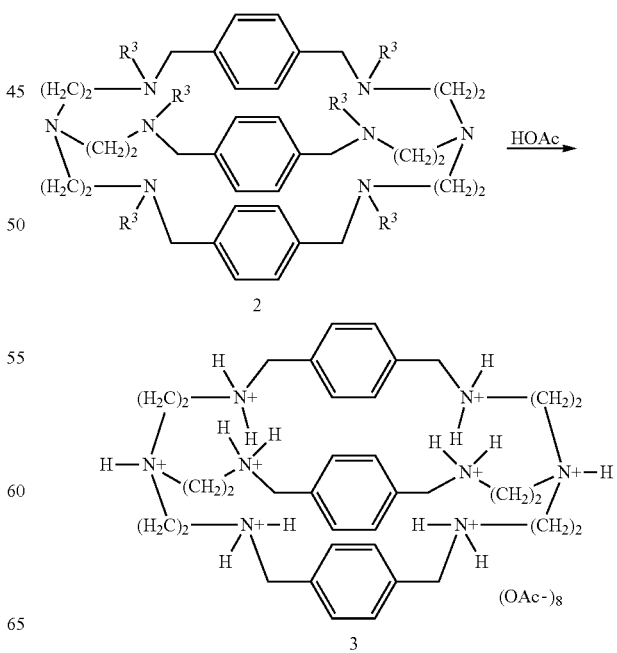

Synthesis of 3: Octa-amine 2 (19.9 g, 33.3 mmoles) was added to a 2 L flask and combined with ethyl acetate (924 mL) and acetic acid (38.1 mL, 40.0 g, 666 mmoles). The solution was filtered and hexanes (629 mL) was added which caused the product to crystallize. The solution was filtered and the precipitate washed with 80% hexanes, 20% ethyl acetate (1500 mL). The product was transferred to a flask and the volatiles removed by vacuum transfer. The supernatant was combined with hexanes (300 mL), filtered and washed with of 80% hexanes, 20% ethyl acetate (1500 mL). The precipitate was transferred to a flask and the volatiles removed by vacuum transfer. To the supernatant was added the wash solution from the second crop which precipitated the third crop of product. The solution was filtered and washed with 80% hexanes, 20% ethyl acetate (1500 mL). The precipitate was transferred to a flask and the volatiles removed by vacuum transfer. The product is a slightly off white powder (33.7 g, 31.3 mmoles, 93.9% yield). Alternatively, 2 is suspended in ethyl alcohol followed by the slow addition of 20 equiv of glacial acetic acid followed by stirring; the solvent and excess acid are removed via rotary evaporation and or a schenk line under vacuum resulting in 3. Analysis of 3: $^1$H NMR (400 MHz, Methanol-$d_4$, δ): 1.88 (s, 24H, $CH_3CO_2$), 2.78, 3.24 (m, 24H, $CH_2CH_2$), 4.14 (s, 12H, $NCH_2Ph$), 7.47 (s, 12H, Ph). MALDI-MS (m/z): $[M]^+$ 600, $[M+Na]^+$ 622.

Synthesis of 4: The compound p-chloroaniline (170 g, 1.33 moles) was added to a 1 L flask and dissolved in water (625 mL) and concentrated HCl (111 mL, 1.33 moles). Then in a separate 5 L flask sodium dicyanamide (237 g, 2.66 moles) was dissolved in water (2035 mL) and heated to 50° C. The solution of p-chloroaniline was added to the solution of sodium dicyanamide over 120 minutes, the flask was fitted with a reflux condenser and then the reaction solution was heated for about 16 h at 90° C. Then the reaction solution was allowed to cool and saturated sodium bicarbonate (1500 mL) was added and the solution stirred for 15 minutes. Ethyl acetate (1000 mL) was added and the solution stirred for 10 minutes before the phases were separated. The aqueous phase was extracted with ethyl acetate (10×1000 mL, 500 mL), the organic was combined and washed with saturated brine (3×1200 mL), dried over sodium sulfate (anhydrous) and filtered. A 10 cm deep silica plug was packed with silica/ethyl acetate slurry and then washed with ethyl acetate (2000 mL). The product was sent through the silica plug and the plug washed with ethyl acetate (6000 mL). The volatiles were removed from the filtrate by vacuum transfer until about 10% of the solution remained and the solution was filtered. The product was dried under vacuum to p<20 mtorr to leave a white powder. Then the product was placed under vacuum again at p<20 mtorr while on a 70° C. oil bath for 18 h (203 g, 1.04 moles, 78.3% yield). Analysis of 4: $^1$H NMR (400 MHz, DMSO-$d_6$, δ): 7.08 (s, 2H, PhNHC(NH)NHCN), 7.36 (m, 4H, Ph), 9.15 (s, 1H, PhNHC(NH)NHCN). MALDI-MS (m/z): $[M]^+$ 195, $[M+Na]^+$ 218.

Synthesis of compound 4 has been described in patent GB599722 and J. Chem. Soc. 1946, p 729-737 and 1948, p 1630-1636, which are incorporated by reference as if fully set forth herein. Synthesis of compounds similar to compound 4 are described in U.S. Pat. Nos. 2,455,807 and 5,534,565, which are incorporated by reference as if fully set forth herein.

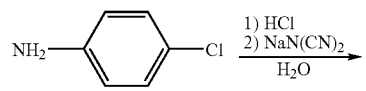

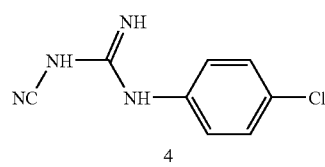

4

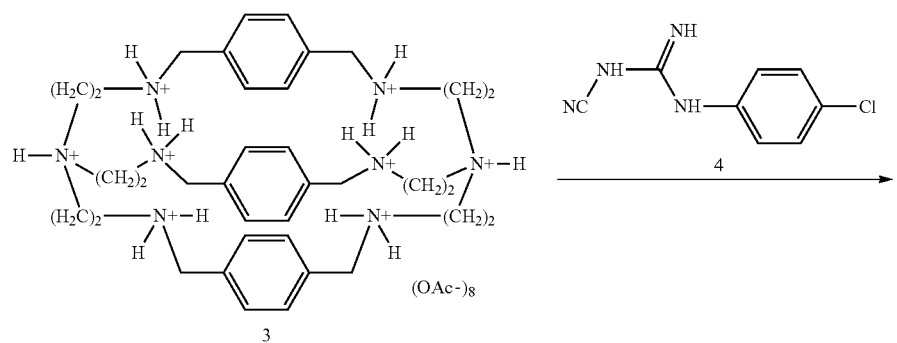

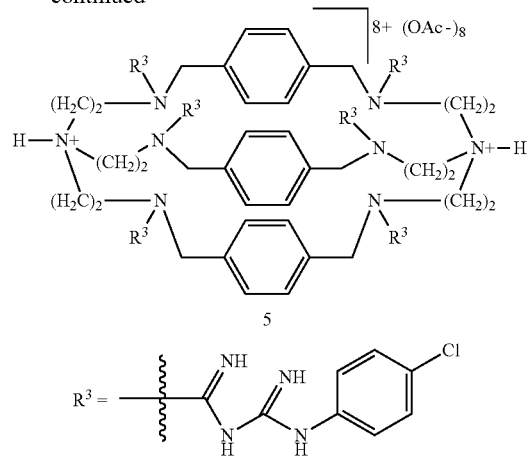

Synthesis of 5: Intermediate 3 (32.9 g, 30.5 mmoles) was added to a 500 mL flask followed by 1-butanol (30.3 mL) which formed a slurry. Then 4 (39.1 g, 201 mmoles) was added. The flask was fitted with a reflux condenser and placed into an oil bath set to reach 90° C. It was heated for 3 days and allowed to cool to room temperature. The volatiles were removed by vacuum transfer and the resulting foam was crushed to a powder. The crude product was dissolved in ethyl alcohol (31.9 mL) and ethyl acetate (65.4 mL). The product was precipitated with ethyl acetate (915 mL) and the solution filtered. Then the product was washed with ethyl acetate (980 mL) and the volatiles removed by vacuum transfer to produce a white powder (57.9 g, 25.8 mmoles, 84.5% yield). Alternatively, the resulting crude product 5 foam was crushed to a powder and dissolved in water followed by extraction of the aqueous phase 3 times with ethyl acetate resulting in an off white powder 5 in ~77% yield. Analysis of 5: MALDI-MS (m/z): 1269 $[M+5\ DHB]^{2+}$, 1423 $[M+7\ DHB]^{2+}$ (DHB is MALDI matrix dihydroxybenzoic acid).

The product 5 can be converted to the freebase and then protonated with mineral, organic or other acids to afford the desired counterion (anion) (for example 5 can be treated with base, isolated as the freebase and treated with acetic acid to regenerate 5, i.e. replace acetic acid with a different acid such as D-Gluconic Acid (or combination of acids (i.e. etidronic acid, 1-hydroxyethylidenediphosphonic acid)) to generate the salt containing the desired anion counter-ion). Analysis of Freebase 5: MALDI-MS (m/z): 883 $[M]^{2+}$. Alternatively, the desired counterion may be useful and or introduced in the synthesis of 5 in place of the counterion (OAc) shown in structure 3 used to generate 5 shown above. This may assist in bone growth in the oral cavity or other desired effects.

Formulation of Dental Sealant Varnish

General: Poly(vinyl acetate-co-crotonic acid) beads and ethyl alcohol (anhydrous 200 proof) were purchased from Aldrich and used without further purification.

Example: Poly(vinyl acetate-co-crotonic acid) (0.80 g) was dissolved in water (1.74 mL) and ethyl alcohol (7.81 mL). Compound 5 (0.50 g) was dissolved in ethyl alcohol (1.00 mL). The two solutions were combined and mixed for 2 hours.

Double Blind Beagle Dog Clinical Trial Results with Dental Sealant Varnish:

The Double blind study included 12 beagle dogs, 6 male, 6 female approximately 3 years of age randomly selected for the Study Group and Control Group, 6 dogs per group. Each dog, under anesthesia, received a prophylaxis (teeth cleaning) on one side of the mouth (upper and lower jaw) and no prophylaxis (teeth cleaning) on the opposite side of the mouth (upper and lower jaw); a split mouth design.

All Dogs were assessed on both the upper and lower jaw and right and left side of the mouth: Incisor (I), Canine (C), Premolar 3 (P3), Premolar 4 (P4), Molar 1 (M1). The following parameters were scored for each dog before any product application: Gingivitis Index; scale of 0-5, Gingival Bleeding Index; scale of 0-5, Plaque Index; scale of 0-3, Calculus Index; scale of 0-3 and Pocket Depth; measured and recorded in mm three points per tooth).

An overall score for each dog for Gingivitis Index; scale of 0-5, Gingival Bleeding Index; scale of 0-5, Plaque Index; scale of 0-3, Calculus Index; scale of 0-3; upper and lower jaw, right and left side of the mouth was also recorded weekly for 63 days.

Results of Double Blind Beagle Dog Clinical Trial Results with Dental Sealant Varnish Study, Day 63

Control Group, Total Gingivitis: 83.3%; vs. Dental Sealant Varnish Group, Total Gingivitis: 16.6%.

Control Group no Prophylaxis Side, Bleeding: 100%; vs. Dental Varnish Group no Prophylaxis Side Bleeding: 50%.

Control Group Prophylaxis Side, Bleeding: 60%; vs. Dental Varnish Group Prophylaxis Side Bleeding: 33%.

In Summary for the Canine Study: significant reduction in gingivitis, gingival bleeding and periodontal disease was seen with a single application of the Dental Sealant Varnish with or without a prophylaxis (dental cleaning).

A dental checkup and assessment more than Six Months after application of the Dental Sealant Varnish showed similar results in that the Dental Sealant Varnish Group vs. the Control Group in overall oral health.

Results of Feline Clinical Trial Results with Dental Sealant Varnish Study, Day 41

Similarly, a feline study with 12 cats (no prophylaxis), 6 Control Group and 6 Dental Varnish Sealant Study Group was conducted and is ongoing. Both groups were assessed and scored similarly to the dogs for gingivitis, gingival bleeding, plaque and calculus. In addition, any FORLs (Feline odontoclastic resorptive lesions), Stomatitis and/or CUPS (Chronic ulcerative paradental stomatitis) were recorded and given a severity score ranking.

The Dental Varnish Sealant was applied to the Dental Varnish Sealant Study Group (one initial application, then weekly applications from week 4 onward, a 63 day study) to the teeth and any Stomatitis, FORLS (Feline odontoclastic resorptive lesions) or CUPS (Chronic ulcerative paradental stomatitis) observed sites in the oral cavity. The Control Group did not receive any Dental Sealant Varnish application.

Two of the Dental Varnish Sealant Study Group cats had Stomatitis and/or CUPS (Chronic ulcerative paradental stomatitis) so severe (large bleeding and infected mouth sores) that they were losing weight rapidly and did not eat before the start of the study. FORLs (Feline odontoclastic resorptive lesions), extensively bleeding CUPS sores and irritation was observed at the start of the study before any Dental Varnish Sealant was applied to the Dental Varnish Sealant Study Group.

Most impressive was the significant improvement in as little as 7 days after application of product to CUPS (Chronic ulcerative paradental stomatitis), FORLs (Feline odontoclastic resorptive lesions), and/or Stomatitis which were observed at the start of the study in the Dental Varnish Sealant Group. After 41 days the CUPS (Chronic ulcerative paradental stomatitis) lesions were under control, no longer bleeding and the cats were eating normally with significant weight gain (~0.4 kilograms).

In Summary for the Feline Study: significant reduction in gingivitis, gingival bleeding, FORLs (Feline odontoclastic resorptive lesions), CUPS (Chronic ulcerative paradental stomatitis), Stomatitis as well as plaque and calculus reduction was observed for the Dental Varnish Sealant Study Group with no significant change for the Control Group.

Other common dental formulation or coating formulation components known by those skilled in the art may be used in conjunction with or in place of the above example In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of coating a human oral surface, comprising:

applying a chemical compound to at least a portion of a human oral surface, the chemical compound comprising a bridged polycyclic compound having a structure (Ib):

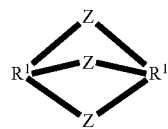
(Ib)

wherein Z comprises at least one bridge, wherein at least one of the bridges is $-R^2-N^+R^3{}_2-R^4-N^+R^3{}_2-R^2-$, $-R^2-NR^3-R^4-N^+R^3{}_2-R^2-$, or $-R^2-NR^3-R^4-NR^3-R^2-$, and wherein each bridge independently couples $R^1$ to $R^1$;

wherein each $R^1$ is independently N, $N^+H$, or $N^+R^3$;

wherein each $R^2$ is independently an alkyl group, a substituted alkyl group, or an alkene;

wherein each $R^3$ is independently a pharmaceutically active agent, a hydrogen, an ester, an alkyl group, a substituted alkyl group, an aryl group, a substituted aryl group, a heterocycle group, a substituted heterocycle group, an alkene, an ether, a guanidine derivative, a polyethyleneglycol, a polyethyleneimine, or any combination of these, and wherein at least two $R^3$s are a pharmaceutically active agent comprising a guanidine or a guanidine derivative;

wherein each $R^4$ is independently an aryl group or a substituted aryl group;

wherein when $R^4$ is an aryl group the aryl group is a phenyl, a naphthyl, a biphenyl, a diphenylmethyl, or a benzophenone; and wherein when $R^4$ is a substituted aryl group the substituted aryl group is a phenyl having at least one substituent, a naphthyl having at least one substituent, a biphenyl having at least one substituent, a diphenylmethyl having at least one substituent, or a benzophenone having at least one substituent;

forming a coating over at least a portion of the human oral surface;

inhibiting or ameliorating at least one malady associated with a human oral surface, oral cavity and/or tissue associated with an oral cavity; and wherein at least one of the maladies is a tooth lesion, dental fracture, periodontal disease, stomatitis, gingivitism, inflammation of periodontal structures, oral mucosa, lips and/or tongue, palatitis, faucitis, glossal ulceration, pharyngitis, submandibular lymphadenopathy, wound, or an infection.

2. The method of claim 1, wherein Y is a halogen, an alcohol, or a pharmaceutically active agent;

wherein X is a counterion;

wherein n ranges from 1-10, 2-8, 2-4, 3-6, 2-3, or 1-3;

wherein each z is independently a charge on the chemical compound and an appropriate number of counterions, wherein z ranges from 1-16, 2-14, 6-14, 8-14, or 12-20; and wherein Z comprises at least one bridge, wherein at least one of the bridges is

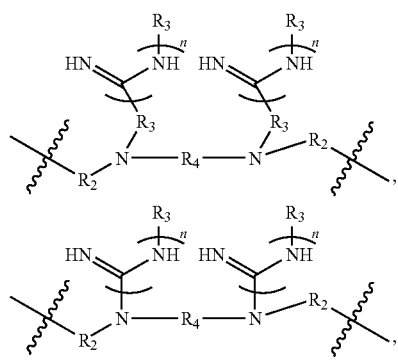

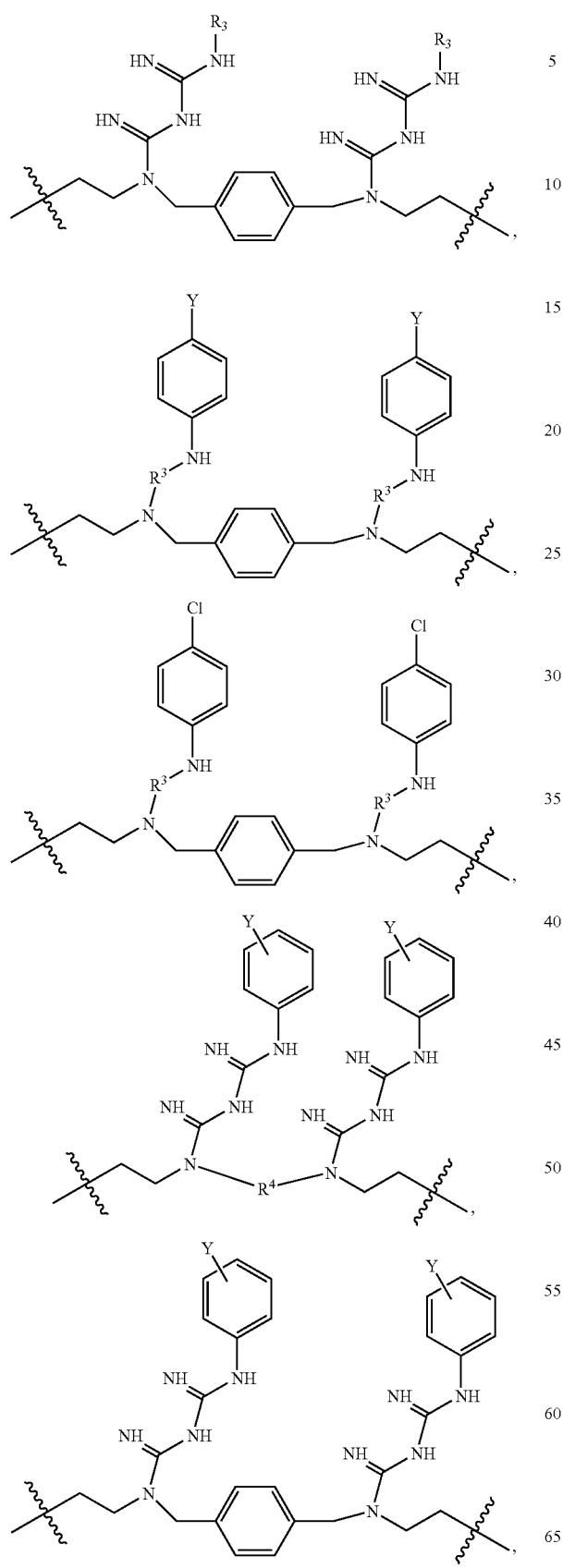

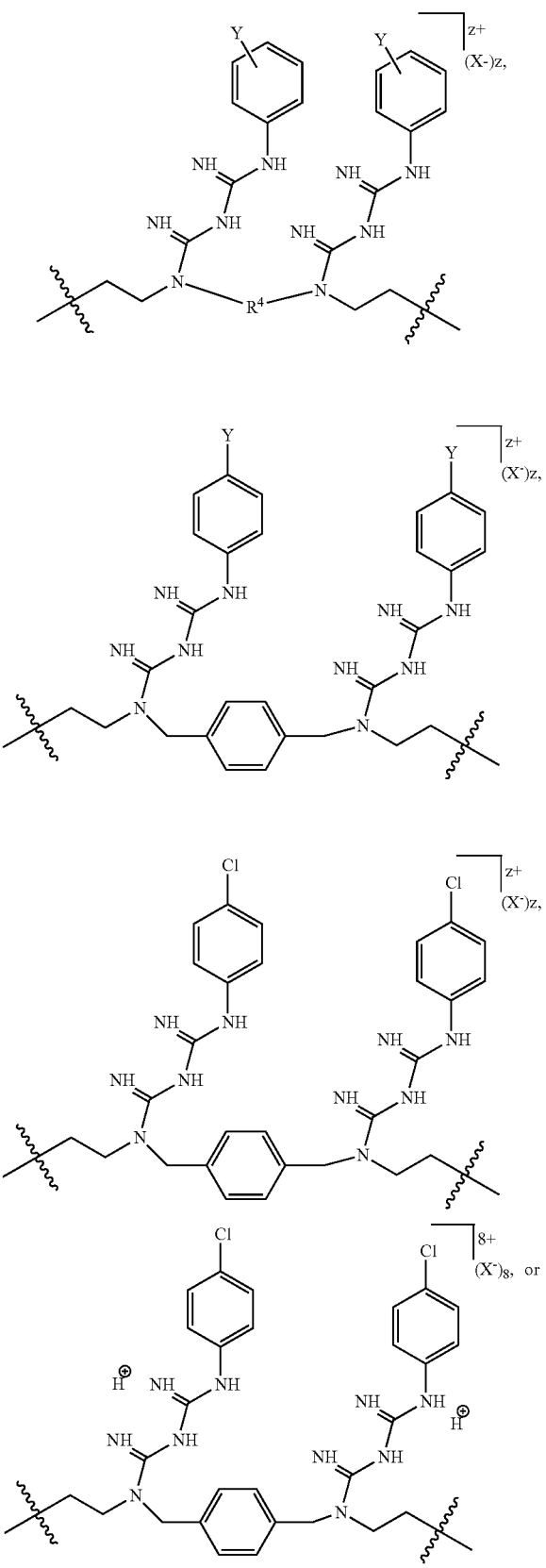

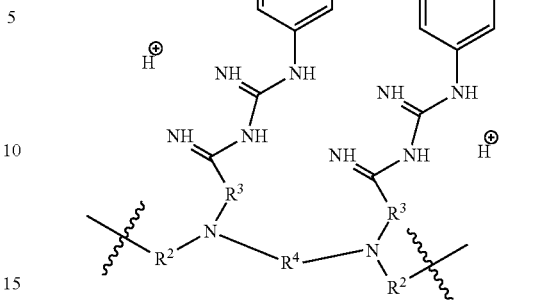

3. The method of claim 2, wherein X is an acetate.

4. The method of claim 2, wherein X is a bisphosphonate.

5. The method of claim 2, wherein each X is independently a bisphosphonate, wherein the bisphosphonate comprises Etidronate, Clodronate, Tiludronate, Pamidronate, Neridronate, Olpadronate, Alendronate, Ibandronate, Risedronate, or Zoledronate.

6. The method of claim 2, wherein each X is independently Lipoic acid, Linoleic acid, or a fatty acid.

7. The method of claim 1, wherein the chemical compound is a salt of the chemical compound.

8. The method of claim 1, wherein the chemical compound is part of a chemical composition, and wherein the chemical composition comprises a polymer or a prepolymer.

9. The method of claim 1, wherein the chemical compound is part of a chemical composition, and wherein the chemical composition comprises a polymer or a prepolymer, wherein at least one polymer is poly(vinyl acetate-co-crotonic acid).

10. The method of claim 1, wherein the chemical compound is part of a chemical composition, and wherein the chemical composition comprises an alcohol based solvent, wherein at least one alcohol is ethanol.

11. The method of claim 1, wherein at least one of the pharmaceutically active agents is an antiviral agent.

12. The method of claim 1, wherein at least one of the pharmaceutically active agents is an anti-inflammatory agent.

13. The method of claim 1, wherein at least one of the pharmaceutically active agents is an antimicrobial agent.

14. The method of claim 1, wherein at least one of the pharmaceutically active agents is an antigen blocker or inhibitor.

15. The method of claim 1, wherein at least one of the pharmaceutically active agents is an allergen blocker or inhibitor.

16. The method of claim 1, wherein at least one of the pharmaceutically active agents is an periodontal disease agent, a periodontal bacteria attachment inhibitor, a periodontal disease enzyme inhibitor, and/or a periodontal disease enzyme attachment inhibitor.

17. The method of claim 1, wherein the oral surface comprises at least a portion of a tooth surface, at least a portion of a gum, at least a portion of soft tissue, at least a portion of bone, and/or at least a portion of a dental fixture.

18. The method of claim 1, wherein the oral surface comprises at least a portion of a dental fixture, wherein the dental fixture comprises a filling, at least a portion of a bridge, and/or at least a portion of a denture.

19. The method of claim 17, wherein the oral surface comprises at least a portion of soft tissue on or near a tooth extraction site, at least a portion of soft tissue on or near a root canal site, at least a portion of a tooth on or near a root canal site, at least a portion of soft tissue on or near an oral surgery site, at least a portion of a tooth on or near an oral surgery site, at least a portion of bone on or near a tooth extraction site, and/or at least a portion of bone on or near an oral surgery site.

20. The method of claim 1, wherein a substituted aryl group comprises an alkyl-aryl group or a substituted alkyl-aryl group.

* * * * *